United States Patent
Burns

(10) Patent No.: US 11,865,095 B2
(45) Date of Patent: Jan. 9, 2024

(54) COMBINATION DRUG SUBSTANCE OF POLYAMINE TRANSPORT INHIBITOR AND DFMO

(71) Applicant: Aminex Therapeutics, Inc., Kenmore, WA (US)

(72) Inventor: Mark R. Burns, Epsom, NH (US)

(73) Assignee: Aminex Therapeutics, Inc., Kenmore, WA (US)

( * ) Notice: Subject to any disclaimer, the term of this patent is extended or adjusted under 35 U.S.C. 154(b) by 56 days.

(21) Appl. No.: 17/490,492

(22) Filed: Sep. 30, 2021

(65) Prior Publication Data

US 2022/0096412 A1   Mar. 31, 2022

Related U.S. Application Data

(60) Provisional application No. 63/085,510, filed on Sep. 30, 2020.

(51) Int. Cl.

| | | |
|---|---|---|
| A61K 31/13 | (2006.01) | |
| A61K 31/381 | (2006.01) | |
| A61K 31/341 | (2006.01) | |
| A61K 31/18 | (2006.01) | |
| A61K 31/132 | (2006.01) | |
| A61K 31/131 | (2006.01) | |
| A61P 35/00 | (2006.01) | |
| A61K 31/198 | (2006.01) | |

(52) U.S. Cl.
CPC ............ *A61K 31/198* (2013.01); *A61K 31/13* (2013.01); *A61K 31/131* (2013.01); *A61K 31/132* (2013.01); *A61K 31/18* (2013.01); *A61K 31/341* (2013.01); *A61K 31/381* (2013.01); *A61P 35/00* (2018.01)

(58) Field of Classification Search
CPC .. A61K 31/198; A61K 31/131; A61K 31/132; A61K 31/18; A61K 31/341; A61K 31/381; A61K 31/13; A61P 35/00
See application file for complete search history.

(56) References Cited

U.S. PATENT DOCUMENTS

| | | |
|---|---|---|
| 4,309,442 A | 1/1982 | Bey et al. |
| 4,590,288 A | 5/1986 | Klemann |
| 4,774,339 A | 9/1988 | Haugland et al. |
| 4,818,770 A | 4/1989 | Weinstein et al. |
| 4,950,744 A | 8/1990 | Dattagupta et al. |
| 5,187,288 A | 2/1993 | Kang et al. |
| 5,248,782 A | 9/1993 | Haugland et al. |
| 5,252,714 A | 10/1993 | Harris et al. |
| 5,274,113 A | 12/1993 | Kang et al. |
| 5,433,896 A | 7/1995 | Kang et al. |
| 5,451,663 A | 9/1995 | Kang et al. |
| 5,541,230 A | 7/1996 | Basu et al. |
| 5,648,394 A | 7/1997 | Boxall et al. |
| 5,654,287 A | 8/1997 | Prakash et al. |
| 5,656,671 A | 8/1997 | Bergeron, Jr. |
| 6,172,261 B1 | 1/2001 | Vermeulin et al. |
| 6,235,737 B1 | 5/2001 | Styczynski et al. |
| 6,646,149 B1 | 11/2003 | Vermeulin et al. |
| 6,743,419 B1 | 6/2004 | Shander et al. |
| 6,872,852 B2 | 3/2005 | Burns |
| 6,914,079 B2 | 7/2005 | Burns et al. |
| 6,963,010 B2 | 11/2005 | Burns et al. |
| 7,144,920 B2 | 12/2006 | Burnsm et al. |
| 7,160,923 B1 | 1/2007 | Vermeulin et al. |
| 7,199,267 B1 | 4/2007 | Burns et al. |
| 7,208,528 B1 | 4/2007 | Vermeulin et al. |
| 7,388,112 B2 | 6/2008 | Burns et al. |
| 7,411,002 B2 | 8/2008 | Burns et al. |

(Continued)

FOREIGN PATENT DOCUMENTS

| | | |
|---|---|---|
| EP | 1 085 011 A1 | 3/2001 |
| GB | 1041596 | 9/1966 |

(Continued)

OTHER PUBLICATIONS

Chen et al. Int. J. Cancer, 2006, vol. 118, Iss. 9, p. 2344-2349 (Year: 2006).*
Hayes et al. Cancer Immunol Res. 2014, 2 (3): 274-285 (Year: 2014).*
Advisory Action for U.S. Appl. No. 11/050,789, titled: "Hydrophobic Polyamine Analogs And Methods For Their Use," dated Oct. 3, 2007.
Advisory Action for U.S. Appl. No. 11/062,481, titled: "Hydrophobic Polyamine Analogs And Methods For Their Use," dated Mar. 14, 2008.
Ajani, J.A., et al. "Evaluation of continuous-infusion alpha-difluoromethylornithine therapy for colorectal carcinoma", Cancer Chemother Pharmacol 26, 223-226 (1990).

(Continued)

*Primary Examiner* — Mark L Shibuya
*Assistant Examiner* — Luisalberto Gonzalez
(74) *Attorney, Agent, or Firm* — Hamilton, Brook, Smith & Reynolds, P.C.

(57) ABSTRACT

Provided herein are combinations comprising difluoromethylornithine (DFMO), or an ionic form thereof, and a compound of the following structural formula:

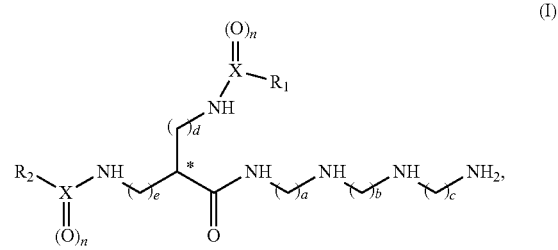

or a protonated form thereof, wherein values for the variables (e.g., a, b, c, d, e, n, $R_1$, $R_2$, X) are described herein. The combinations can provide combination drug therapy in a single pharmaceutical dosage form, and be used, for example, for the treatment of cancer.

22 Claims, 18 Drawing Sheets

(56) References Cited

U.S. PATENT DOCUMENTS

| | | | |
|---|---|---|---|
| 7,432,302 B2 | 10/2008 | Burns et al. | |
| RE43,327 E * | 4/2012 | Burns | C07D 333/34 |
| | | | 564/84 |
| 8,258,186 B2 | 9/2012 | McKearn et al. | |
| 8,609,734 B2 | 12/2013 | McKearn et al. | |
| 10,632,145 B2 | 4/2020 | Burns | |
| 11,395,834 B2 | 7/2022 | Burns | |
| 2003/0187276 A1 | 10/2003 | Burns et al. | |
| 2005/0176828 A1 | 8/2005 | Burns et al. | |
| 2005/0245615 A1 | 11/2005 | Burns et al. | |
| 2006/0122279 A1* | 6/2006 | Burns | A61K 31/132 |
| | | | 514/626 |
| 2009/0318847 A1 | 12/2009 | Sebree et al. | |
| 2011/0027172 A1 | 2/2011 | Wang et al. | |
| 2011/0256161 A1 | 10/2011 | Burns et al. | |
| 2015/0038512 A1 | 2/2015 | Looper et al. | |
| 2019/0008892 A1 | 1/2019 | Burns | |
| 2020/0352983 A1 | 11/2020 | Burns | |
| 2023/0088829 A1 | 3/2023 | Burns | |

FOREIGN PATENT DOCUMENTS

| | | | |
|---|---|---|---|
| JP | 02 256656 A | 10/1990 | |
| JP | 09 235271 | 9/1997 | |
| JP | 2004-529082 A | 9/2004 | |
| JP | 2008-519856 A | 6/2008 | |
| JP | 2011-524901 A | 9/2011 | |
| WO | WO 1985/002769 A1 | 7/1985 | |
| WO | WO 1991/000853 A1 | 1/1991 | |
| WO | WO 1992/014709 A2 | 9/1992 | |
| WO | WO 1995/021612 A2 | 8/1995 | |
| WO | WO 1996/022926 A1 | 8/1996 | |
| WO | WO 1996/038464 A1 | 12/1996 | |
| WO | WO 1997/033560 A1 | 9/1997 | |
| WO | WO 1999/003823 A2 | 1/1999 | |
| WO | WO 1999/054283 A1 | 10/1999 | |
| WO | WO 2000/034226 A1 | 6/2000 | |
| WO | WO 2000/046187 A2 | 8/2000 | |
| WO | WO 2001/072685 A2 | 10/2001 | |
| WO | WO 2002/053519 A2 | 7/2002 | |
| WO | WO 2007/001455 A2 | 1/2007 | |
| WO | WO 2009/154648 A1 | 12/2009 | |
| WO | WO 2017/165313 A1 | 9/2017 | |
| WO | WO-2017165313 A1 * | 9/2017 | A61K 31/785 |
| WO | 2022/072586 A1 | 4/2022 | |

OTHER PUBLICATIONS

Ajani, J.A., et al., "Alterations in polyamine metabolism during continuous intravenous infusion of alpha-difluoromethylornithine showing correlation of thrombocytopenia with alpha-difluoromethylornithine plasma levels", Cancer Res 49, 5761-5765 (1989).
Albanese, L., et al., "Investigations of the Mechanism by which Mammalian Cell Growth is Inhibited b $N^1N^{12}$-Bis(ethyl)spermine," Biochem. J., 291: 131-7 (1993).
Alberts, D.S., et al. Chemoprevention of human actinic keratoses by topical 2-(difluoromethy1)-dl-ornithine. Cancer Epidemiol Biomarkers Prev 9, 1281-1286 (2000).
Alhohen-Hongisto, L. et al., "Tumourigenicity, Cell-Surface Glycoprotein Changes and Ornithine Decarbboxylase Gene Pattern in Ehrlich Ascites-Carcinoma Cells," Biochem J., 229: 711-715 (1985).
Alhonen-Hongisto, L., et al., "Intracellular Putrescine Deprivation Induces Uptake of the Natural Polyamines and Methylglyoxal Bis(Guanylhydrazone)," Biochem. J. 192: 941-945 (1980).
Amidon, G.L., et al., "A theoretical basis for a biopharmaceutic drug classification: the correlation of in vitro drug product dissolution and in vivo bioavailability", Pharm Res 12, 413-420 (1995).
Aramaki, Y. et al., "Chemical Characterization of Spider Toxin, JSTX," Proc Japan Acad, 62, Ser. B: 359-362 (1986).
Ask, A., et al., "Increased Survival of L1210 Leukemic Mice by Prevention of the Utilization of Extracellular Polyamines. Studies Using a Polyamine-Uptake Mutant, Antibiotics and a Polyamine-Deficient Diet," Cancer Lett., 66: 29-34 (1992).
Atwell, G., et al. "Potential antitumor agents. 45. Synthesis, DNA-binding interaction, and biological activity of triacridine derivatives," J. Med. Chem., 29(1): 69-74 (1986).
Baguley, B.C., "DNA Intercalating Anti-Tumour Agents," Anti-Cancer Drug Design, 6: 1-35 (1991).
Baillon, et al., "Inhibition of mammalian spermine synthase by N-alkylated-1,3-diaminopropane derivatives in vitro and in cultured rat hepatoma cells," Eur. J. Biochem., vol. 179, pp. 17-21 (1989).
Baker, N., et al., "Genome-wide RNAi screens in African trypanosomes identify the nifurtimox activator NTR and the eflornithine transporter AAT6", Mol Biochem Parasitol 176, 55-57 (2011).
Balasundaram, D., et al., "Polyamine-DNA Nexus: Structural Ramifications and Biological Implications," Mal. Cell. Biochem., 100: 129-40 (1991).
Bardocz, S., et al., "Polyamines in food; Implications for Growth and Health," J Nutr. Biochem., 4: 66-71 (1993).
Bauer, et al., "Nitric Oxide Inhibits Ornithine Decarboxylase via S-Nitrosylation of Cysteine 360 in the Active Site of the Enzyme," The Journal of Biological Chemistry, vol. 276, No. 37, pp. 34458-34464 (2001).
Baze, et al., "Distribution of polyamines in human epidermis," British Journal of Dermatology, vol. 112, pp. 393-396 (1985).
Bello-Fernandez, C., et al., "c-myc transactivates the ornithine decarboxylase gene," Curr Top Microbiol Immunol 182, 445-452 (1992).
Bello-Fernandez, C., et al., "The ornithine decarboxylase gene is a transcriptional target of c-Myc", Proc Natl Acad Sci U S A 90, 7804-7808 (1993).
Benaouda, F., et al. "Ion-Pairing with Spermine Targets Theophylline To the Lungs via the Polyamine Transport System", Mol Pharm 15, 861-870 (2018).
Berge, et al., "Pharmaceutical Salts," Journal of Pharmaceutical Sciences, vol. 66, pp. 1-18 (1977).
Bergeron, R.J. et al., "Total Synthesis (+)-15-Deoxyspergualin," J. Org. Chem., vol. 57; 1700-3 (1987).
Bergeron, R.J., et al., "Reagents for the Stepwise Functionalization of Spermine," J. Org. Chem, 53: 3108-11 (1988).
Bergeron, R.J., et al., "A Comparison of Structure-Activity Relationships between Spermidine and Spermine Analogue Antineoplastics," J. Med. Chem., 40: 1475-94 (1997).
Bergeron, R.J., et al., "Antiproliferative Properties of Polyamine Analogues: A Structure-Activity Study," J. Med. Chem., 37: 3464:76 (1994).
Bey, et al., "α-(Fluoromethyl)dehydroornithine and α-(Fluoromethyl)dehydroputrescine Analogues as Irreversible Inhibitors of Ornithine Decarboxylase," J. Med. Chem, vol. 26, pp. 1551-1556 (1983).
Bey, et al., Analogues of Ornithine as Inhibitors of Ornithine Decarboxylase. New Deductions Concerning the Topography of the Enzyme's Active Site, Journal of Medicinal Chemistry, vol. 21 No. 1, pp. 50-55 (1978).
Bey, et al., Inhibition of Basic Amino Acid Decarboxylases Involved in Polyamine Biosynthesis, Sjoerdsma Academic Press, pp. 1-31 (1987).
Bhargava, P., et al., "A phase I and pharmacokinetic study of squalamine, a novel antiangiogenic agent, in patients with advanced cancers," Clin Cancer Res 7, 3912-3919 (2001).
Bitonti, A.J., et al., "Uptake of alpha-difluoromethylornithine by Trypanosoma brucei brucei", Biochem Pharmacol 35, 351-354 (1986).
Blagbrough, I.S., et al., "Arthropod toxins as leads for novel insecticides: as assessment of polyamine amides as glutamate antagonists," Toxicon, vol. 30, No. 3: 303-22 (1992).
Blagbrough, I.S., et al., "Asymmetric intercalation of N1-(acridin-9-ylcarbonyl)spermine at homopurine sites of duplex DNA," Chem. Commun., 929-930 (1998).
Blagbrough, I.S., et al., "Measurement of polyamine pKa values", Methods Mal. Biol. 2011, 720, 493-503.
Blagbrough, I.S., et al., "Practical Synthesis of the Putative Polyamine Spider Toxin FTX: a Proposed Blocker of Voltage-Sensitive Calcium Channels," Tetrahedron Lett., 35(13): 2057-60 (1994).

(56) References Cited

OTHER PUBLICATIONS

Blagbrough, I.S., et al., "Practical Synthesis of Unsymmetrical Polyamine Amides," Tetrahedron Lett, 39: 439-442 (1998).
Bogle, R.G., et al., "Endothelial Polyamine Uptake: Selective Stimulation by L-arginine Deprivation," Am J Physiol, 266: C776-C783 (1994).
Bonaiuto E. et al., "Novel polyamine analogues: From substrates towards potential inhibitors of monoamine oxidases", Eur. J. Med. Chem., 70:88-101 (2013).
Boncher, T. et al. "Polyamine-based analogues as biochemical probes and potential therapeutics", Biochem. Soc. Trans., 35(2):356-363 (2007).
Booth, R.J., et al., "Polymer-Supported Quenching Reagents for Parallel Purification," J. Am. Chem. Soc., 119: 4882-6 (1997).
Borch, R.F., et al., "The Cyanohydridoborate Anion as a Selective Reducing Agent," J. Am. Chem. Soc., 93(12): 2897-2904 (1971).
Bowlin, T.L., et al., "Effect of polyamine depletion in vivo by DL-alpha-difluoromethylornithine on functionally distinct populations of tumoricidal effector cells in normal and tumor-bearing mice," Cancer Res 46, 5494-5498 (1986).
Bowlin, T.L., et al., "Effects of three irreversible inhibitors of ornithine decarboxylase on macrophage-mediated tumoricidal activity and antitumor activity in B16F1 tumor-bearing mice," Cancer Res 50, 4510-4514 (1990).
Boyle, J.O., et al., "Polyamine contents in rectal and buccal mucosae in humans treated with oral difluoromethylornithine", Cancer Epidemiol Biomarkers Prev 1, 131-135 (1992).
Brand, G., et al., "Cyclopolyamines: Synthesis of Cyclospermidines and Cyclospermines, Analogues of Spermidine and Spermine," Tetrahedron Lett., 35(46): 8609-12 (1994).
Bray, A.M., et al., "Simultaneous Multiple Synthesis of Peptide Amides by the Multipin Method. Application of Vapor-Phase Ammonolysis," J. Org. Chem., 59: 2197-2203 (1994).
Brown, H.C., et al., "Solvomercuration-Demercuration. I. The Oxymercuration-Demercuration of Representative Olefins in an Aqueous System. A Convenient Mild Procedure for the Markovnikov Hydration of the Carbon-Carbon Double Bond," J. Org. Chem., 35(6):1844-50 (1970).
Bruce, et al., "Structure-Activity Relationships of analogues of the Wasp Toxin Philanthotoxin: Non-Competitive Antagonists of Quisqualate Receptors," Toxicon, 28(11): 1333-1346 (1990).
Bukin, Y.V., et al. "Effect of prolonged beta-carotene or DL-alpha-tocopheryl acetate supplementation on ornithine decarboxylase activity in human atrophic stomach mucosa", Cancer Epidemiol Biomarkers Prev 4, 865-870 (1995).
Burns, M.R., et al. Abstract 2006: AMX-513 polyamine depletion therapy inhibits tumor growth and reverses immunosuppression in cancers including MYC-driven neuroblastoma and pancreatic cancer. Cancer Research 77, 2006-2006 (2017).
Burns, M.R., Graminski, G.F., Weeks, R.S., Chen, Y. & O'Brien, T.G. Lipophilic lysine-spermine conjugates are potent polyamine transport inhibitors for use in combination with a polyamine biosynthesis inhibitor. J Med Chem 52, 1983-1993 (2009).
Bussiere, F.I., et al. "Spermine causes loss of innate immune response to Helicobacter pylori by inhibition of inducible nitric-oxide synthase translation", The Journal of Biological Chemistry 280:2409-2412 (2005).
Butler, J.E., et al., "The Physical and Functional Behavior of Capture Antibodies Adsorbed on Polystyrene," J. Immunol. Meth., 150: 77-90 (1992).
Byk, G., et al., "One Pot Synthesis of Unsymmetrically Functionalized Polyamines by a Solid Phase Strategy Starting from their Symmetrical Polyamine-Counterparts," Tetrahedron Lett., 38(18): 3219-22 (1997).
Canizares, F., et al. Prognostic value of ornithine decarboxylase and polyamines in human breast cancer: correlation with clinicopathologic parameters. Clin Cancer Res 5, 2035-2041 (1999).
Carbone, P.P., et al. "Bioavailability study of oral liquid and tablet forms of alpha-difluoromethylornithine", Clin Cancer Res 6, 3850-3854 (2000).
Carbone, P.P., et al. Phase I chemoprevention study of difluoromethylornithine in subjects with organ transplants. Cancer Epidemiol Biomarkers Prev 10, 657-661 (2001).
Carrington, S., et al., "Inhibition of growth of B16 Murine Melanoma Cells by Novel Spermine Analogs," Pharm Sci, 2(1): 25-27 (1996).
Casara, et al., "Stereospecific Synthesis of (2R,5R)-Hept-6-yne-2,5-diamine: A Potent and Selective Enzyme-activated Irreversible Inhibitor of Ornithine Decarboxylase (ODC)," J. Chem. Perkin Trans., pp. 2201-2207 (1985).
Casero RA, "Say What? The Activity of the Polyamine Biosynthesis Inhibitor Difluoromethylornithine in Chemoprevention Is a Result of Reduced Thymidine Pools", Cancer Discovery, 975-977 (Sep. 2013).
Casero, Jr., R.A., et al., "High Specific Induction of Spermidine/Spermins N'-Acetyltransferase in a Human Large Cell Lung Carcinoma," Biochem. J., 270: 615-20 (1990).
Casero, R.A., Jr., et al., "Polyamine metabolism and cancer: treatments, challenges and opportunities", Nat Rev Cancer 18, 681-695 (2018).
Chamaillard, L. et al., "Polyamine Deprivation Prevents the Development of Tumor-Induced Immune Supression," Br J Cancer, 76:365-370 (1997).
Chamaillard, L., et al., "Polyamine deprivation stimulates natural killer cell activity in cancerous mice," Anticancer Res 13, 1027-1033 (1993).
Chan, P.P., et al., "Triplex DNA: Fundamentals, Advances, and Potential Applications for Gene Therapy," J. Mal. Med., 75: 267-82 (1997).
Chang, B.K., et al., "Modulation of polyamine biosynthesis and transport by oncogene transfection", Biochem Biophys Res Commun 157, 264-270 (1988).
Chao, J., et al., "N1-Dansyl-Spermine and N1-(n-octanesulfonyl)-Spermine, Novel Glutamate Receptor Antagonists: Block and Permeation of N-Methyl-D-Aspartate Receptors," Mol Pharmacol, 51(5): 861-871 (1997).
Chaplinski, V., et al., "A Versatile New Preparation of Cyclopropylamines from Acid Dialkylamides," Angew. Chem. Int. Ed. Engl., 35(4): 413-4 (1996).
Chaturvedi, R., et al. "Induction of polyamine oxidase 1 by Helicobacter pylori causes macrophage apoptosis by hydrogen peroxide release and mitochondrial membrane depolarization", The Journal of Biological Chemistry, 279:40161-40173 (2004).
Chen et al., "Combination therapy with 2-difluoromethylomithine and polyamine transport inhibitor against murine squamous cell carcinoma," Int. J. Cancer, vol. 118; 2344-2349 (2006).
Chen, Y., Megosh, L.C., Gilmour, S.K., Sawicki, J.A. & O'Brien, T.G. K6/ODC transgenic mice as a sensitive model for carcinogen identification. Toxicol Lett 116, 27-35 (2000).
Claverie, N. & Mamont, P.S. Comparative antitumor properties in rodents of irreversible inhibitors of L-ornithine decarboxylase, used as such or as prodrugs. Cancer Res 49, 4466-4471 (1989).
Coni, S., et al. Blockade of EIF5A hypusination limits colorectal cancer growth by inhibiting MYC elongation. Cell Death Dis 11, 1045 (2020).
Cullis, P. et al., "Probing the mechanism of transport and compartmentalisation of polyamines in mammalian cells," Chemistry & Biology, 6(10): 717-729 (1999).
Danzin et al., "α-Allenyl putrescine, an enzyme-activated irreversible inhibitor of bacterial and mammalian ornithine decarboxylases," Federation of European Biochemical Societies, vol. 174, No. 2, pp. 275-278 (1984).
Danzin, C., et al., L-ornithine-induced inactivation of mammalian ornithine decarboxylase in vitro. Eur J Biochem 166, 45-48 (1987).
Danzin, et al., α-Ethynyl and α-Vinyl Analogues of Ornithine as Enzyme-Activated Inhibitors of Mammalian Ornithine Decarboxylase, J. Med. Chem., vol. 24, pp. 16-20 (1980).
Davis, R.H., Lieu, P. & Ristow, J.L. Neurospora mutants affecting polyamine-dependent processes and basic amino acid transport mutants resistant to the polyamine inhibitor, alpha-difluoromethylornithine. Genetics 138, 649-655 (1994).

(56) References Cited

OTHER PUBLICATIONS

De Clercq, E. Recent advances on the use of the CXCR4 antagonist plerixafor (AMD3100, Mozobil) and potential of other CXCR4 antagonists as stem cell mobilizers. Pharmacol Ther 128, 509-518 (2010).
Dempcy, R.O., et al., "Design and Synthesis of Ribonucleic Guanidine: A Polycationic Analog of RNA," Proc. Natl. Acad. Sci. U.S.A, 93: 4326-30 (1996).
Devraj, R., et al., "A Versatile Solid Phase Synthesis of Lavendustin A and Certain Biologically Active Analogs," J. Org. Chem., 61 :9368-73 (1996).
Dhainaut, et al., "New Purines and Purine Analogs as Modulators of Multidrug Resistance," J Med Chem, 39:4099-4108 (1996).
Dhingra, K., et al. Phase I clinical and pharmacological study of suppression of human antimouse antibody response to monoclonal antibody L6 by deoxyspergualin. Cancer Res 55, 3060-3067 (1995).
Dimery, I.W., et al. "Polyamine metabolism in carcinoma of the oral cavity compared with adjacent and normal oral mucosa",. Am J Surg 154, 429-433 (1987).
DiPasquale, A., et al., "Epidermal Growth Factor Stimulates Putrescine Transport and Ornithine Decarboxylase Activity in Cultures Human Fibroblasts," Exp Cell Res, 116: 317-323 (1978).
Doll, M., et al., "Synthesis of Tenuilobine, a Bis-polyamine Alkaloid from Oncinotis tenuiloba, and Its Transamidation to Isotenuilobine," Helv. Chim. Acta, vol. 79, No. 2, pp. 541-547 (1996).
Douglas, S.P., et al., "Polymer-Supported Solution Synthesis of Oligosaccharides Using a Novel Versatile Linker for the Synthesis of D-Mannopentaose, a Structural Unit of D-Mannans of Pathogenic Yeasts," J. Am. Chem. Soc., 117: 2116-7 (1995).
Drug Fut., 16: 1165-1166 (1991).
Dyshlovoy, S.A., et al. Proteomic profiling of germ cell cancer cells treated with aaptamine, a marine alkaloid with antiproliferative activity. J Proteome Res 11, 2316-2330 (2012).
Eisenburg, T. et al. "Cardioprotection and lifespan extension by the natural polyamine spermidine", Nature Medicine, 22(12):1428-1438 (2016).
Eriksson, C., et al., "MALDI Imaging Mass Spectrometry—A Mini Review of Methods and Recent Developments," Mass Spectrom (Tokyo) 2, S0022 (2013).
Erwin, B.G. & Pegg, A.E. Uptake of alpha-difluoromethylornithine by mouse fibroblasts. Biochem Pharmacol 31, 2820-2823 (1982).
European Extended Search Report for Application No. 17770923.5 "Bioavailable Polyamines" dated Oct. 15, 2019.
Evageliou, N.F., et al., "Polyamine Antagonist Therapies Inhibit Neuroblastoma Initiation and Progression," Clin Cancer Res 22, 4391-4404 (2016).
Evans, et al. "Spermine-directed immunosuppression of cervical carcinoma cell sensitivity to a majority of lymphokineactivated killer lymphocyte cytotoxicity",. Nat. lmmun., 14:157-163 (1995).
Felschow, D.M. et al., "Selective Labeling of Cell-Surface Polyamine-Binding Proteins on Leukemic and Solid-Tumor Cell Types Using a New Polyamine Photoprobe," Biochem J, 328(3): 889-895 (1997).
Felschow, D.M., et al., "Photoaffinity Labeling of a Cell Surface Polyamine Binding Protein," J. Biol. Chem., 270(48): 28705-11 (1995).
Fillingame et al., "Increased cellular levels of spermidine or spermine are required for optimal DNA synthesis in lymphocytes activated by concanavalin A," Proc. Nat. Acad. Sci. USA, vol. 72, No. 10, pp. 4042-4045 (1975).
Final Office Action for U.S. Appl. No. 11/050,789, titled: "Hydrophobic Polyamine Analogs And Methods For Their Use," dated Jun. 25, 2007.
Final Office Action for U.S. Appl. No. 11/050,789, titled: "Hydrophobic Polyamine Analogs And Methods For Their Use," dated Aug. 4, 2008.
Final Office Action for U.S. Appl. No. 11/062,481, titled: "Hydrophobic Polyamine Analogs And Methods For Their Use," dated Nov. 20, 2007.
Fiori L.M et al. "Implication of the polyamine system in mental disorders", J. Psychiatry Neurosci., 33(2):102-110 (2008).
Flemming, S.A., "Chemical Reagents in Photoaffinity Labeling," Tetrahedron, 51(46): 12479-520 (1995).
Flescher, E., et al., "Polyamine oxidation down-regulates IL-2 production by human peripheral blood mononuclear cells," J Immunol 142, 907-912 (1989).
Flescher, E., et al., "Increased Polyamines May Downregulate Interleukin 2 Production in Rheumatoid Arthritis," J. Clin. Invest., 83: 1356-62 (1989).
Fujimura, K., Wang, H., Watson, F. & Klemke, R.L. KRAS Oncoprotein Expression Is Regulated by a Self-Governing eIF5A-PEAK1 Feed-Forward Regulatory Loop. Cancer Res 78, 1444-1456 (2018).
Furka, A., "General Method for Rapid Synthesis of Multicomponent Peptide Mixtures," Int. J. Peptide Protein Res., 37: 487-93 (1991).
Furumitsu, Y., et al., "Levels of Urinary Polyamines in Patients with Rheumatoid Arthritis," J. Rheumatology, 20(10): 1661-5 (1993).
Gaines, D.W., et al., Apparent ornithine decarboxylase activity, measured by 14CO2 trapping, after frozen storage of rat tissue and rat tissue supernatants. Anal Biochem 174, 88-96 (1988).
Gallop, M.A., et al., "Applications of Combinatorial Technologies to Drug Discovery. Background and Peptide Combinatorial Libraries. ," J. Med. Chem., 37(9): 1233-51 (1994).
Gamble, L.D., et al., "Inhibition of polyamine synthesis and uptake reduces tumor progression and prolongs survival in mouse models of neuroblastoma," Sci Transl Med 11(2019).
Ganem, B., "New Chemistry of Naturally Occuring Polyamines," Acc. Chem. Res., 15: 290-8 (1982).
Garewal, H.S., Sloan, D., Sampliner, R.E. & Fennerty, B. Ornithine decarboxylase assay in human colorectal mucosa. Methodologic issues of importance to quality control. Int J Cancer 52, 355-358 (1992).
Geerts, D., et al. The polyamine metabolism genes ornithine decarboxylase and antizyme 2 predict aggressive behavior in neuroblastomas with and without MYCN amplification. Int J Cancer 126, 2012-2024 (2010).
Gensler, H.L. Prevention by alpha-difluoromethylornithine of skin carcinogenesis and immunosuppression induced by ultraviolet irradiation. J Cancer Res Clin Oncol 117, 345-350 (1991).
Gerner, E.W. & Meyskens, F.L., Jr. Polyamines and cancer: old molecules, new understanding. Nat Rev Cancer 4, 781-792 (2004).
Gerner, E.W., et al., Gastrointestinal tissue polyamine contents of patients with Barrett's esophagus treated with alpha-difluoromethylornithine. Cancer Epidemiol Biomarkers Prev 3, 325-330 (1994).
Gervais, A., et al. "Dendritic cells are defective in breast cancer patients: a potential role for polyamine in this immunodeficiency", Breast Cancer Res., 7:R326-335 (2005).
Gervais, A., et al. "Ex vivo expansion of antitumor cytotoxic lymphocytes with tumor-associated antigen-loaded dendritic cells", Anticancer Research 25, 2177-2185 (2005).
Gilad GM et al., "Novel Polyamine Derivatives and Neuroprotective Agents", Pharmacology and Experimental Therapeutics, 291(1):39-43 (1999).
Gilmour, et al., "Polyamine Blocking Therapy Decreases Survival of Tumor-Infiltrating Immunosuppressive Myeloid Cells and Enhances the Anti-Tumor Efficacy of PD-1 Blockade", Mol Cancer Ther (2020).
Gobert, A.P., et al. Hypusination Orchestrates the Antimicrobial Response of Macrophages. Cell Rep 33, 108510 (2020).
Golub et al., "Molecular Classification of Cancer: Class Discovery and Class Prediction by Gene Expression Monitoring," Science, vol. 286, pp. 531-537 (1999).
Goodnow, Jr., R., et al., "Synthesis of Glutamate Receptor Antagonist Philanthotoxin-433 (PhTX-433) and its Analogs," Tetrahedron Lett., 46(9): 3267-86 (1990).
Goodnow, Jr., R.A., et al., "Oligomer Synthesis and DNA/RNA Recognition Properties of a Novel Oligonucleotide Backbone Analog: Glucopyranosyl Nuclei Amide (GNA)," Tetrahedron Lett., 38(18): 3199-3202 (1997).
Goodnow, Jr., R.A., et al., "Synthesis of Thymine, Cytosine, Adenine, and Guanine Containing N-Fmoc Protected Amino Acids: Building Blocks for Construction of Novel Oligonucleotide Backbone Analogs," Tetrahedron Lett., 38(18): 3195-8 (1997).

(56) References Cited

OTHER PUBLICATIONS

Gordon, D.W., et al., "Reductive Alkylation on a Solid Phase: Synthesis of a Piperazinedione Combinatorial Library," Bioorg. Med. Chem. Lett., 5(1): 47-50 (1995).
Gordon, E.M., et al., "Applications of Combinatorial Technologies to Drug Discovery. Combinatorial Organic Synthesis, Library Screening Strategies, and Future Directions," J. Med. Chem., 37(10): 1385-1401 (1994).
Gorus, F., et al., "Applications of Bio- and Chemiluminescence in the Clinical Laboratory," Clin. Chem., 25(4): 512-9 (1979).
Green, A.C. et al., "Polyamine Amides are Neuroprotective in Cerebellar Granule Cell Cultures Challenged with Excitatory Amino Acids," Brain Research 717/1-2: 135-146 (1996).
Griffin, C.A., et al. Phase I trial and pharmacokinetic study of intravenous and oral alpha-difluoromethylornithine. Invest New Drugs 5, 177-186 (1987).
Ha, H.C. et al. "The Natural Polyamine Spermine Functions Directly as a Free Radical Scavenger," Proc Natl Acad Sci USA, 95: 11140-11145 (1998).
Ha, H.C. et al., "The Role of Polyamine Catabolismin Polyamine Analogue-Induced Programmed Cell Death," Proc. Natl. Acad. Sci., 94: 11557-62 (1997).
Haegele, K.D., Alken, R.G., Grove, J., Schechter, P.J. & Koch-Weser, J. Kinetics of alpha-difluoromethylornithine: an irreversible inhibitor of ornithine decarboxylase. Clin Pharmacol Ther 30, 210-217 (1981).
Hahm, H.A., et al. Phase I study of N(1),N(11)-diethylnorspermine in patients with non-small cell lung cancer. Clin Cancer Res 8, 684-690 (2002).
Han, H. et al., "Liquid-Phase Combinatorial Synthesis," Proc. Natl. Acad. Sci. USA, 92: 6419-23 (1995).
Hanauske-Abel, H. M. et al., "Detection of a Sub-Set of Polysomal mRNAs Associated with Modulation of Hypusine Formation at the G1-S Boundary Proposal of a Role for elf-5A in onset of DNA Replication," FEBS Lett., 366: 92-8 (1995).
Hatanaka, T., et al., "Ion pair skin transport of a zwitterionic drug, cephalexin", J Control Release 66, 63-71 (2000).
Hayashi, S. et al. "Ornithine Decarboxylase Antizyme: A Novel Type of Regulatory Protein," Trends In Biochemical Sciences, 21: 27-30 (1996).
Hayes, C.S., Burns, M.R. & Gilmour, S.K. Polyamine blockade promotes antitumor immunity. Oncoimmunology 3, e27360 (2014).
Hayes, C.S., et al. A prolonged and exaggerated wound response with elevated ODC activity mimics early tumor development. Carcinogenesis 32, 1340-1348 (2011).
Hayes, C.S., et al. Polyamine-blocking therapy reverses immunosuppression in the tumor microenvironment. Cancer Immunol Res 2, 274-285 (2014).
Heller, J.S. et al. "Induction of a Protein Inhibitor to Ornithine Decarboxylase by the End Products of Its Reaction," Proc Natl Acad Sci USA, 73: 1858-1862 (1976).
Herbst, R.S., et al. A phase I/IIA trial of continuous five-day infusion of squalamine lactate (MSI-1256F) plus carboplatin and paclitaxel in patients with advanced non-small cell lung cancer. Clin Cancer Res 9, 4108-4115 (2003).
Hernandez, A.S. et al., "Solid-Supported tert-Alkoxycarbonylation Reagents for Anchoring of Amines During Solid Phase Organic Synthesis," J. Org. Chem., 62: 3153-7 (1997).
Herrera-Ornelas, L., et al. A comparison of ornithine decarboxylase and S-adenosylmethionine decarboxylase activity in human large bowel mucosa, polyps, and colorectal adenocarcinoma. J Surg Res 42, 56-60 (1987).
Higashi et al., "Structural and Functional Relationship among Diamines in Terms of Inhibition of Cell Growth," J. Biochem., vol. 136, pp. 533-539 (2004).
Hixson, L.J., et al. Ornithine decarboxylase and polyamines in colorectal neoplasia and mucosa. Cancer Epidemiol Biomarkers Prev 2, 369-374 (1993).

Holley, J., et al., "Uptake and Cytotoxicity of Novel Nitroimidazole-Polyamine Conjugates in Ehrlich Ascites Tumour Cells," Biochem. Pharmacol., 43(4): 763-9 (1992).
Holley, J.L., et al., "Targeting of Tumor Cells and DNA by a Chlorambucil-Spermidine Conjugates," Cancer Res., 52: 4190-5 (1992).
http://www.msnbc.msn.com/id/7320341, Hair follicles offer source of nerve stem cells Mouse whisker cells turned into neurons, researchers say, Hair follicles offer source of nerve stem cells, 2005, p. 1.
Huber, M. et al., "2,2'-Dithiobis (N-ethyl-spermine-5-carboxamide) Is a High Affinity, Membrane-lmpermeant Antagonist of the Mammalian Polyamine Transport System," J. Biol. Chem., 271(44): 27556-63 (1996).
Huber, M. et al., "Antiproliferative Effect of Spermine Depletion by N-Cyclohexyl-1,3-diaminopropane in Human Breast Cancer Cells," Cancer Res., 55: 934-43 (1995).
Huff, J.R., "HIV protease: a novel chemotherapeutic target for AIDS," J. Med. Chem., 34(8): 2305-14 (1991).
Hynd, et al., "Inhibition of Polyamine Synthesis Alters Hair Follicle Function and Fiber Composition," The Society for Investigative Dermatology, vol. 106, No. 2, pp. 249-253 (1996).
Hyvönen, M.T., et al., Assay of Ornithine Decarboxylase and Spermidine/Spermine N1-acetyltransferase Activities. Bio-protocol 4, e1301 (2014).
International Preliminary Examination Report for International Application No. PCT/US2002/00347, titled: "Hydrophobic Polyamine Analogs and Methods For Their Use," dated Oct. 17, 2003.
International Preliminary Report on Patentability for International Application No. PCT/US2017/023250, titled: "Bioavailable Polyamines," dated Oct. 4, 2018.
International Search Report and Written Opinion for International Application No. PCT/US2017/023250, titled: "Bioavailable Polyamines," dated Jun. 21, 2017.
International Search Report for International Application No. PCT/US2002/000347, titled: "Hydrophobic Polyamine Analogs and Methods For Their Use," dated Dec. 4, 2002.
Ishiwata, K., Abe, Y., Matsuzawa, T. & Ido, T. Tumor uptake studies of D,L-[5-14C]ornithine and D,L-2-difluoromethyl [5-14C]ornithine. Int J Rad Appl Instrum B 15, 119-122 (1988).
Ivaturi, V.D. et al., "Enhanced permeation of methotrexate in vitro by ion pair formation with L-arginine", J Pharm Sci 98, 3633-3639 (2009).
Iwanowicz, E.J. et al., "Preparation of N,N'-Bis-tert-Butoxycarbonylthiourea," Synthetic Comm., 23(10): 1443-5 (1993).
Keough, M.P., Hayes, C.S., DeFeo, K. & Gilmour, S.K. Elevated epidermal ornithine decarboxylase activity suppresses contact hypersensitivity. J Invest Dermatol 131, 158-166 (2011).
Khan, A., et al. "Dual targeting of polyamine synthesis and uptake in diffuse intrinsic pontine gliomas," Nat Commun 12, 971 (2021).
Khan, N., Quemener, V. et al., "Characterization of Polyamine Transport pathways", in Neuropharmacology of Polyamines (Carter, C., ed.), Academic, San Diego, pp. 37-60 (1994).
Kilpelainen, P.T. & Hietala, O.A. Activation of rat brain ornithine decarboxylase by GTP. Biochem J 300 ( Pt 2), 577-582 (1994).
Klier, H., et al. Isolation and structural characterization of different isoforms of the hypusine-containing protein eIF-5A from HeLa cells. Biochemistry 34, 14693-14702 (1995).
Kobayashi, et al., "Control Spermidine and Spermine Levels in Rat Tissues by trans-4-Methylcyclohexylamine, a Spermidine-Synthase Inhibitor," Biol. Pharm. Bull., vol. 28, No. 4, pp. 569-573 (2005).
Kohl, N.E., Gee, C.E. & Alt, F.W. Activated expression of the N-myc gene in human neuroblastomas and related tumors. Science 226, 1335-1337 (1984).
Koike, M. et al., "Blocking effect of 1-naphthyl acetyl spermine on $Ca^{2+}$-permeable AMPA receptors in cultured rat hippocampal neurons," Neuroscience Research, 29: 27-36 (1997).
Koone, et al., "A Mode of Action for Butylated Hydroxytoluene-Mediated Photoprotection," Journal of lnvestigative Derm., vol. 87., No. 3, pp. 343-347 (1986).
Kossorotow, A. et al., "Regulatory Effects of Polyamines on Membrane-Bound Acetylcholinesterase," Biochem J, 144: 21-27 (1974).

(56) References Cited

OTHER PUBLICATIONS

Kozumbo, et al., "Inhibition by 2(3)-tert-Butyl-4-hydroxyanisole and Other Antioxidants of Epidermal Ornithine Decarboxylase Activity Induced by 12-O-Tetradecanoylphorbol-13-acetate," Cancer Research, vol. 43, pp. 2555-2559 (1983).
Krapcho, A.P. et al., "Mono-Protected Diamines. N-tert-Butoxycarbonyl-a,w-Alkanediamines from α,ω-Alkanediamines," Syn Comm, 20: 2559-2564 (1990).
Kremmer, T. et al., "Comparative Studies on the Polyamine Metabolism and DFMO Treatment of MCF-7 and MDA-MB-231 Breast Cancer Cell Lines and Xenografts," Anticancer Res., 11: 1807-14 (1991).
Kruczynski, A., et al. F14512, a polyamine-vectorized anti-cancer drug, currently in clinical trials exhibits a marked preclinical anti-leukemic activity. Leukemia 27, 2139-2148 (2013).
Lack, N.A., et al. A pharmacokinetic-pharmacodynamic model for the mobilization of CD34+ hematopoietic progenitor cells by AMD3100. Clin Pharmacol Ther 77, 427-436 (2005).
Laguzza, B.C., et al., "A New Protecting Group For Amines: Synthesis of Anticapsin from LTyrosine," Tetrahedron Lett., 22(16): 1483-6 (1981).
Lakanen et al., Synthesis and Biochemical Evaluation of Adenosylspermidine, a Nucleoside-Polyamine Adduct Inhibitor of Spermidine Synthase, J. Med. Chem., vol. 38, pp. 2714-2727 (1995).
Lakanen, J.R., et al., "a-Methyl Polyamines: Metabolically Stable Spermidine and Spermine Mimics Capable of Supporting Growth in Cells Depleted of Polyamines," J. Med. Chem., 35: 724-34 (1992).
Lam, K.S., "Application of Combinatorial Library Methods in Cancer Research and Drug Discovery," Anti-Cancer Drug Des., 12: 145-67 (1997).
LaMuraglia, G.M., Lacaine, F. & Malt, R.A. High ornithine decarboxylase activity and polyamine levels in human colorectal neoplasia. Ann Surg 204, 89-93 (1986).
Lan, L., Hayes, C.S., Laury-Kleintop, L. & Gilmour, S.K. Suprabasal induction of ornithine decarboxylase in adult mouse skin is sufficient to activate keratinocytes. J Invest Dermatol 124, 602-614 (2005).
Lee, J., "Facile Preparation of Cyclopropylamines from Carboxamides," J. Org. Chem., 62: 1584-5 (1997).
Leveque, J. et al., "The Gastrointestinal Polyamine Source Depletion Enhances DFMO induced Polyamine Depletion in MCF-7 Human Breast Cancer Cells In Vivo," Anticancer Res, 18: 2663-3668 (1998).
Levin, V.A., Csejtey, J. & Byrd, D.J. Brain, CSF, and tumor pharmacokinetics of alpha-difluoromethylornithine in rats and dogs. Cancer Chemother Pharmacol 10, 196-199 (1983).
Li, Y. et al., "Comparative Molecular Field Analysis-Based Predictive Model of Structure-Function Relationships of Pilyamine Transport Inhibitors in L1210 Cells," Cancer Res, 57: 234-239 (1997).
Li, Y. et al., "Synthesis and Antitumor Evaluation of a Highly Potent Cytotoxic DNA Cross-Linking Polyamine Analogue, 1, 12-Diaziridinyl-4,9-diazadodecane," J. Med. Chem., 39: 339-41 (1996).
Liao, X., Liang, W., Wiedmann, T., Wattenberg, L. & Dahl, A. Lung distribution of the chemopreventive agent difluoromethylornithine (DFMO) following oral and inhalation delivery. Exp Lung Res 30, 755-769 (2004).
Libby, P.R., Henderson, M., Bergeron, R.J. & Porter, C.W. Major increases in spermidine/spermine-N1-acetyltransferase activity by spermine analogues and their relationship to polyamine depletion and growth inhibition in L1210 cells. Cancer Res 49, 6226-6231 (1989).
Linsalata, M., et al. Prognostic value of tissue polyamine levels in human colorectal carcinoma. Anticancer Res 22, 2465-2469 (2002).
Lipinski CA, et al. "Experimental and computational approaches to estimate solubility and permeability in drug discovery and development settings", Adv. Drug Deliv. Rev., 46(1-3):3-26 (2001).
Liu, L., et al. Polyamine-modulated expression of c-myc plays a critical role in stimulation of normal intestinal epithelial cell proliferation. Am J Physiol Cell Physiol 288, C89-99 (2005).

Lloyd-Williams, P., "Convergent Solid-Phase Peptide Synthesis," Tetrahedron, 49(48): 11065-133 (1993).
Loiseau, P.M., Czok, M., Chauffert, O., Bourass, J. & Letourneux, Y. Studies on lipidomimetic derivatives of alpha-difluoromethylornithine (DFMO) to enhance the bioavailability in a Trypanosoma B. brucei murine trypanosomiasis model. Parasite 5, 239-246 (1998).
Lowe, et al., "Antiinflammatory Drug Effects on Ultraviolet Light-Induced Epidermal Ornithine Decarboxylase and DNA Synthesis," The Journal of Investigative Dermatology, vol. 74, pp. 418-420 (1980).
Lu, J. Triethylenetetramine pharmacology and its clinical applications. Mol Cancer Ther 9, 2458-2467 (2010).
Luk, G.D., Goodwin, G., Marton, L.J. & Baylin, S.B. Polyamines are necessary for the survival of human small-cell lung carcinoma in culture. Proc Natl Acad Sci U S A 78, 2355-2358 (1981).
Maddox, A.M., Freireich, E.J., Keating, M.J., Frasier-Scott, K.F. & Haddox, M.K. Alterations in human circulating and bone marrow mononuclear cell polyamine levels in hematologic malignancies as a consequence of difluoromethylornithine administration. Invest New Drugs 6, 125-134 (1988).
Maddox, A.M., Keating, M.J., McCredie, K.E., Estey, E. & Freireich, E.J. Phase I evaluation of intravenous difluoromethylornithine—a polyamine inhibitor. Invest New Drugs 3, 287-292 (1985).
Maher, S. et al., "Safety and efficacy of sodium caprate in promoting oral drug absorption: from in vitro to the clinic," Advanced Drug Delivery and Reviews, Elsevier, vol. 61; No. 15; 1427-1499 (2009).
Maillard, L., et al., "Percutaneous Delivery of the Gax Gene Inhibits Vessel Stenosis in a rabbit Model of Balloon Angioplasty," Cardiovasc. Res., 35: 536-46 (1997).
Manni, A., Mauger, D., Gimotty, P. & Badger, B. Prognostic influence on survival of increased ornithine decarboxylase activity in human breast cancer. Clin Cancer Res 2, 1901-1906 (1996).
Marton, L.J., et al. The relationship of polyamines in cerebrospinal fluid to the presence of central nervous system tumors. Cancer Res 36, 973-977 (1976).
Marton, L.J., et al., "Polyamines as Targets for Therapeutic Intervention," Annu. Rev. Pharmacol. Toxicol., 35: 55-91 (1995).
Matsufuji, S. et al., "Reading Two Bases Twice: Mammalian Antizyme Frame Shifting in Yeast," EMBO Journal, 15: 1360-1370 (1996).
Matthews, H.R., "Polyamines, Chromatin Structure and Transcription," BioEssays, 15: 561-566 (1993).
McWilliams, M.L. et al., "Characterization of the Ototoxicity of Difluoromethylornithine and Its Enantiomers," Toxicological Sciences, vol. 56; 124-132 (2000).
Medina, C.B., et al. "Metabolites released from apoptotic cells act as tissue messengers", Nature 580, 130-135 (2020).
Melchiorre C. et al. "Polyamines in Drug Discovery: From the Universal Template Approach to the Multitarget-Directed Ligand Design Strategy", J. Med. Chem., 53:5906-5914 (2010).
Messenger, "The Control of Hair Growth: An Overview," The Society for Investigative Dermatology, vol. 101, No. 1, 4S-9S (1993).
Messing, E.M., et al. Low-dose difluoromethylornithine and polyamine levels in human prostate tissue. J Natl Cancer Inst 91, 1416-1417 (1999).
Metcalf, et al., "Catalytic Irreversible Inhibition of Mammalian Ornithine Decarboxylase (E.C. 4.1.1.17) by Substrate and Product Analogues," Journal of the American Chemical Society, vol. 100, No. 8, pp. 2331-2333 (1978).
Meyskens, F.L., Jr., et al. Difluoromethylornithine plus sulindac for the prevention of sporadic colorectal adenomas: a randomized placebo-controlled, double-blind trial. Cancer Prev Res (Phila) 1, 32-38 (2008).
Meyskens, F.L., Jr., et al. Dose de-escalation chemoprevention trial of alpha-difluoromethylornithine in patients with colon polyps. J Natl Cancer Inst 86, 1122-1130 (1994).
Meyskens, F.L., Jr., et al. Effect of alpha-difluoromethylornithine on rectal mucosal levels of polyamines in a randomized, double-blinded trial for colon cancer prevention. J Natl Cancer Inst 90, 1212-1218 (1998).
Milord, F., Loko, L., Ethier, L., Mpia, B. & Pepin, J. Eflornithine concentrations in serum and cerebrospinal fluid of 63 patients

(56) References Cited

OTHER PUBLICATIONS treated for Trypanosoma brucei gambiense sleeping sickness. Trans R Soc Trop Med Hyg 87, 473-477 (1993).
Minarini A. et al. "Synthetic polyamines activating autophagy: Effects on cancer cell death", European J. Medicinal Chem., 67:359-366 (2013).
Misquith, A., et al., "In vitro evaluation of TLR4 agonist activity: formulation effects," Colloids Surf B Biointerfaces 113, 312-319 (2014).
Mitchell, M.F., et al. Polyamine measurements in the uterine cervix. J Cell Biochem Suppl 28-29, 125-132 (1997).
Mitchell, M.F., et al., "Difluoromethylornithine (DFMO) treatment is Associated with Decreased CD Blood Vessel Counts in Cervical Intraepithelial Neoplasia (CIN)," Proceedings AACR, 39 (Abstract#600) :88 (1998).
Moulinoux, J.P. et al., "Biological Significance of Circulating Polyamines in Oncology," Cell Mal Biol, 37: 773-783 (1991).
Moulinoux, J.P. et al., "Inhibition of growth of the U-251 Human Glioblastoma in Nude Mice by Polyamine Deprivation," Anticancer Res, 11: 175-180 (1991).
Moya, E. et al., "Synthesis and Neuropharmacological properties of Arthropod Polyamine Amide Toxins," Neuropharmacology of Polyamines (Carter, C., ed.), Academic, San Diego, pp. 167-184 (1994).
Moyano, et al., "Inhibition of Omithine Decarbocylase by the Isomers of 1,4-dimethylputrescine," J. Med. Chem., vol. 33, No. 7, pp. 1969-1974 (1990).
Murakami, Y. et al., "Ornithine Decarboxylase Is Degraded be the 26S Proteasome Without Ubiquitination," Nature, 360: 597-599 (1992).
Muramoto, K., "Preparation and Characterization of Photoactivatable Heterobifunctional Fluorescent Reagents," Agric. Biol. Chem., 48(11): 2695-9 (1984).
Murray-Stewart T. et al. "The re-expression of the epigenetically silenced e-cadherin gene by a polyamine analogue lysine-specific demethylase=1 (LSD1) inhibitor in human acute myeloid leukemia cell lines", Amino Acids, 46(3):585-594 (2014).
Muth, A., et al. "Polyamine transport inhibitors: design, synthesis, and combination therapies with difluoromethylornithine", J Med Chem 57, 348-363 (2014).
Na-Bangchang, K., et al. The pharmacokinetics of eflornithine (alpha- difluoromethylornithine) in patients with late-stage T.b. gambiense sleeping sickness. Eur J Clin Pharmacol 60, 269-278 (2004).
Nagarajan, S., et al., "Chemistry of Naturally Occuring Polyamines. 10. Nonmetabolizable Derivatives of Spermine and Spermidine," J. Org. Chem., 51: 4856-61 (1986).
Nagarajan, S., et al., "Chemistry of Naturally Occurring Polyamines. II. Unsaturated Spermidine and Spermine Derivatives," J. Org. Chem., 52: 5044-6 (1987).
Nakanishi, et al., "Philantotoxin-433 (PhTX-433), a noncompetitive glutamate receptor inhibitor," Pure Appl. Chem., 62: 1223-1230 (1990).
Nakaoka, T., et al., "Inhibition of Rat Vascular Smooth Muscle Proliferation In Vitro and In Vivo by Bone Morphogenetic Protein-2," J. Clin. Invest., 100(11): 2824-32 (1997).
Nancarrow, et al., "Dynamic expression of omithine decarboxylase in hair growth," Mechanisms of Development, vol. 84, pp. 161-164 (1999).
Nesher, G. et al., "The In Vitro Effects of Methotrexate on Peripheral Blood Mononuclear Cells," Arthr. Rheumat., 33(7): 954-7 (1990).
Neubert, R. "Ion pair transport across membranes", Pharm Res 6(9), 743-747 (1989).
Neubert, R. et al., "Ion pair approach of ampicillin using in vitro methods", Pharm Acta Helv 65, 186-188 (1990).
Newton, G.L. et al., "Effect of Polyamine-Induced Compaction and Aggregation of DNA—A Major Factor in Radioprotection of Chromatin under Physiological Conditions," Radiation Research, 145: 776-80 (1996).
Nilam, M., et al. A Label-Free Continuous Fluorescence-Based Assay for Monitoring Ornithine Decarboxylase Activity with a Synthetic Putrescine Receptor. SLAS Discov 22, 906-914 (2017).
Nilsson, J.A., et al. Targeting ornithine decarboxylase in Myc-induced lymphomagenesis prevents tumor formation. Cancer Cell 7, 433-444 (2005).
Nilsson, J.L.G. et al., "Fibrin-Stabilizing Factor Inhibitors" Acta Pharmaceutica Suecica, 8(4): 497-504 (1971).
Nishiki, Y., et al. Characterization of a novel polyclonal anti-hypusine antibody. Springerplus 2, 421 (2013).
Non-Final Office Action for U.S. Appl. No. 16/823,150, "Bioavailable Polyamines" consisting of 39 pages. dated Sep. 7, 2021.
Non-Final Office Action for U.S. Appl. No. 11/050,789, titled: "Hydrophobic Polyamine Analogs And Methods For Their Use," dated Dec. 6, 2006.
Non-Final Office Action for U.S. Appl. No. 11/050,789, titled: "Hydrophobic Polyamine Analogs And Methods For Their Use," dated Jan. 4, 2008.
Non-Final Office Action for U.S. Appl. No. 11/062,481, titled: "Hydrophobic Polyamine Analogs And Methods For Their Use," dated Apr. 23, 2007.
Non-Final Office Action for U.S. Appl. No. 15/753,291, titled: "Bioavailable Polyamines," dated Apr. 30, 2019.
Notice of Allowance for U.S. Appl. No. 10/296,259, titled: "Hydrophobic Polyamine Analogs And Methods For Their Use," dated Sep. 28, 2004.
Notice of Allowance for U.S. Appl. No. 11/062,481, titled: "Hydrophobic Polyamine Analogs And Methods For Their Use," dated May 28, 2008.
Notice of Allowance for U.S. Appl. No. 13/047,297, titled: "Hydrophobic Polyamine Analogs And Methods For Their Use," dated Aug. 17, 2011.
Notice of Allowance for U.S. Appl. No. 13/047,297, titled: "Hydrophobic Polyamine Analogs And Methods For Their Use," dated Dec. 13, 2011.
Notice of Allowance for U.S. Appl. No. 15/753,291, titled: "Bioavailable Polyamines," dated Jan. 23, 2020.
O'Brien, T.G., "The induction of ornithine decarboxylase as an early, possibly obligatory, event in mouse skin carcinogenesis," Cancer Res 36, 2644-2653 (1976).
O'Brien, T.G., et al., "Ornithine decarboxylase overexpression is a sufficient condition for tumor promotion in mouse skin," Cancer Res 57, 2630-2637 (1997).
O'Brien, T.G., et al., Activation of mouse epidermal tumor ornithine decarboxylase by GTP: evidence for different catalytic forms of the enzyme. Proc Natl Acad Sci U S A 84, 8927-8931 (1987).
Origanti, S. et al., "Ras transformation of RIE-1 cells activates cap-independent translation of ornithine decarboxylase: regulation by the Raf/MEK/ERK and phosphatidylinositol 3-kinase pathways", Cancer Res 67, 4834-4842 (2007).
O'Sullivan MC et al. "Dibenzusuberyl substituted polyamines and analogs of clomipramine as effective inhibitors of trypanothione reductase; molecular docking, and assessment of trypanocidal activities", Bioorganic & Medicinal Chemistry, 23:996-1010 (2015).
Pan, X., et al. Cerebrospinal Fluid Spermidine, Glutamine and Putrescine Predict Postoperative Delirium Following Elective Orthopaedic Surgery. Sci Rep 9, 4191 (2019).
Parchment, R. E. et al., "Polyamine Oxidation, Programmed Cell Death, and Regulation of Melanoma in the Murine Embryonic Limb," Cancer Res., 49: 6680-6 (1989).
Pegg, A.E., et al., "Polyamines and neoplastic growth," Biochem Soc Trans 35, 295-299 (2007).
Pendyala, L., Creaven, P.J. & Porter, C.W. Urinary and erythrocyte polyamines during the evaluation of oral alpha-difluoromethylornithine in a phase I chemoprevention clinical trial. Cancer Epidemiol Biomarkers Prev 2, 235-241 (1993).
Peralta Soler, et al., "Modulation of Murine Hair Follicle Function by Alterations in Ornithine Decarboxylase Activity," The Society for Investigative Dermatology, vol. 106, No. 5, pp. 1108-1113 (1996).
Persson, L. et al., "Curative Effect of d, 1-2-Difluoromethylornithine on Mice Bearing Mutant L1210 Leukemia Cells Deficient in Polyamine Uptake," Cancer Res, 48: 4807-4811 (1998).

(56) References Cited

OTHER PUBLICATIONS

Pfitzner, K.E., et al., "Sulfoxide-Carbodiimide Reactions. I. A Facile Oxidation of Alcohols," J. Am. Chem. Soc., 87(24): 5661-9 (1965).
Pietilä, et al., "Activation of Polyamine Catabolismprofoundly Alters Tissue Polyamine Pools and Affects Hair Growth and Female Fertility in Transgenic Mice Overexpressing Spermidine/Spermine $N^1$-Acetyltransferase," The Journal of Biological Chemistry, vol. 272, No. 30, pp. 18746-18751 (1997).
Pietilä, et al., "Relation of Skin Polyamines to the Hairless Phenotype in Transgenic Mice Overexpressing Spermidine/Spermine $N^1$-Acetyltransferase," The Society for Investigative Dermatology, vol. 116, No. 5, pp. 801-805 (2001).
Pohjanpelto, P. "Putrescine Transport is Greatly Increased in Human Fibroblasts Initiated to Prolifarete," J Cell Biol, 68: 512-520 (1976).
Porter, C.W. et al., "Aliphatic Chain Length Specificity of the Polyamine Transport System in Ascites L1210 Leukemia Cells," J Cancer Res, 44: 126-128 (1984).
Porter, C.W., et al., "Antitumor Activity of $N^1$, $N^{11}$-Bis(ethyl)norspermine against Human Melanoma Xenografts and Possible Biochemical Correlates of Drug Action," Cancer Res., 53: 581-6 (1993).
Poulin, R., Lu, L., Ackermann, B., Bey, P. & Pegg, A.E. Mechanism of the irreversible inactivation of mouse ornithine decarboxylase by alpha-difluoromethylornithine. Characterization of sequences at the inhibitor and coenzyme binding sites. J Biol Chem 267, 150-158 (1992).
Probst et al., "Ornithine decarboxylase activity in relation to DNA synthesis in mouse interfollicular epidermis and hair follicles," Biochim Biophys Acta, vol. 407, No. 2, pp. 147-157 (1975).
Puleston, D.J., et al. Polyamines and eIF5A Hypusination Modulate Mitochondrial Respiration and Macrophage Activation. Cell Metab 30, 352-363 e358 (2019).
Qarawi, M. et al. "Optimization of the MMT Assay for B16 Murine Melanoma Cells and CE Its Application in Assessing Growth Inhibition by Polyamines and Novel Polyamine Conjugates," Pharm Sci., vol. 3, (5/6): 235-239 (1997).
Quemener, V. et al., "Polyamine Deprivation Enhances Antitumoral Efficacy of Chemotherapy," Anticancer Res, 12: 1447-1454 (1992).
Quemener, V. et al., "Polyamine Deprivation: A New Tool in Cancer Treatment," Anticancer Res., 14: 443-8 (1994).
Raditsch, M. et al., "Polyamine Spider Toxins and Mammalian N-Methyl-D-Aspartate Receptors. Structural Basis for Chemical Blocking and Binding of Argiotoxin 636," Eur J Biochem, 240: 416-426 (1996).
Raines, D. E., et al., "Potential-Dependent Phase Partitioning of Fluorescent Hydrophobic Ions in Phospholipid Vesicles," J. Membrane Biol., 82: 241-7 (1984).
Rajeev, K.G., et al., "Conformationally Restrained Chiral Analogues of Spermine: Chemical Synthesis and Improvements in DNA Triplex Stability," J. Org. Chem., 62: 5169-73 (1997).
Ranganathan, R. S., et al., "Novel Analogues of Nucleoside 3',5'-Cyclic Phosphates. I. 5'- Mono-and Dimethyl Analogs of Adenosine 3',5'-Cyclic Phosphate," J. Org. Chem., 39(3): 290-8 (1974).
Ransom, R.W et al., "Cooperative Modulation of [$^3$H]MK-801 Binding to the N-Methyl-D-Aspartate Receptor-Ion Channel Complex by L-Glutamate, Cycline, and Polyamines," J Neurochem, 51: 830-836 (1988).
Ray, R.M., Bhattacharya, S., Bavaria, M.N., Viar, M.J. & Johnson, L.R. Spermidine, a sensor for antizyme 1 expression regulates intracellular polyamine homeostasis. Amino Acids 46, 2005-2013 (2014).
Relyea et al., "Potent Inhibition of Ornithine Decarboxylase by β, γ Unsaturated Substrate Analogs," Biochemical and Biophysical Research Communications, vol. 67, No. 1, pp. 392-402 (1975).
Rink, H., "Solid-Phase Synthesis of Protected Peptide Fragments Using a Trialkoxy-Diphenyl-Methylester Resin," Tetrahed. Lett., 28(33): 3787-90 (1987).
Romijn, J.C., et al., "Problems of pharmacokinetic studies on alpha-difluoromethylornithine in mice," Cancer Chemother Pharmacol 19, 30-34 (1987).

Rossi T. et al. "Mepacrine Antagonises Tumour Cell Growth Induced by Natural Polyamines", Anticancer Research, 28:2765-2768 (2008).
Russell, D. et al., "Amine Synthesis in Rapidly Growing Systems: Ortithine Decarboxylase Activity in Generating Rat Liver, Chick Embryos, and Various Tumors," Proc Natl Acad Sci USA, 60(4): 1420-1427 (1968).
Saiki R. et al. "In Vitro and in vivo evaluation of polymethylene tetraamine derivatives as NMDA receptor channel blockers", Bioorganic & Medicinal Chem. Letters, 23:3901-3904 (2013).
Salemme, F.R., et al., "Serendipity Meets Precision: The Integration of Structure-Based Drug Design and Combinatorial Chemistry for Efficient Drug Discovery," Structure, 5(3): 319-24 (1997).
Samal, K. et al., "AMXT-1501, a novel polyamine transport inhibitor, synergizes with DFMO in inhibiting neuroblastoma cell proliferation by targeting both ornithine decarboxylase and polyamine transport," International Journal of Cancer, vol. 133; 1323-1334 (2013).
Sarhan, S. et al., "The Gastrointestial Tract as Polyamine Source for Tumor Growth," Anticancer Res, 9: 215-224 (1989).
Sasaki, Y. et al., "Solid-Phase Synthesis and Biological Properties of .psi.[$CH_2NH$] Pseudopeptide Analogues of a Highly Potent Somatostatin Octapeptide," J. Med. Chem., 30(7): 1162-6 (1987).
Saulnier Sholler, G.L., et al. ", Phase I Trial of DFMO Targeting Polyamine Addiction in Patients with Relapsed/Refractory Neuroblastoma", PLoS One 10, e0127246 (2015).
Scalabrino, G. et al., "Polyamines in Mammalian Tumors. Part I," Adv Cancer Res, 35:151-268 (1981).
Scalabrino, G. et al., "Polyamines in Mammalian Tumors. Part II," Adv Cancer Res, 36:1-102 (1982).
Scalabrino, G., et al. Levels of activity of the polyamine biosynthetic decarboxylases as indicators of degree of malignancy of human cutaneous epitheliomas. J Invest Dermatol 74, 122-124 (1980).
Schallenberg, E. E., et al., "Ethyl Thioltrifluoroacetate As An Acetylating Agent with Particular Reference to Peptide Synthesis," J. Am. Chem. Soc., 77: 2779-83 (1955).
Schechter, P.J. et al., "Clinical Aspects of Inhibition of Ornithine Decarboxylase with Emphasis on Therapeutic Trials of Eflornithine (DFMO) in Cancer and Protozoan Diseases," Inhibition of Polyamine Metabolism. Biological Significance and Basis for New Therapies, Mccann, P.P. et al., eds; pp. 345-364 (1987).
Schultheiss, N. et al., "Pharmaceutical Cocrystals and Their Physicochemical Properties", Cryst Growth Des 9, 2950-2967 (2009).
Seiler N., et al., "Polyamines and apoptosis", J. Cell. Mal. Med. 9(3):623-642 (2005).
Seiler, N. et al., "Polyamine Transport in Mammalian Cells," Int J Biochem, 22: 211-218 (1990).
Seiler, N. et al., "Polyamine Transport in Mammalian Cells. An update," Int J Biochem, 28(8): 843-861 (1996).
Seiler, N., "Functions of Polyamine Acetylation," Can Pharmacol, 65: 2024-2035 (1987).
Seiler, N., "Polyamine Oxidase, Properties and Functions," Progress in Brain Res, 106: 333-344 (1995).
Senanayake T. et al. "Design of polyamine-based therapeutic agents: new targets and new directions", Essay Biochem., 46:77-94 (2013).
Seppanen, P. "Some properties of the polyamine deprivation-inducible uptake system for methylglyoxal bis(guanylhydrazone) in tumor cells", Acta Chem Scand B 35, 731-736 (1981).
Shirahata et al., "Effects of Inhibitors of Spermidine Synthase and Spermine Synthase on Polyamine Synthesis in Rat Tissues," Biochemical Pharmacology, vol. 45, No. 9, pp. 1897-1903 (1993).
Shirahata et al., "Putrescine or Spermidine Binding Site of Aminopropyltransferases and Competitive Inhibitors," Biochemical Pharmacology, vol. 41 No. 2, pp. 205-212 (1991).
Shyng, S.-L., et al., "Depletion of Intercellular Polyamines Relieves Inward Rectification of Potassium Channels," Proc. Natl. Acad. Sci. USA., 93: 12014-9 (1996).
Siegel, M.G. et al., "Rapid Purification of Small Molecule Libraries by Ion Exchange Chromatography," Tetrahedron Lett., 38(19): 3357-60 (1997).
Singh, S. et al., "Characterization of Simian Malarial Parasite (Plasmodium Knowlesi)-induced Putrescine Transport in Rhesus Monkey Erythrocytes," J. Biol. Chem., 272(21): 13506-11 (1997).

(56) References Cited

OTHER PUBLICATIONS

Siu, L.L., et al. A phase I and pharmacokinetic study of SAM486A, a novel polyamine biosynthesis inhibitor, administered on a daily-times-five every-three-week schedule in patients with Advanced solid malignancies. Clin Cancer Res 8, 2157-2166 (2002).
Slocum, R.D., Bitonti, A.J., McCann, P.P. & Feirer, R.P. DL-alpha-difluoromethyl[3,4-3H]arginine metabolism in tobacco and mammalian cells. Inhibition of ornithine decarboxylase activity after arginase-mediated hydrolysis of DL-alpha-difluoromethylarginine to DL-alpha-difluoromethylornithine. Biochem J 255, 197-202 (1988).
Smith, M.K., et al., "Co-operation between follicular ornithine decarboxylase and v-Ha-ras induces spontaneous papillomas and malignant conversion in transgenic skin," Carcinogenesis 19, 1409-1415 (1998).
Smithson, D.C., et al., Optimization of a non-radioactive high-throughput assay for decarboxylase enzymes. Assay Drug Dev Technol 8, 175-185 (2010).
Soda, K. The mechanisms by which polyamines accelerate tumor spread. J Exp Clin Cancer Res 30, 95 (2011).
Solano et al., "Kinetic Study of the Inhibition of Rat Liver Ornithine Decarboxylase by Diamines: Considerations on the Mechanism of Interaction Between Enzyme and Inhibitor," Int. J. Biochem., vol. 20, No. 4, pp. 463-470 (1988).
Sosnovsky, G. et al., B: Chem. Sci., vol. 49, No. 11, pp. 1580-1585 (1994).
Stabellini et al., Exogenous Spermidine Modulates Glycosaminoglycan Accumulation and Epithelial Differentiation in Chick Embryonic Skin, The Journal of Experimental Zoology, vol. 281, pp. 594-601 (1998).
Stanek, J., et al. "4-Amidinoindan-1-one 2'-amidinohydrazone: a new potent and selective inhibitor of S-Adenosylmethionine decarboxylase", J Med Chem 36, 2168-2171 (1993).
Sugiyama, S. et al., "Crystal Structure of PotD, the Primary Receptor of the Polyamine Transport System in *Escherichia coli*," J Biol Chem, 271: 9519-9525 (1996).
Suli-Vargha, H., et al. In vitro cytotoxic effect of difluoromethylornithine increased nonspecifically by peptide coupling. J Pharm Sci 86, 997-1000 (1997).
Susskind, B.M. et al., "Inhibition of cytolytic T lymphocyte maturation with ornithine, arginine, and putrescine", Journal of Immunology, 139:905-912 (1987).
Suzuki, T. et al., "Antizyme Protects Against Abnormal Accumulation and Toxicity of Polyamines in Ornithine Decarboxylase-Overproducing Cells," Proc Natl Acad Sci USA, 91: 8930-4 (1994).
Szabo, C., et al. "The mechanism of the inhibitory effect of polyamines on the induction of nitric oxide synthase: role of aldehyde metabolites", Br. J. Pharmacol., 113:757-766 (1994).
Tabor, H. et al., "1,4-Diaminobutrane (putrescine), Spermidine, and Spermine," Ann Rev Biochem, 45: 285-306 (1976).
Takagi, M.M. et al., "The Watanabe Heritable Hyperlipidemic Rabbit Is A Suitable Experimental Model to Study Differences in Tissue Response Between Intimal and Medial Injury After Balloon Angioplasty," Arterioscler. Thromb. Vasc. Biol., 17(12): 3611-9 (1997).
Tao, L., et al. CHAF1A Blocks Neuronal Differentiation and Promotes Neuroblastoma Oncogenesis via Metabolic Reprogramming. Adv Sci (Weinh), e2005047 (2021).
Thompson, L.A. et al., "Straightforward and General Method for Coupling Alcohols to Solid Supports," Tetrahed. Lett., 35: 9333-6 (1994).
Thompson, P.A., et al. Levels of rectal mucosal polyamines and prostaglandin E2 predict ability of DFMO and sulindac to prevent colorectal adenoma. Gastroenterology 139, 797-805, 805 e791 (2010).
Tierny, D., et al. Phase I Clinical Pharmacology Study of F14512, a New Polyamine-Vectorized Anticancer Drug, in Naturally Occurring Canine Lymphoma. Clin Cancer Res 21, 5314-5323 (2015).
Tomasi, S., et al., "Solid phase organic synthesis of polyamine derivatives and initial biological evaluation of their antitumoral activity," Bioorganic & Medicinal Chemistry Letters, 8: 635-640 (1998).
Tomitori, H. et al., "Identification of a Gene for a Polyamine Transport Protein in Yeast," J Biol Chem, 274: 3265-3267 (1999).
Tortora, G. et al., "Synergistic Inhibition of Growth and Induction of Apoptosis by 8-ChlorocAMP and Paclitaxel or Cisplatin in Human Cancer Cells," Cancer Res., 57: 5107-11 (1997).
Trikha, et al., "Nitroglycerin: a NO donor inhibits TPA-mediated tumor promotion in murine skin," Carcinogenesis, vol. 22, No. 8, pp. 1207-1211 (2001).
Tsubokawa, H. et al., "Effects of a Spider Toxin and Its Analogue on Glutamate-Activated Currents in the Nippocampal CA1 Neuron after Ischemia," J Neurophys, 74: 218-225 (1995).
Valerio, R.M. et al., "Multiple Peptide Synthesis on Acid-Labile Handle Derivatized Polvethylene Supports," Int. J. Peptide Protein Res., 44:158-65 (1994).
Ventura, C. et al., "Polyamine Effects on $[Ca^{2+}]i$ Homeostasis Contractility in Isolated Rat Ventricular Carciomyocytes," Am. J. Physiol., 267: H587-H592 (1994).
Verlinden BK et al. "Interrogating alkyl and arylalkylpolyamino (bis)urea and (bis)thiourea isosteres as potent antimalarial chemotypes against multiple lifecycle forms of Plasmodium falciparum parasites", Bioorganic & Medicinal Chemistry, 23:5131-5143 (2015).
Veznik, F. et al., "Synthese van N1 ,4-Di(p-cumaroyl)spermin, einem moglichen Bioaenese-Vorlaufer van Aohelandrin," Helvetica Chimica Acta, 74: 654-661 (1991).
Vig, B.S., Huttunen, K.M., Laine, K. & Rautio, J. Amino acids as promoieties in prodrug design and development. Adv Drug Deliv Rev 65, 1370-1385 (2013).
Volkow, N. et al., "Labeled Putrescine as a Probe in Brain Tumors," Science, 221: 673-675 (1983).
Walters, D.L. et al., "A Comparison of Fluorescence Versus Chemiluminescence Detection for Analysis of the Fluorescamine Derivative of Histamine by HPLC," Biomed. Chromatogr., 8: 207-11 (1994).
Wang, S.-S., "p-Alkoxybenzyl Alcohol Resin and p-Alkoxybenzyloxycarbonylhydrazide Resin for Solid Phase Synthesis of Protected Peptide Fragments," J. Am. Chem. Soc., 95(4): 1128-1333 (1973).
Wanzlick, H.W. et al., "1.2-Dianilino-athan als Aldehydreagens," Chem. Ber., 86: 1463-6 (1953).
Warrell, R.P., et al., "Sequential inhibition of polyamine synthesis. A phase I trial of DFMO (alpha-difluoromethylornithine) and methyl-GAG [methylglyoxal-bis(guanylhydrazone)]", Cancer Chemother Pharmacol 11, 134-136 (1983).
Webb, H.K. et al., "1-(N-Alkylamino)-11-(N-Ethylamino)-4,8-Diazaundecanes: Simple Synthetic Polyamine Analogues That Differentially Alter Tublin Polymerization," J. Med Chem, 42(8): 1415-21 (1999).
Weekes, et al., "Inhibition by Putrescine of the Induction of Epidermal Ornithine Decarboxylase Activity and Tumor Promotion Caused by 12-O-Tetradecanoylphorbol-13-acetate," Cancer Research, vol. 40, pp. 4013-4018 (1980).
Weiss, W.A., et al., "Targeted expression of MYCN causes neuroblastoma in transgenic mice," EMBO J 16, 2985-2995 (1997).
Wilding, G., et al. Phase I trial of the polyamine analog N1,N14-diethylhomospermine (DEHSPM) in patients with advanced solid tumors. Invest New Drugs 22, 131-138 (2004).
Williams, K. et al., "Minireview: Modulation of the NMDA Receptor by Polyamines," Life Science, 48: 469-498 (1991).
Williams, K., "Interaction of Polyamines with Ion Channels," Biochem J, 325: 289-297 (1997).
Williams-Ashman, H.G. & Schenone, A. Methyl glyoxal bis(guanylhydrazone) as a potent inhibitor of mammalian and yeast S-adenosylmethionine decarboxylases. Biochem Biophys Res Commun 46, 288-295 (1972).
Wolff, A.C., et al., "A Phase II study of the polyamine analog N1,N11-diethylnorspermine (DENSpm) daily for five days every 21 days in patients with previously treated metastatic breast cancer," Clin Cancer Res 9, 5922-5928 (2003).

(56) References Cited

OTHER PUBLICATIONS

Wolff, J., "Promotion of Microtubule Assembly by Oligocations: Cooperatively between Charged Groups," Biochemistry, 37: 10722-10729 (1998).
Xia, C.Q. et al., "QSAR Analysis of Polyamine Transport Inhibitors in L1210 Cells," J. Drug. Target., 6: 65-77 (1998).
Yoneda et al., "Synthesis of polyamine derivatives having non-hypotensive $Ca^{2+}$-permeable AMPA receptor antagonist activity," Bioorganic & Medicinal Chemistry Letters, 11 :1261-1264 (2001).
Young et al., "U.v. wavelength dependence for the induction of ornithine decarbocylase activity in hairless mouse epidermis," Carcinogenesis, vol. 7, No. 4, pp. 601-604 (1986).
Yuan, Z.-M., et al., Proceedings of the American Association for Cancer Research, 34(Abstract #2264):380 (1993).
Zaitseva, M., et al. Use of human MonoMac6 cells for development of in vitro assay predictive of adjuvant safety in vivo. Vaccine 30, 4859-4865 (2012).
Zawia, N.H., Mattia, C.J. & Bondy, S.C. Differential effects of difluoromethylornithine on basal and induced activity of cerebral ornithine decarboxylase and mRNA. Neuropharmacology 30, 337-343 (1991).
Zhai, Q., et al. Structural Analysis and Optimization of Context-Independent Anti-Hypusine Antibodies. J Mol Biol 428, 603-617 (2016).
Zhang X. et al. "Design, synthesis and evaluation of genistein-polyamine conjugates as multi-functional anti-Alzheimer agents", Acta Pharmaceutica Sinica B, 5(1):67-73 (2015).
Zhang, L., Sui, C., Yang, W. & Luo, Q. Amino acid transporters: Emerging roles in drug delivery for tumor-targeting therapy. Asian J Pharm Sci 15, 192-206 (2020).
Zhang, M., et al. "Spermine inhibition of monocyte activation and inflammation", Mal. Med., 5:595-605 (1999).
Zhang, M., et al. Spermine inhibits proinflammatory cytokine synthesis in human mononuclear cells: a counterregulatory mechanism that restrains the immune response. J Exp Med 185, 1759-1768 (1997).
Zini M. et al. "Cytotoxicity of methoctramine and methoctramine-related polyamines", Chemico-Biological Interactions, 181:409-416 (2009).
DiGiovanni J. "Multistage carcinogenesis in mouse skin" . Pharmacol Ther 54, 63-128 (1992).
International Search Report and Written Opinion received for PCT Patent Application No. PCT/US2022/080619, dated Mar. 15, 2023, 9 pages.
Khan et al., "Dual targeting of polyamine synthesis and uptake in diffuse intrinsic pontine gliomas", Nature Communication, vol. 12, No. 971, 2021, 13 pages.
Maryam Karimi-Jafari et al: "Creating Cocrystals: A Review of Pharmaceutical Cocrystal Preparation Routes and Applications", Crystal Growth & Design, vol. 18, No. i0, Oct. 3, 2018 (Oct. 3, 2018), pp. 6370-6387.

Notice of Allowance for U.S. Appl. No. 16/823,150, "Bioavailable Polyamines" ated Mar. 21, 2022.
Notification of Transmittal of The International Search Report and the Written Opinion of the International Searching Authority, or the Declaration for International Application No. PCT/US2021/052788, "Combination Drug Substance of Polyamine Transport Inhibitor and DFMO" dated Jan. 28, 2022.
Wharf Canary: "Reflection paper on the use of cocrystals of active substances in medicinal products", May 21, 2015 (May 21, 2015).
Janda, K.D. et al., "Combinatorial Chemistry: A Liquid-Phase Approach," Meth. Enzymol., 267: 234-47 (1996).
Janne, J. et al., "Polyamines in Rapid Growth and Cancer," Biochim Biophys Acta 4 73: 241-293 (1978).
Janne, J. et al., Mammalian ornithine decarboxylase: activation and alteration of physical behaviour by thiol compounds. Biochem J 119, 595-597 (1970).
Janne, J., et al., On the purification of L-ornithine decarboxylase from rat prostate and effects of thiol compounds on the enzyme. J Biol Chem 246, 1725-1732 (1971).
Jasnis, M.A. et al., "Polyamines Prevent DFMO-Mediated Inhibition of Angiogenesis," Cancer Lett., 79: 39-43 (1994).
Kahana, et al., "Isolation of cloned cDNA encoding mammalian ornithine decarboxylase," Proc. Natl. Acad. Sci. USA, vol. 81, pp. 3645-3649 (1984).
Kaiser, E. et al., "Color Test for Detection of Free Terminal Amino Groups in the Solid-Phase Synthesis of Peptides," Anal. Biochem., 34(2): 595-8 (1970).
Kakinuma, Y. et al., "Cloning of the Gene Encoding a Putative Serine/Threonine Protein Kinase Which Enhances Spermine Uptake In *Saccharomyces cerevisiae*," Biochem. Biophys. Res. Comm., 216(3): 985-92 (1995).
Kano, Y., et al. Increased blood spermine levels decrease the cytotoxic activity of lymphokine-activated killer cells: a novel mechanism of cancer evasion. Cancer Immunol Immunother 56, 771-781 (2007).
Kanth, J.V.B., et al., "Selective Reduction of Carboxylic Acids into Alcohols Using $NaBH_4$ and $I_2$," J. Org. Chem., 56: 5964-5 (1991).
Karahalios, P. et al., "The Effect of Acylated Polyamine Derivative on Polyamine Uptake Mechanism, Cell Growth, and Polyamine Pools in *Escherichia coli*, and the Pursuit of Structure/Activity Relationships," Eur. J. Biochem., 251: 998-1004 (1998).
Kashiwagi, K. et al., "Isolation of Polyamine Transport-Deficient Mutants of *Escherichia coli* and Cloning of the Genes for Polyamine Transport Proteins," J Biol. Chem, 265: 20893-20897 (1990).
Kaur N. et al. "Designing the Polyamine Pharmacophore: Influence of N-Substituents on the Transport Behavior of Polyamine Conjugates", J. Med. Chem., 51:2551-2560 (2008).
Kendrick et al., "2,2-Difluoro-5-hexyne-1,4-diamine: A Potent Enzyme-Activated Inhibitor of Ornithine Decarbocylase," J. Med. Chem., vol. 32, pp. 170-173 (1989).

\* cited by examiner

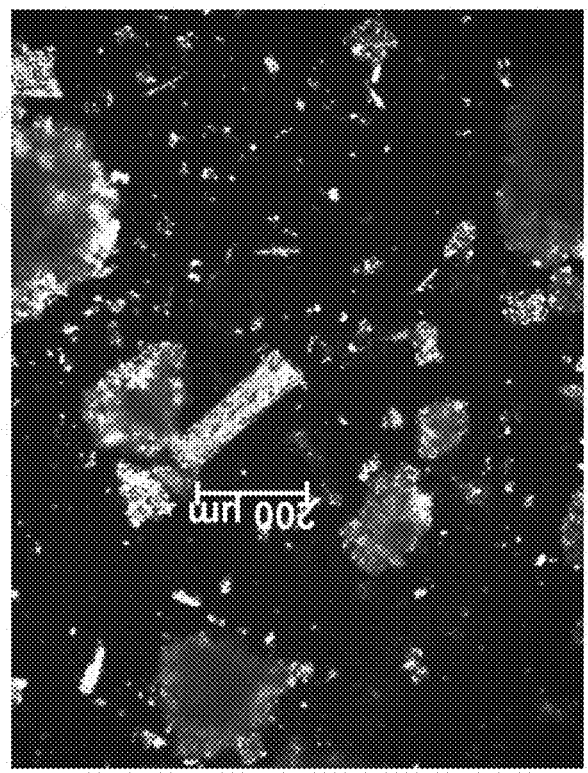
FIG. 6B Polarized Light Microscopy Imaging 10X
FIG. 6A Bright Field Microscopy Imaging 10X

COMBINATION DRUG SUBSTANCE OF POLYAMINE TRANSPORT INHIBITOR AND DFMO

RELATED APPLICATION

This application claims the benefit of U.S. Provisional Application No. 63/085,510, filed on Sep. 30, 2020. The entire teachings of this application are incorporated herein by reference.

BACKGROUND

Although combination drug therapy has a robust history for several important clinical applications, including antibiotic treatments, antiviral treatments and oncology therapeutics, combination drug therapy involving two drugs that target the same biological pathway is rarer. AMXT 1501 and difluoromethylornithine (DFMO) both target the polyamine metabolic pathway for the treatment of cancer.

Pharmaceutics is the scientific and technical field that aims to improve dose forms. One goal is to optimize dose forms that provide durable and potent engagement of biological targets over the desired treatment period. Additional goals are to provide dose products that have higher stability, more convenient handling properties, more convenient patient dosing scheduling and, especially for drug combinations, more consistent dosing of exact quantities and ratios of drug agents. AMXT 1501 and DFMO are currently administered separately.

Accordingly, there is a need for combination dosage forms of AMXT 1501 and DFMO.

SUMMARY

Provided herein is a combination (e.g., a combination dosage form) comprising difluoromethylornithine (DFMO), or an ionic form thereof, and a compound of the following structural formula:

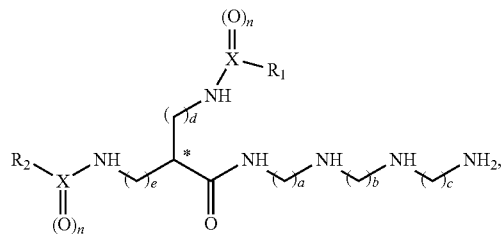

or a protonated form thereof, wherein values for the variables (e.g., a, b, c, d, e, n, $R_1$, $R_2$, X) are as described herein.

Also provided herein is a solid form (e.g., a crystalline solid form) comprising DFMO, or an ionic form thereof, and a compound of structural formula I, or a protonated form thereof, wherein values for the variables (e.g., a, b, c, d, e, n, $R_1$, $R_2$, X) are as described herein.

Also provided herein is a pharmaceutical composition comprising a combination or solid form (e.g., solid form) described herein, and a pharmaceutically acceptable excipient.

Also provided herein is a method of treating a cancer in a subject in need thereof, comprising administering to the subject a therapeutically effective amount of a combination, solid form or pharmaceutical composition described herein.

Also provided herein is a combination, solid form or pharmaceutical composition described herein for use in treating a cancer. Also provided herein is use of a combination, solid form or pharmaceutical composition described herein for the manufacture of a medicament for the treatment of a cancer.

The AMXT 1501-DFMO solid forms described herein have greatly increased melting point properties in comparison to their individual components. In addition, the combinations and solid forms provided herein are expected to provide one or more of the following advantages: (i) ion-pairing of AMXT 1501 with DFMO may enhance drug bioavailability, tissue and/or tumor targeting and/or pharmacokinetic activity against tumors; (ii) combination of two agents into one solid form may improve patient compliance; (iii) combination of two agents into one solid form may improve drug product handling and production feasibility; and (iv) combination of two agents into one solid form may reduce pill burden.

BRIEF DESCRIPTION OF THE DRAWINGS

The foregoing will be apparent from the following more particular description of example embodiments.

FIG. 6A is a bright-field image, and shows the results of polarized light microscopy (PLM) analysis of Lot 4-138.

FIG. 6B is a polarized light image, and shows the results of PLM analysis of Lot 4-138.

DETAILED DESCRIPTION

Figure 1A:
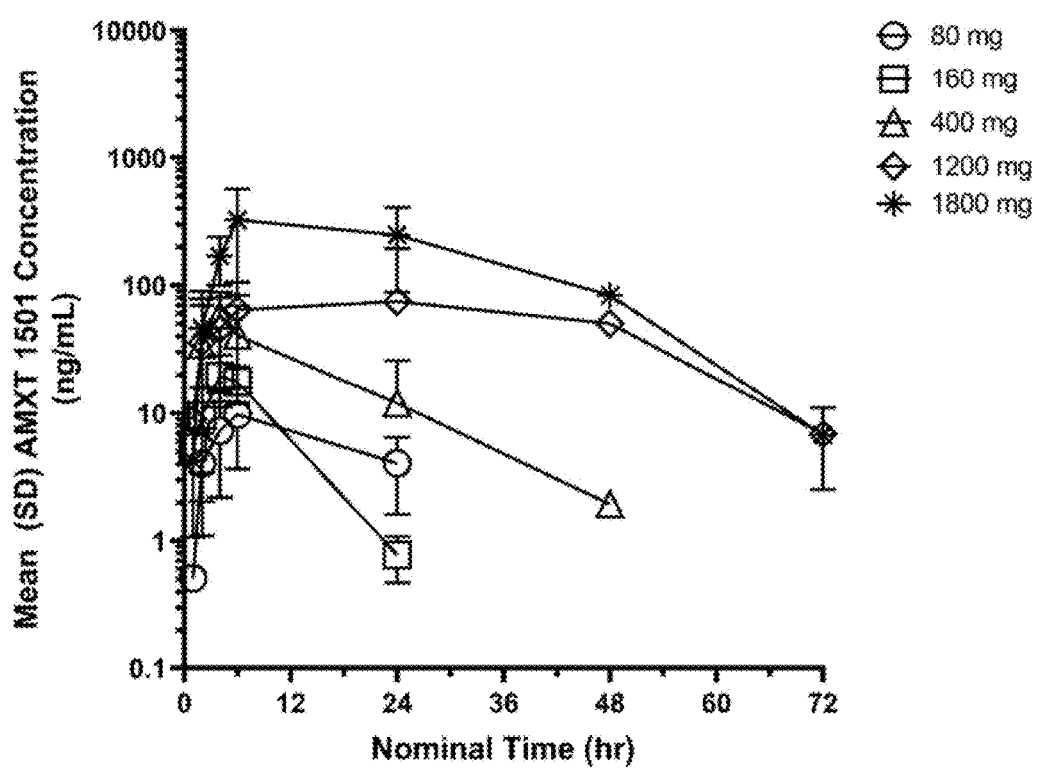
FIG. 1A is a mean plasma concentration versus time profile, and shows the mean plasma concentration of AMXT 1501 after a single dose (Day 1).

A description of example embodiments follows.

Definitions

As used in this specification and the appended claims, the singular forms "a," "an," and "the" include plural referents, unless the content and context clearly dictates otherwise.

Unless the context requires otherwise, throughout the specification and claims that follow, the word "comprise" and synonyms and variants thereof such as "have" and "include", as well as variations thereof, such as "comprises" and "comprising", are to be construed in an open, inclusive sense, e.g., "including, but not limited to."

"About" means within an acceptable error range for the particular value, as determined by one of ordinary skill in the art. Typically, an acceptable error range for a particular value depends, at least in part, on how the value is measured or determined, e.g., the limitations of the measurement system. For example, "about" can mean within an acceptable standard deviation, per the practice in the art. Alternatively, "about" can mean a range of ±20%, ±10%, ±5% or ±1% of a given value. It is to be understood that the term "about" can precede any particular value specified herein, except for particular values used in the Examples.

"Alicyclic" refers to a non-aromatic, cyclic, hydrocarbon radical having the specified number of carbon atoms. Thus, "(C$_1$-C$_{10}$)alicyclic" refers to an alicyclic radical having from 1-10 carbon atoms. In some embodiments, alicyclic is (C$_1$-C$_{25}$)alicyclic, e.g., (C$_1$-C$_{20}$)alicyclic, (C$_1$-C$_{15}$)alicyclic, (C$_1$-C$_{10}$)alicyclic, (C$_1$-C$_6$)alicyclic or (C$_1$-C$_5$)alicyclic. "Alicyclic" can be saturated, or contain one or more units of unsaturation (e.g., carbon-carbon double bonds). Examples of alicyclic include cycloalkyl, cycloalkenyl and cycloalkynyl. In some embodiments, alicyclic is saturated alicyclic. Examples of alicyclic include cyclopentyl, cyclopentenyl, cyclohexyl, cyclohexenyl, cycloheptyl, cyclooctyl, etc.

"Aliphatic" refers to a non-aromatic, branched- or straight-chain, hydrocarbon radical having the specified number of carbon atoms. Thus, "(C$_1$-C$_{15}$)aliphatic" refers to an aliphatic radical having from 1-15 carbon atoms. In some embodiments, aliphatic is (C$_1$-C$_{50}$)aliphatic, e.g., (C$_1$-C$_{25}$) aliphatic, (C$_1$-C$_{15}$)aliphatic, (C$_1$-C$_{10}$)aliphatic, (C$_1$-C$_5$)aliphatic or (C$_1$-C$_3$)aliphatic. "Aliphatic" can be saturated, or contain one or more units of unsaturation (e.g., carbon-carbon double bonds). Examples of aliphatic include alkyl, alkenyl and alkynyl. In some embodiments, aliphatic is saturated aliphatic, for example, (C$_1$-C$_{25}$)saturated aliphatic, (C$_1$-C$_{15}$)saturated aliphatic, (C$_1$-C$_{10}$)saturated aliphatic or (C$_1$-C$_5$)saturated aliphatic. In some embodiments, aliphatic is alkyl or alkenyl. In some embodiments, aliphatic is alkyl.

"Alkyl" refers to a saturated, branched- or straight-chain, aliphatic radical. "(C$_1$-C$_{15}$)Alkyl" refers to a radical having from 1-15 carbon atoms in a branched or linear arrangement. In some embodiments, alkyl is (C$_1$-C$_{50}$)alkyl, e.g., (C$_1$-C$_{25}$)alkyl, (C$_1$-C$_{15}$)alkyl, (C$_1$-C$_{10}$)alkyl, (C$_1$-C$_5$)alkyl or (C$_1$-C$_3$) alkyl. Examples of alkyl groups include methyl, ethyl, n-propyl, isopropyl, n-butyl, isobutyl, sec-butyl, t-butyl, n-pentyl, isopentyl, neopentyl, 2-methylpentyl, hexyl (e.g., n-hexyl), heptyl (e.g., n-heptyl), octyl (e.g., n-octyl), nonyl (e.g., n-nonyl), decyl (e.g., n-decyl), undecyl (e.g., n-undecyl), dodecyl (e.g., n-dodecyl), tridecyl (e.g., n-tridecyl), tetradecyl (e.g., n-tetradecyl), pentadecyl (e.g., n-pentadecyl), and the like.

"Alkenyl" refers to a branched- or straight-chain, aliphatic radical having at least one (e.g., one, two, three, four, five, etc.) carbon-carbon double bond. "(C$_1$-C$_{15}$)Alkenyl" refers to a radical having from 1-15 carbon atoms and at least one carbon-carbon double bond in a branched or linear arrangement. In some embodiments, alkenyl is (C$_1$-C$_{50}$) alkenyl, e.g., (C$_1$-C$_{25}$)alkenyl, (C$_1$-C$_{15}$)alkenyl, (C$_1$-C$_{10}$) alkenyl, (C$_1$-C$_5$)alkenyl or (C$_1$-C$_3$)alkenyl. Examples of alkenyl groups include vinyl, allyl, and the like.

"Alkoxy" refers to an alkyl radical attached through an oxygen linking atom, wherein alkyl is as described herein. Examples of alkoxy include, but are not limited to, methoxy, ethoxy, propoxy, isopropoxy, and the like.

"Alkynyl" refers to a branched- or straight-chain, aliphatic radical having at least one (e.g., one, two, three, four, five, etc.) carbon-carbon triple bond. "(C$_1$-C$_{15}$)Alkynyl" refers to a radical having from 1-15 carbon atoms and at least one carbon-carbon triple bond in a branched or linear arrangement. In some embodiments, alkynyl is (C$_1$-C$_{50}$) alkynyl, e.g., (C$_1$-C$_{25}$)alkynyl, (C$_1$-C$_{15}$)alkynyl, (C$_1$-C$_{10}$) alkynyl, (C$_1$-C$_5$)alkynyl or (C$_1$-C$_3$)alkynyl. Examples of alkynyl groups include propargyl, and the like.

"Aryl" refers to a monocyclic or polycyclic (e.g., bicyclic, tricyclic), carbocyclic, aromatic ring system, and includes aromatic ring(s) fused to non-aromatic rings, as long as one of the fused rings is an aromatic hydrocarbon. "(C$_6$-C$_{15}$) Aryl" means an aromatic ring system having from 6-15 ring atoms. In some embodiments, aryl is (C$_6$-C$_{25}$)aryl, for example, (C$_6$-C$_{20}$)aryl, (C$_6$-C$_{15}$)aryl, (C$_6$-C$_{12}$)aryl or (C$_6$-C$_{10}$)aryl. Examples of aryl include phenyl, naphthyl, fluorenyl, and the like.

"Arylsulfonyl" refers to an aryl radical attached through —S(O)$_2$— linking group, wherein aryl is as described herein.

"Carbalkoxyalkyl" refers to alkyl substituted with one or more (e.g., one) —C(O)— alkoxy, wherein alkyl and alkoxy are as described herein.

"Carboxyalkyl" refers to alkyl substituted with one or more (e.g., one) —CO$_2$H, wherein alkyl is as described herein.

"Cyano" refers to —CN.

"Heterocyclic" refers to a non-aromatic, cyclic, hydrocarbon radical wherein at least one carbon atom has been replaced with a heteroatom (e.g., N, S and/or O; N or O). "(C$_1$-C$_{10}$)Heterocyclic" refers to a heterocyclic radical having from one to 10 atoms. In some embodiments, heterocyclic is (C$_1$-C$_{25}$)heterocyclic, for example, (C$_1$-C$_{15}$)heterocyclic, (C$_1$-C$_{10}$)heterocyclic, (C$_1$-C$_6$)heterocyclic, (C$_1$-C$_5$) heterocyclic or (C$_1$-C$_3$)heterocyclic. "Heterocyclic" can be saturated or contain one or more units of unsaturation. In some embodiments, heteroaliphatic is heteroalkyl.

"Combination," as used herein, refers to a composition (e.g., pharmaceutical composition) comprising two or more active agents (e.g., AMXT 1501 and DFMO). Typically, the two or more active agents are combined in the combination to provide a single dosage form of the active agents. Also typically, the two or more active agents in a combination target a single disease, disorder or condition, such as cancer. Examples of combinations include combinations comprising AMXT 1501, or a protonated or salt form thereof, and DFMO, or an ionic or salt form thereof, as well as any of the solid forms (e.g., crystalline forms, such as co-crystals and polymorphs) and salts (e.g., pharmaceutically acceptable salts) described herein. Combinations (e.g., solid forms, for example, crystalline forms, such as co-crystals and polymorphs; salts, such as pharmaceutically acceptable salts) comprising AMXT 1501, or a protonated or salt form thereof, and DFMO, or an ionic or salt form thereof, are also referred to herein as AMXT 1501-DFMO combinations (e.g., solid forms, for example, crystalline forms, such as co-crystals and polymorphs; salts, such as pharmaceutically acceptable salts).

"Crystalline," as used herein, refers to a homogeneous solid formed by a repeating, three-dimensional pattern of atoms, ions or molecules having fixed distances between constituent parts. The unit cell is the simplest repeating unit in this pattern. Notwithstanding the homogenous nature of an ideal crystal, a perfect crystal rarely, if ever, exists. "Crystalline," as used herein, encompasses crystalline forms that include crystalline defects, for example, crystalline defects commonly formed by manipulating (e.g., preparing, purifying) the crystalline forms described herein. A person skilled in the art is capable of determining whether a sample of a compound is crystalline notwithstanding the presence of such defects. Crystalline forms can be characterized by analytical methods such as x-ray powder diffraction (XRPD), differential scanning calorimetry (DSC), thermogravimetric analysis (TGA), nuclear magnetic resonance spectroscopy (NMR), single crystal x-ray diffraction, Raman spectroscopy, Fourier transform infrared spectroscopy (FTIR) and/or any other suitable analytical techniques.

An XRPD pattern, DSC thermogram or TGA thermal curve that is "substantially in accordance" with one or more figures herein showing an XRPD pattern or DSC thermogram or TGA thermal curve, respectively, is one that would be considered by one skilled in the art to represent the same single crystalline form as the sample that provided the pattern or thermogram or thermal curve of one or more figures provided herein. Thus, an XRPD pattern or DSC thermogram or TGA thermal curve that is substantially in accordance may be identical to that of one of the figures or, more likely, may be somewhat different from one or more of the figures. For example, an XRPD pattern that is somewhat different from one or more of the figures may not necessarily show each of the lines of the diffraction pattern presented herein and/or may show a slight change in appearance or intensity of the lines or a shift in the position of the lines. These differences typically result from differences in the conditions involved in obtaining the data or differences in the purity of the sample used to obtain the data. A person skilled in the art is capable of determining if a sample of a crystalline form is of the same form as or a different form from a form disclosed herein by comparison of the XRPD pattern and/or DSC thermogram and/or TGA thermal curve of the sample and the corresponding XRPD pattern and/or DSC thermogram and/or TGA thermal curve disclosed herein.

It is to be understood that, unless otherwise indicated, any XRPD peak specified herein, with the exception of the XRPD peaks in the Figures or Examples, means the specified value ±0.2 or less. For example, unless otherwise indicated, when an embodiment or a claim specifies a peak, in terms of 2-theta, at 20.0, this is to be understood to mean 20.0°±0.2° or less, that is a 2-theta angle of from 19.8° to 20.2°. In preferred embodiments, a 2-theta angle is the specified value ±0.1° or less, in more preferred embodiments, ±0.05° or less.

The crystalline forms provided herein can also be identified on the basis of differential scanning calorimetry (DSC) and/or thermogravimetric analysis (TGA). DSC is a thermoanalytical technique in which the difference in the amount of heat required to increase the temperature of a sample is measured as a function of temperature. DSC can be used to detect physical transformations, such as phase transitions, of a sample. For example, DSC can be used to detect the temperature(s) at which a sample undergoes crystallization, melting or glass transition. It is to be understood that any temperature associated with DSC specified herein, with the exception of the DSC temperatures in the Figures or Examples, means the specified value ±5° C. or less. For example, when an embodiment or a claim specifies an endothermic peak at 264° C., this is to be understood to mean 264° C.±5° C. or less, that is a temperature of from 259° C. to 269° C. In preferred embodiments, a DSC is the specified value ±3° C. or less, in more preferred embodiments, ±2° C. or less.

Thermogravimetric analysis (TGA) is a thermoanalytical technique in which the mass change of a substance is measured as a function of temperature or time in a controlled atmosphere. The record is a thermogravimetric curve which is a plot of the mass of the substance versus time or temperature, with the mass loss on the ordinate plotted downward and mass gains plotted upward relative to a baseline. The technique can be used to characterize weight loss or gain due to the sorption/desorption of volatiles, decomposition, oxidation and/or reduction. It is to be understood that any mass change (e.g., loss, gain) associated with TGA specified herein, with the exception of mass changes in the Figures or Examples, means the specified mass change ±0.2%. For example, when an embodiment or a claim specifies 3.2% mass loss over a specified temperature range, this is to be understood to mean 3.2%±0.20%, that is mass loss of from 3.0% to 3.4%. In preferred embodiments, a mass change is the specified value ±0.1%, in more preferred embodiments, the specified value ±0.05%, in yet more preferred embodiments, the specified value ±0.025%. In some embodiments, a mass change is the specified value ±0.02%, for example, ±0.01% or ±0.005%.

"Co-crystal" refers to a crystal composed of two or more different species in a defined stoichiometric ratio and associated with one another in a crystal lattice by noncovalent and nonionic interactions. Co-crystals include solvates and hydrates. In some embodiments, a co-crystal is not a solvate or hydrate.

"Coformer" refers to a species that interacts noncovalently and nonionically with another species, typically, an active pharmaceutical ingredient, in a crystal lattice. Coformers include solvents and water, as well as pharmaceutically acceptable acids and bases identified herein as useful to form pharmaceutically acceptable salts, particularly those acids and bases having a $pK_a$ difference from the other species in the crystal lattice of less than 2 and, preferably, of less than 1. In some embodiments, a conformer is not a solvent or water.

The term "salt" has its standard meaning in the art, and refers to a positively charged species (cation) and a negatively charged species (anion) that are complexed to one another through an ionic interaction. Generally, these salts do not involve covalent bonding between partner molecular components. Salts can be obtained by customary methods known to those skilled in the art, for example, by combining a compound with an inorganic or organic acid or base in a solvent or diluent, or from other salts by cation exchange or anion exchange.

The phrase "pharmaceutically acceptable" means that the substance or composition the phrase modifies is, within the scope of sound medical judgment, suitable for use in contact with the tissues of humans and lower animals without undue toxicity, irritation, allergic response and the like, and are commensurate with a reasonable benefit/risk ratio.

The term "pharmaceutically acceptable salt" refers to those salts which are, within the scope of sound medical judgment, suitable for use in contact with the tissues of mammals without undue toxicity, irritation, allergic response and the like, and are commensurate with a reasonable benefit/risk ratio. Pharmaceutically acceptable salts are well known in the art. An example list of pharmaceutically acceptable salts can be found in the Handbook of Pharmaceutical Salts: Properties, Selection and Use, P. H. Stahl and C. G. Wermuth editors, Weinheim/Zurich:Wiley-VCHA/VHCA, 2002, the relevant teachings of which are incorporated herein by reference in their entirety. Pharmaceutically acceptable salts include pharmaceutically acceptable acid addition salts and pharmaceutically acceptable base addition salts.

Examples of pharmaceutically acceptable acid addition salts are salts of an amino group formed with inorganic acids such as hydrochloric acid, hydrobromic acid, phosphoric acid, sulfuric acid and perchloric acid, or with organic acids, such as acetic acid, oxalic acid, maleic acid, tartaric acid, citric acid, succinic acid or malonic acid or by using other methods used in the art, such as ion exchange. Other pharmaceutically acceptable acid addition salts include adipate, alginate, ascorbate, aspartate, benzenesulfonate, benzoate, bisulfate, borate, butyrate, camphorate, camphorsulfonate, cinnamate, citrate, cyclopentanepropionate, digluconate, dodecylsulfate, ethanesulfonate, formate, fumarate, glucoheptonate, glycerophosphate, gluconate, glutarate, glycolate, hemisulfate, heptanoate, hexanoate, hydroiodide, hydroxybenzoate, 2-hydroxy-ethanesulfonate, hydroxymaleate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 2-phenoxybenzoate, phenylacetate, 3-phenylpropionate, phosphate, pivalate, propionate, pyruvate, salicylate, stearate, succinate, sulfate, tartrate, thiocyanate, p-toluenesulfonate, undecanoate, valerate salts, and the like. Either the mono-, di- or tri-acid salts can be formed, and such salts can exist in either a hydrated, solvated or substantially anhydrous form.

Other pharmaceutically acceptable acid addition salts include salts formed with hydrophobic carboxylic acids, such as those described in U.S. Pat. No. 10,632,145, the entire content of which is incorporated herein by reference in its entirety. Hydrophobic carboxylic acids include those carboxylic acid-containing compounds having a water solubility of less than 10 g/L, e.g., less than 1 g/L, or less than 0.1 g/L, or less than 0.01 g/L in water, as determined at a temperature of 25° C. and a pH of 7. Compendiums of the water solubility of carboxylic acid-containing compounds may be found in, e.g., Yalkowsky S H, Dannenfelser R M; The AQUASOL database of Aqueous Solubility. Fifth ed., Tucson, Ariz.: Univ. AZ, College of Pharmacy (1992); Yalkowsky S H et al; Arizona Data Base of Water Solubility (1989); and The Handbook of Aqueous Solubility Data, Second Edition, edited by Yalkowsky S H, He, Y, and Jain, P, CRC Press (2010). Specific examples of hydrophobic carboxylic acids include fatty acids, such as $C_8$-$C_{18}$ straight chain hydrocarbon fatty acids, such as octanoic acid (also known as caprylic acid), nonanoic acid, decanoic acid (also known as capric acid), undecanoic acid, dodecanoic acid (also known as lauric acid), tridecanoic acid, tetradecanoic acid and hexadecanoic acid. Capric acid is a preferred hydrophobic carboxylic acid.

Pharmaceutically acceptable base addition salts include salts formed with inorganic bases, such as alkali metal, alkaline earth metal, and ammonium bases, and salts formed with aliphatic, alicyclic or aromatic organic amines, such as methylamine, trimethylamine and picoline, or $N^+((C_1$-$C_4)$ alkyl$)_4$ salts. Representative alkali or alkaline earth metal salts include sodium, lithium, potassium, calcium, magnesium, barium and the like. Further pharmaceutically acceptable base addition salts include, when appropriate, nontoxic ammonium, quaternary ammonium, and amine cations formed using counterions such as halide, hydroxide, carboxyl, sulfate, phosphate, nitrate, lower alkyl sulfonate and aryl sulfonate.

Compounds can also exist as "solvates" or "hydrates." A "hydrate" is a compound that exists in a composition with one or more water molecules. A hydrate can include water in stoichiometric quantities, such as a monohydrate or a dihydrate, or can include water in random amounts. A "solvate" is similar to a hydrate, except that a solvent other than water, such as methanol, ethanol, dimethylformamide, diethyl ether, or the like replaces water. Mixtures of such solvates or hydrates can also be prepared.

"Ionic," used herein, refers to a positively or negatively charged group. Examples of positively charged groups include protonated amino groups (e.g., $NH_4^+$). Examples of negatively charged groups include anions, such as carboxylate ($CO_2^-$) and $Cl^-$. Ionic forms include anionic forms (having an overall negative charge), cationic forms (having an overall positive charge) and zwitterionic forms, where a molecule has separate negatively charged group(s) and positively charged group(s) rendering the overall charge zero.

Compounds may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemic mixtures, individual isomers (e.g., diastereomers, enantiomers, geometrical isomers (including cis and trans double bond isomers), conformational isomers (including rotamers and atropisomers), tautomers, and intermediate mixtures, with all possible isomers and mixtures thereof being included, unless otherwise indicated.

When a disclosed compound is depicted by structure without indicating the stereochemistry, and the compound has one or more chiral centers, it is to be understood that the structure encompasses one enantiomer or diastereomer of the compound separated or substantially separated from the corresponding optical isomer(s), a racemic mixture of the compound, and mixtures enriched in one enantiomer or diastereomer relative to its corresponding optical isomer(s). When a disclosed compound is depicted by a structure indicating stereochemistry, and the compound has more than one chiral center, the stereochemistry indicates relative stereochemistry, rather than the absolute configuration of the substituents around the one or more chiral carbon atoms. "R" and "S" can be used to indicate the absolute configuration of substituents around one or more chiral carbon atoms. D- and L- can also be used to designate stereochemistry.

"Enantiomers" are pairs of stereoisomers that are non-superimposable mirror images of one another, most commonly because they contain an asymmetrically substituted carbon atom that acts as a chiral center.

"Diastereomers" are stereoisomers that are not related as mirror images, most commonly because they contain two or more asymmetrically substituted carbon atoms.

"Racemate" or "racemic mixture," as used herein, refer to a mixture containing equimolar quantities of two enantiomers of a compound. Such mixtures exhibit no optical activity (i.e., they do not rotate a plane of polarized light).

Percent enantiomeric excess (ee) is defined as the absolute difference between the mole fraction of each enantiomer multiplied by 100% and can be represented by the following equation:

$$ee = \left|\frac{R-S}{R+S}\right| \times 100\%,$$

where R and S represent the respective fractions of each enantiomer in a mixture, such that R+S=1. An enantiomer may be present in an ee of at least or about 50%, about 60%, about 70%, about 80%, about 90%, about 95%, about 98%, about 99% or about 99.9%.

Percent diastereomeric excess (de) is defined as the absolute difference between the mole fraction of each diastereomer multiplied by 100% and can be represented by the following equation:

$$de = \left|\frac{D1 - (D2 + D3 + D4 \ldots)}{D1 + (D2 + D3 + D4 \ldots)}\right| \times 100\%,$$

where D1 and (D2+D3+D4 . . . ) represent the respective fractions of each diastereomer in a mixture, such that D1+(D2+D3+D4 . . . )=1. A diastereomer may be present in a de of at least or about 50%, about 60%, about 70%, about 80%, about 90%, about 95%, about 98%, about 99% or about 99.9%.

Compounds can also exist as isotopologues, differing from a disclosed structure only in the presence of one or more isotopically enriched atoms. For example, compounds produced by the replacement of a hydrogen with deuterium or tritium, or of a carbon with a $^{13}$C- or $^{14}$C-enriched carbon are within the scope of this disclosure. In all provided structures, any hydrogen atom can also be independently selected from deuterium ($^2$H), tritium ($^3$H) and/or fluorine ($^{18}$F). Such compounds are useful, for example, as analytical tools, as probes in biological assays, or as therapeutic agents in accordance with the present disclosure.

As used herein, the term "combination of the disclosure" refers to any combination described herein comprising DFMO and a polyamine transport inhibitor (e.g., a compound of structural formula I or a subformula thereof), as well as isomers, such as stereoisomers (including diastereoisomers, enantiomers and racemates) and tautomers, isotopologues, inherently formed moieties (e.g., polymorphs and/or solvates, such as hydrates), ionic forms and salts (e.g., pharmaceutically acceptable salts) of DFMO and/or the polyamine transport inhibitor.

"Pharmaceutically acceptable carrier" refers to a non-toxic carrier or excipient that does not destroy the pharmacological activity of an agent(s) with which it is formulated and is nontoxic when administered in doses sufficient to deliver a therapeutic amount of the agent(s). Pharmaceutically acceptable carriers that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

"Treatment" and "treating" refer to medical management of a disease, disorder, or condition of a subject. A treatment may improve or decrease the severity at least one symptom of a disease, disorder or condition; delay worsening or progression of a disease, disorder or condition; delay or prevent onset of additional associated diseases, disorders or conditions; or improve remodeling of lesions into functional (partially or fully) tissue.

A "therapeutically effective amount" or "effective amount" of a therapy refers to that amount sufficient to result in amelioration of one or more symptoms of the disease being treated in a statistically significant manner. When referring to an individual active ingredient administered alone, a therapeutically effective amount refers to that ingredient alone. When referring to a combination, a therapeutically effective amount refers to combined amounts of the active ingredients that result in the therapeutic effect, whether administered serially or simultaneously.

"Subject," as used herein, refers to a mammal. In addition to warm-blooded animals, such as mice, rats, horses, cattle, sheep, dogs, cats, monkeys, etc., "subject" includes humans. In preferred embodiments, a subject is a human.

"Subject in need" refers to a subject at risk of, or suffering from, a disease, disorder or condition that is amenable to treatment in accordance with the present disclosure. In certain embodiments, a subject in need is a mammal, e.g., a human.

Polyamine Transport Inhibitors

AMXT 1501 acts as a potent blocker of polyamine uptake into cancer cells.

Examples of other polyamine or polybasic drugs include inhibitors of the polyamine precursor-forming enzyme known as S-adenosylmethionine decarboxylase (AdoMetDC), such as MGBG. MGBG is a poly-cationic, charged molecule, and has been shown to be a potent inhibitor of S-adenosylmethionine decarboxylase. The S-adenosylmethionine decarboxylase inhibitor CGP-48664 is also a poly-cationic, poly-basic amine. Other polyamine transport inhibitors, such as Trimer PTI, are likewise useful for oncology therapy. AMXT 1501 is D-lys(palmitoyl)-spermine, and has the following structure:

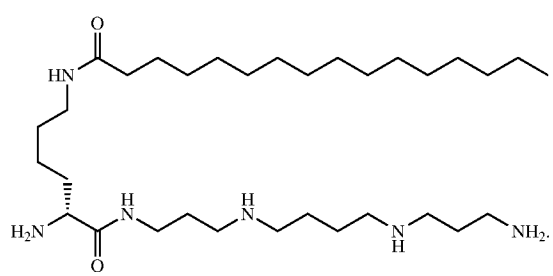 [SMILES: CCCCCCCCCCCCCCCC(=O)NCCCC[C@@H](N)C(=O)NCCCNCCCCNCCCN]

MGBG has the following structure:

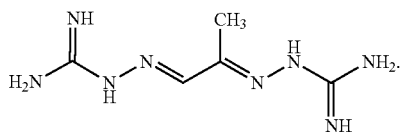

CGP-48664 has the following structure:

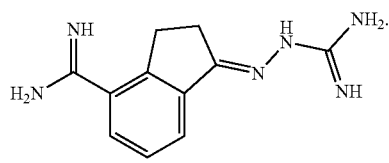

Trimer PTI has the following structure:

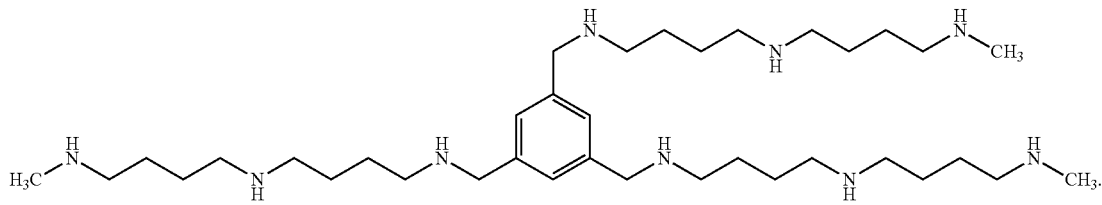 [SMILES: CNCCCCNCCCCNCc1cc(CNCCCCNCCCCNC)cc(CNCCCCNCCCCNC)c1]

Various terminally di-alkylated polyamines, such as diethyl-norspermine (DENSPM), have also been explored as polyamine anti-metabolites for cancer treatment. This, and other, diethyl polyamine analogs have been shown to induce the polyamine degradation enzyme spermidine/spermine $N^1$-acetyltransferase (SSAT) in cancer cells. DENSPM has the following structure:

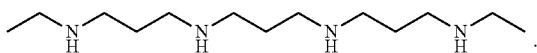 [SMILES: CCNCCCNCCCNCCCNCC]

Further polyamine transport inhibitors are disclosed in U.S. Pat. No. 10,632,145, the entire content of which is incorporated herein by reference.

In some embodiments, a polyamine transport inhibitor is a compound of the following structural formula:

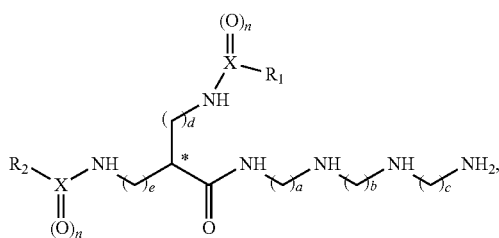

or a protonated form thereof, wherein.

each of a, b and c is independently an integer from one to ten;
each of d and e is independently an integer from 0 to 30;
each X is independently carbon or sulfur;

each n is independently 0 or 1 when the adjacent X is carbon, or 2 when the adjacent X is sulfur; and $R_1$ and $R_2$ are each independently selected from hydrogen or straight or branched, saturated or unsaturated ($C_1$-$C_{50}$)aliphatic; carboxyalkyl; carbalkoxyalkyl; alkoxy; ($C_1$-$C_{10}$)alicyclic; single- or multi-ring aryl aliphatic; aliphatic single- or multi-ring aromatic; single- or multi-ring heterocyclic; single- or multi-ring heterocyclic aliphatic; arylsulfonyl; or cyano; or $R_1$—X(O)$_n$—, $R_2$—X(O)$_n$— or $R_1$—X(O)$_n$— and $R_2$—X(O)$_n$— are replaced by hydrogen.

In some embodiments of a compound of structural formula I, $R_2$—X(O)$_n$— is replaced by hydrogen. In alternative embodiments, $R_1$—X(O)$_n$— is replaced by hydrogen.

In some embodiments of a compound of structural formula I, each of a, b and c is independently an integer from one to five. In more specific embodiments, each of a, b and c is independently three or four. In yet more specific embodiments, a is three, b is four and c is three.

In some embodiments of a compound of structural formula I, d is an integer from one to five. In more specific embodiments, d is four.

In some embodiments of a compound of structural formula I, e is 0.

In some embodiments of a compound of structural formula I, each X is carbon.

In some embodiments of a compound of structural formula I, $R_1$ and $R_2$ are each independently selected from hydrogen or straight or branched, saturated or unsaturated ($C_1$-$C_{50}$)aliphatic or ($C_1$-$C_{10}$)alicyclic. In more specific embodiments, $R_1$ and $R_2$ are each independently selected from straight or branched, saturated or unsaturated ($C_1$-$C_{50}$) aliphatic or ($C_1$-$C_{10}$)alicyclic. In yet more specific embodiments, $R_1$ and $R_2$ are each independently selected from ($C_1$-$C_{25}$)alkyl or ($C_1$-$C_{10}$)cycloalkyl.

Specific examples of a compound of structural formula (I) include the compounds listed in Table 7. In a particular embodiment, a polyamine transport inhibitor described herein (e.g., a compound of structural formula I) is AMXT 1501, or a protonated form thereof.

Combinations with DFMO

The combination of AMXT 1501 and DFMO has promise as a broadly-applicable, anti-cancer therapy for solid tumors. Together, the two agents target cancer cells' polyamine metabolic pathway, an approach that has been shown to suppress tumor growth in both a polyamine- and a T-cell-dependent manner. DFMO inhibits the rate-limiting polyamine biosynthesis enzyme, ornithine decarboxylase (ODC). AMXT 1501 acts as a potent blocker of polyamine uptake into cancer cells. The combination of AMXT 1501 and DFMO produces a marked reduction in the tumor burden in multiple murine nonclinical models, including children's cancers, neuroblastoma and diffuse intrinsic pontine glioma (DIPG). Pharmacological benefits of the combination of AMXT 1501 and DFMO include reduction of solid tumor growth, and induction of an adaptive immune reactivity to primary tumors and their metastases, which suggests that the combination will produce a sustained affect against cancer in human patients. DFMO has the following structure:

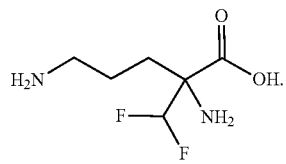 [SMILES: NCCCC(N)(C(=O)O)C(F)F]

In addition to AMXT 1501, other polyamine or polybasic drugs, especially those targeting the polyamine metabolic pathway, can be combined with DFMO to form ionic salt pairings. For example, treatment with DFMO has been shown to lead to greatly increased uptake of MGBG, a potent inhibitor of S-adenosylmethionine decarboxylase, by cancer cells. This observation led to clinical testing of DFMO and MGBG in combination for cancer therapy. Therefore, combination inhibition of the polyamine precursor-generating enzymes targeted by DFMO and MGBG, ornithine decarboxylase (ODC) and S-adenosylmethionine decarboxylase (AdoMetDC), respectively, is clinically desirable for oncology therapy.

DENSPM, and other diethyl polyamine analogs have been shown to induce the polyamine degradation enzyme spermidine/spermine $N^1$-acetyltransferase (SSAT) in cancer cells. Induction of this polyamine degradation enzyme, together with inhibition of the polyamine producing enzyme, ODC, could also have usefulness for oncology therapy.

Accordingly, provided herein are combinations (e.g., pharmaceutical combinations) comprising difluoromethylornithine (DFMO), or an ionic form thereof, and a polyamine transport inhibitor (e.g., a compound of structural formula (I)), or a protonated form thereof.

Figure 5:
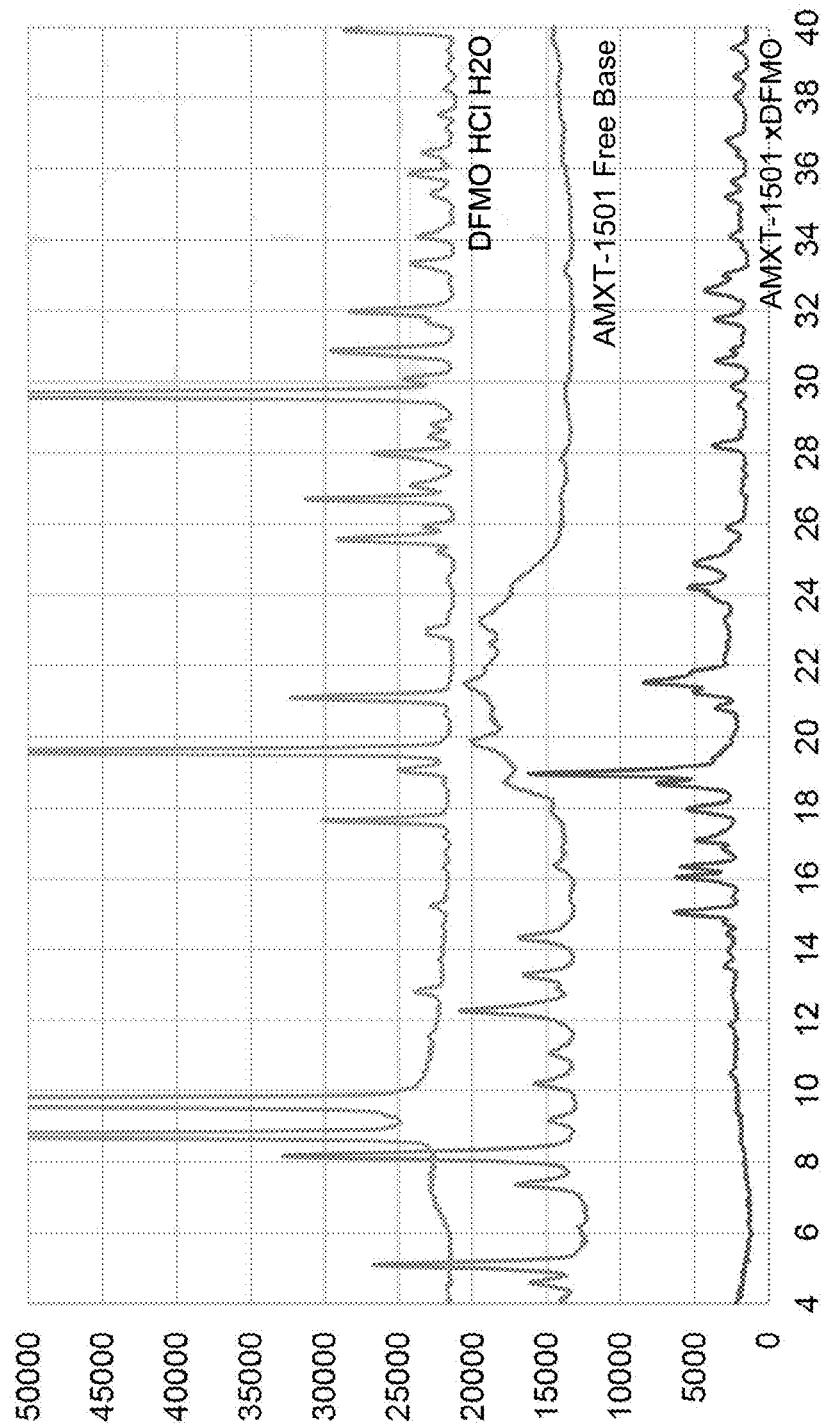
FIG. 5 is x-ray pattern diffractograms, and shows the overlap of the x-ray diffraction patterns of Lot 4-138, DFMO and AMXT 1501.
Figure 11:
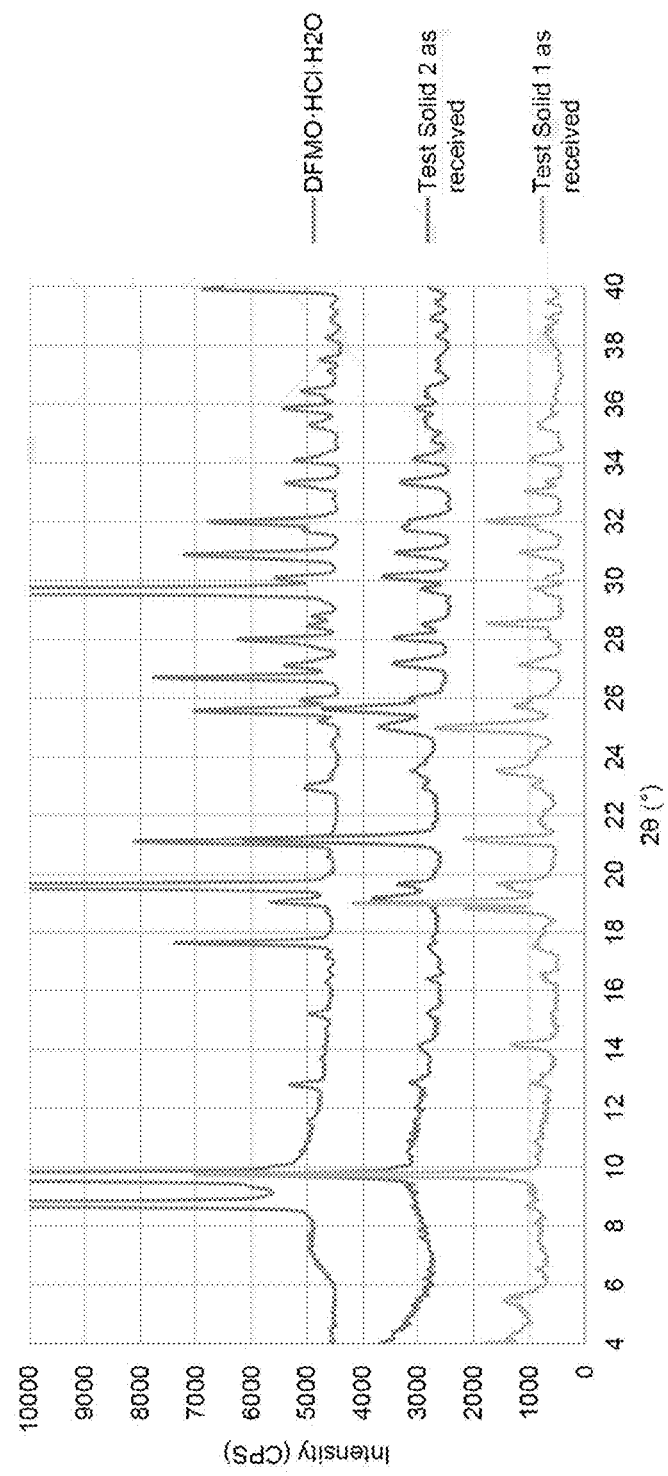
FIG. 11 is x-ray pattern diffractograms, and shows the overlay of the x-ray diffraction patterns of Test Solid 1, Test Solid 2 and DFMO.HCl.H$_2$O.

Also provided herein are solid forms (e.g., crystalline solid forms, such as co-crystals or crystalline salts; amorphous solid forms) comprising DFMO, or an ionic form thereof, and a polyamine transport inhibitor (e.g., a compound of structural formula (I)), or a protonated form thereof. In some embodiments, the solid form is a crystalline solid form. In some embodiments, the crystalline form is characterized by an x-ray diffraction pattern substantially in accordance with that depicted in FIG. 5 or one of those depicted in FIG. 11.

In some embodiments, the crystalline form is characterized by an x-ray powder diffraction pattern comprising peaks at two theta angles of 15.2, 19.2 and 19.6. In more specific embodiments, the x-ray powder diffraction further comprises at least one (e.g., one, at least two, two, at least three, three, at least four, four, at least five, five, at least six, six, at least seven, seven, eight) peak at a two theta angle selected from 9.8, 12.8, 14.3, 16.4, 21.2, 22.9, 23.5 or 25.0.

In some embodiments, the crystalline form is characterized by an x-ray powder diffraction pattern comprising peaks at two theta angles of 18.9 and 19.0, and further comprising at least one (e.g., one, at least two, two, at least three, three, at least four, four, at least five, five, six) peak at a two theta angle selected from 9.8, 12.8, 14.3, 21.2, 22.9 or 23.5.

In some embodiments, the crystalline form is characterized by an x-ray powder diffraction pattern comprising peaks at two theta angles of 9.8 and 14.3, and further comprising at least one (e.g., one, at least two, two, three) peak at a two theta angle of 16.4, 23.5 or 25.0. In more specific embodiments, the x-ray powder diffraction further comprises at least one (e.g., one, at least two, two, at least three, three, at least four, four, at least five, five, six) peak at a two theta angle selected from 12.8, 16.4, 21.2, 22.9, 23.5 or 25.0.

Also provided herein is a co-crystal comprising DFMO, or a salt thereof (e.g., a pharmaceutically acceptable salt thereof), and a polyamine transport inhibitor (e.g., a compound of structural formula (I)), or a salt thereof (e.g., a pharmaceutically acceptable salt thereof). In some embodiments, the co-crystal further comprises a coformer, such as HCl and/or water.

Also provided herein is a salt (e.g., a pharmaceutically acceptable salt) comprising DFMO, or an ionic (e.g., deprotonated) form thereof, and a polyamine transport inhibitor (e.g., a compound of structural formula (I)), or a protonated form thereof. In some embodiments, the salt comprises an ionic (e.g., deprotonated) form of DFMO and a protonated (e.g., monoprotonated, diprotonated, triprotonated, tetraprotonated) form of the polyamine transport inhibitor.

It will be understood that DFMO, by virtue of its structure, may exist in anionic form, cationic form or zwitterionic form. Without wishing to be bound by any particular theory, it is believed that when DFMO forms a salt with a polyamine transport inhibitor in accordance with the present disclosure, the carboxylic acid of DFMO is deprotonated and the resulting carboxylate interacts ionically with a corresponding cation of the polyamine transport inhibitor (e.g., a protonated amine of AMXT 1501). In such salts, one or both of the amino groups of DFMO may also be protonated, and the resulting substituted ammonium group(s) may interact ionically with a corresponding anion(s), such as $Cl^-$.

It will also be understood that the ratio of DFMO, or an ionic form thereof, to a polyamine transport inhibitor, or a protonated form thereof, in the combinations of the disclosure can vary. For example, a salt described herein may comprise a single molecule of a protonated form of a polyamine transport inhibitor and one or more than one (e.g., two, three, four) molecules of an ionic form of DFMO, such that, for example, two molecules of the DFMO may each be complexed with a single molecule of the polyamine transport inhibitor. The molar ratio of DFMO, or an ionic form thereof, to the polyamine transport inhibitor, or a protonated form thereof, in any of the combinations of the disclosure (e.g., co-crystal, salt) or compositions described herein can be from about one to one (1:1) to about 25 to one (25:1), e.g., from about one to one (1:1) to about 10 to one (10:1), about two to one (2:1), about three to one (3:1), about four to one (4:1), about five to one (5:1), about six to one (6:1), about seven to one (7:1), about eight to one (8:1), about nine to one (9:1) or about ten to one (10:1). In some embodiments, the molar ratio of DFMO, or an ionic form thereof, to the polyamine transport inhibitor, or a protonated form thereof, in any of the combinations of the disclosure (e.g., co-crystal, salt) or compositions described herein is from about 1:1 to about 10:1. In more specific embodiments, the molar ratio of DFMO, or an ionic form thereof, to the polyamine transport inhibitor, or a protonated form thereof, in any of the combinations of the disclosure (e.g., co-crystal, salt) or compositions described herein is about 8:1. In other embodiments, the molar ratio of DFMO, or an ionic form thereof, to the polyamine transport inhibitor, or a protonated form thereof, in any of the combinations of the disclosure (e.g., co-crystal, salt) or compositions described herein is about 4:1. In yet other embodiments, the molar ratio of DFMO, or an ionic form thereof, to the polyamine transport inhibitor, or a protonated form thereof, in any of the combinations of the disclosure (e.g., co-crystal, salt) or compositions described herein is about 3:1. In yet other embodiments, the molar ratio of DFMO, or an ionic form thereof, to the polyamine transport inhibitor, or a protonated form thereof, in any of the combinations of the disclosure (e.g., co-crystal, salt) or compositions described herein is about 2:1.

In addition, a combination of the disclosure (e.g., co-crystal, salt) may further comprise one or more additional molecules. For example, the combination may further comprise a conformer, such as a salt, or one or more additional ionic species. For example, a salt comprising an ionic form of DFMO complexed with a protonated form of a polyamine transport inhibitor as described above, may further comprise an additional ionic species (e.g., anionic species) complexed with DFMO, e.g., Cl⁻.

Thus, in some embodiments, a salt further comprises an anion or cation of any of the pharmaceutically acceptable acids and bases identified herein as useful to form pharmaceutically acceptable salts, particularly those which have a $pK_a$ difference of greater than or equal 2 compared to DFMO and/or the polyamine transport inhibitor in the salt. The salt may also or alternatively further be a solvate and/or hydrate, in which case one or more solvent and/or water molecules are also or alternatively, respectively, complexed to the salt.

In some embodiments, a co-crystal further comprises a coformer, such as a pharmaceutically acceptable acid or base identified herein as useful to form pharmaceutically acceptable salts, particularly those acids and bases having a $pK_a$ difference of less than 2 and, preferably of less than 1, compared to DFMO and/or the polyamine transport inhibitor in the co-crystal. In some embodiments, the coformer includes hydrochloric acid and/or water.

In general, when preparing the combinations, the polyamine transport inhibitor may be provided in free base form or as a salt which includes one or more anions. Likewise, DFMO may be provided in a form wherein the carboxylate is protonated or as the carboxylate, which includes a cation. By virtue of the structure of DFMO the cation could be the substituted ammonium group of another molecule of DFMO. Alternatively, the cation could be a different cation. The salt form of the polyamine transport inhibitor may be referred to as an acid addition salt of the polyamine, while the salt form of the carboxylate may be referred to as a base addition salt of the carboxylic acid. These salts may be prepared by methods known in the art and disclosed herein.

In one process for preparing combinations of the disclosure, the combination of polyamine transport inhibitor and DFMO does not include any additional anions or cations. Such a combination may be prepared by combining the free base form of the polyamine transport inhibitor with the free acid form of DFMO. Thus, a convenient process for preparing a combination of the present disclosure is to combine a polyamine transport inhibitor in free base form with DFMO in free acid form in a solvent under proton transfer conditions to form, e.g., a salt of a positively charged polyamine transport inhibitor and a negatively charged carboxylate of DFMO. The salt can then be separated (e.g., isolated) from the solvent.

Thus, the present disclosure provides a method of making a combination of the disclosure, comprising: combining a polyamine transport inhibitor, or a salt thereof, and DFMO, or a salt thereof, in a solvent (e.g., a solvent that allows for proton transfer) to provide a mixture. In some embodiments, the method further comprises isolating a solid from the mixture, wherein the solid comprises a combination of the disclosure (e.g., a salt described herein).

Optionally, the method may further comprise any one or more (e.g., any two, any three, any four) of the following. The polyamine transport inhibitor and the DFMO may be combined in relative amounts so as to provide the desired stoichiometry. For example, if a 1:1 molar stoichiometry of polyamine transport inhibitor:DFMO is desired, then equal, or approximately equal, molar amounts of polyamine and hydrophobic carboxylic acid are combined in the solvent. Thus, in one embodiment, about 1 mole, e.g., 0.9-1.1 moles, of DFMO are combined with each 1 mole of polyamine transport inhibitor. If a 1:2 molar stoichiometry of polyamine transport inhibitor:DFMO is desired, then exactly or about 2 moles, e.g., 1.8-2.2 moles, of DFMO are combined with each 1 mole of polyamine transport inhibitor. If a 1:4 molar stoichiometry of polyamine transport inhibitor:DFMO is desired, then exactly or about 4 moles, e.g., 3.6-4.4 moles, of DFMO are combined with each 1 mole of polyamine transport inhibitor.

In the case where it is desirable to facilitate salt formation in the methods of making described herein, the solvent should facilitate proton transfer amongst the species in the reaction mixture, e.g., between DFMO and the polyamine transport inhibitor. For example, the solvent may be a pure polar protic solvent or it may be a mixture of solvents comprising a polar protic solvent. A suitable polar protic solvent is water, e.g., a water selected from deionized water and distilled water. Another suitable polar protic solvent is a lower-chain alcohol, e.g., methanol or ethanol.

Preferably, the mixture is a solution. In such embodiments, the components may be combined in any order so as to form a solution. For example, the polyamine transport inhibitor and the DFMO may be added to the solvent so as to provide the solution. In one embodiment, the polyamine transport inhibitor is dissolved in the solvent, and then the DFMO is gradually added to the solution of solvent and polyamine transport inhibitor.

The process may be performed in a batch or a continuous mode. In a batch mode, a container receives the full charge of solvent, polyamine transport inhibitor and DFMO, and the combination is formed in the container. The polyamine transport inhibitor, DFMO and solvent may be combined so as to provide a solution. Typically, the polyamine transport inhibitor, DFMO and solvent are combined at a temperature within the range of 10-30° C., although other temperatures may be used. In a continuous mode, continuous flow techniques can be used for the production and isolation of the combinations described. Use of available flow apparatus, wherein solutions of the polyamine transport inhibitor in free base form in a suitable solvent such as methanol, are mixed with a co-solvent in which the combination is not soluble, such as acetonitrile, in a flow cell apparatus, allow for continuous production of the insoluble, or soluble form of the combination.

After the combination is formed, the solvent can be separated from the combination to provide a residue (e.g., a solid residue) that is, or includes, the combination. When the solvent is volatile, then it may be removed from the solution by a process such as evaporation or distillation, so as to isolate the residue from the solution. As another option, a co-solvent (an example being acetonitrile) may be added to the solution, whereupon a precipitate comes out of solution, and the resulting solution is referred to as the supernatant.

The co-solvent may also be referred to as a non-solvent, since the combination is not soluble in the non-solvent. The precipitate, also referred to as a residue, may be separated from the supernatant, e.g., by decantation, so as to isolate the residue from the solvent(s). As yet another option, the solution may be chilled to a temperature such that the combination is no longer soluble in the solvent(s) and thus forms a residue in the form of a precipitate. As in the case when a co-solvent is used to form the precipitate, the supernatant may be separated from the residue so as to isolate the residue from the solvent(s). Once the residue is formed, it or a portion thereof may be combined with additional components as described herein so as to form a pharmaceutical composition suitable for administration to a subject, e.g., by ingestion. Those additional components may include diluents, e.g., lactose and microcrystalline cellulose, disintegrants, e.g., sodium starch glycolate and croscarmellose sodium, binders, e.g., PVP and HPMC, lubricants, e.g, magnesium stearate, and glidants, e.g., colloidal $SiO_2$. For example, a method described herein may further comprise formulating a combination into a composition (e.g., pharmaceutical composition), e.g., by forming a solid dosage form selected from a pill, a tablet, a capsule, a lozenge, a caplet, and a pastille, from the residue or a portion thereof. The combination so formulated may be in sterile form, so as to be used in the manufacture of a pharmaceutical agent.

As mentioned above, a protonated form of a polyamine transport inhibitor, such as a salt of a polyamine transport inhibitor, and/or an ionic form of DFMO may alternatively be used to prepare a combination of the disclosure.

An acid addition salt of a polyamine transport inhibitor may be formed by bringing the polyamine transport inhibitor into contact with a suitable inorganic or organic acid under conditions known to the skilled person. An acid addition salt may, for example, be formed using an inorganic acid. Suitable inorganic acids may be selected from the group consisting of hydrochloric acid, hydrobromic acid, sulphuric acid and phosphoric acid. An acid addition salt may also be formed using an organic acid. Suitable organic acids may be selected from the group consisting of trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and paratoluenesulfonic acid.

A base addition salt of a carboxylic acid (e.g., of DFMO) may be formed by bringing the carboxylic acid into contact with a suitable inorganic or organic base under conditions known to the skilled person. Suitable inorganic bases which form suitable base addition salts include the hydroxide form of any of lithium, sodium, potassium, calcium, magnesium or barium. Suitable organic bases which form suitable base addition salts include aliphatic, alicyclic or aromatic organic amines such as methylamine, trimethylamine and picoline, alkylammonias and ammonia.

Pharmaceutical Compositions

A combination of the disclosure can be administered to a subject in pure or substantially pure form (e.g., not in admixture with another solid or liquid). Typically, for administration to a subject, a combination of the disclosure is formulated with one or more pharmaceutically acceptable excipients. Thus, one embodiment is a composition (e.g., pharmaceutical composition) comprising a combination of the disclosure and a pharmaceutically acceptable excipient. The compositions described herein can be used in the methods described herein, e.g., to supply a combination of the disclosure for administration to a subject.

The compositions described herein may be formulated for administration by oral, parenteral (e.g., intramuscular, intraperitoneal, intravenous, intracerebroventricular, intracisternal injection or infusion, subcutaneous injection, or implant), inhalation spray, nasal, vaginal, rectal, sublingual, or topical routes of administration. In preferred embodiments, the compositions described herein are formulation for oral administration.

The compositions described herein may be formulated into suitable dosage forms (e.g., unit dosage forms), e.g., containing pharmaceutically acceptable excipient(s) appropriate for the intended route of administration. Accordingly, some embodiments provide a dosage form (e.g., unit dosage form) comprising a composition described herein.

Compositions described herein can be prepared by any of the methods well known in the art of pharmacy. For example, some methods include the step of bringing the active ingredient(s), e.g., a combination of the disclosure, into association with a pharmaceutically acceptable excipient(s). In general, compositions are prepared by uniformly and intimately bringing a combination of the disclosure into association with a liquid carrier or a finely divided solid carrier or both, and then, if necessary, shaping the product into the desired formulation. In the composition, the combination is included in an amount sufficient to produce the desired effect upon the process or condition of disease. For example, in some embodiments, the concentration of the combination in the composition is from about 0.001% to about 99%, from about 0.01% to about 98%, from about 0.1% to about 95%, from about 0.1% to about 50%, from about 0.1% to about 25%, from about 0.2% to about 20%, or from about 1% to about 10% w/w, w/v or v/v (e.g., w/w).

In one embodiment, the composition (e.g., pharmaceutical composition) is a solid dosage form, e.g., intended for oral use. For many reasons, an oral composition, and particularly a solid oral dosage form, is advantageous and convenient for both the patient and the medical practitioner responsible for developing the therapeutic regime. An oral composition avoids the complications, cost and inconvenience of administration via IV injection or infusion which must be done by a medical professional in a hospital or outpatient setting which exposes him or her to hospital-based infections and illnesses. In particular, patients undergoing treatment for cancer may be immunocompromised individuals and particularly susceptible to hospital-based infections and illnesses. An oral formulation, such as a pill or tablet, may be taken outside of a hospital setting, increasing the potential for subject ease of use and compliance. This permits a subject to avoid infection risks concomitant with IV administration and hospital visits. In addition, oral delivery may avoid the high concentration peak and rapid clearance associated with an IV bolus dose.

Examples of oral solid dosage forms include pills, tablets, capsules, granules, and microspheres, any of which may include an enteric coating to protect the composition from acid degradation by stomach environment, or to maximize delivery to intestinal sections where absorption may be enhanced. The solid dosage form may be chewable or swallowable, or have any suitable ingestible form. In one embodiment, the solid dosage form contains little or no water, e.g., less than 0.1 weight percent water, less than 0.2 weight percent water, less than 0.3 weight percent water, less than 0.4 weight percent water, less than 0.5 weight percent water, less than 1 weight percent water, less than 1.5 weight percent water, less than 2 weight percent water or less than 5 weight percent water.

For oral administration, the compositions are preferably provided in a solid dosage form, such as the form of pills, capsules, tablets and the like, containing from about 1 milligram to about 5,000 milligrams, for example, from about 1 milligram to about 2,500 milligrams, from about 1 milligram to about 1,000 milligrams, from about 50 milligrams to about 500 milligrams or from about 50 milligrams to about 350 milligrams, particularly about: 1, 5, 10, 15, 20, 25, 50, 75, 100, 150, 200, 250, 300, 400, 500, 600, 750, 800, 900, or 1,000 milligrams, of active ingredient(s) (e.g., a combination of the disclosure).

In one embodiment, a solid dosage form contains about: 10 mg, or 20 mg, or 30 mg, or 40 mg, or 50 mg, or 60 mg, or 70 mg, or 80 mg, or 90 mg, or 100 mg, or 110 mg, or 120 mg, or 130 mg, or 140 mg, or 150 mg, or 200 mg, or 250 mg, or 300 mg, or 350 mg, or 400 mg, or 450 mg, or 500 mg, of a polyamine transport inhibitor, where that polyamine transport inhibitor will, however, be present in the solid dosage form in combination with DFMO. The amount of the polyamine transport inhibitor present in a solid dosage form may also be characterized in terms of a range of possible amounts, where lower and upper limits of the range are selected from the amounts just described, e.g., from about 10 mg to about 500 mg, or numbers in between, e.g., from about 50 to about 350 mg. A tablet or pill will typically have a total weight of at least 50 mg.

In one embodiment, the solid dosage form provides a therapeutically effective systemic plasma level of a polyamine transport inhibitor and/or DFMO for a period of at least 4, 5, 6, 7, 8, 9, 10, 11, 12, 13, 14, 15, 16, 17, 18, 19, 20, 21, 22, 23, 24, 30, 36, or 48 hours. In further embodiments, the solid dosage form provides a therapeutically effective systemic plasma level of a polyamine transport inhibitor and/or DFMO for at least an 8-hour period. In further embodiments, the solid dosage form provides a therapeutically effective systemic plasma level of a polyamine transport inhibitor and/or DFMO for at least a 14-hour period. In further embodiments, the solid dosage form provides a therapeutically effective systemic plasma level of a polyamine transport inhibitor and/or DFMO for at least an 18-hour period. In further embodiments, the solid dosage form provides a therapeutically effective systemic plasma level of a polyamine transport inhibitor and/or DFMO for at least a 24-hour period.

In one embodiment, a solid dosage form provides a plasma level of a polyamine transport inhibitor and/or DFMO of at least 25, 50, 55, 60, 65, 70, 75, 80, 85, 90, or 95 percent of the peak plasma concentration for at least 4 hours. In certain embodiments, a solid dosage form provides a plasma level of a polyamine transport inhibitor and/or DFMO of at least 75% of the peak plasma concentration for at least 4, 6, 8, 10, 12, 14, 16, 18, 20, 22, or 24 hours. In certain embodiments, a solid dosage form provides a plasma level of a polyamine transport inhibitor and/or DFMO of at least 75% of the peak plasma concentration for at least 4 hours. In certain embodiments, a solid dosage form provides a plasma level of a polyamine transport inhibitor and/or DFMO of at least 75% of the peak plasma concentration for at least 6 hours. In certain embodiments, a solid dosage form provides a plasma level of a polyamine transport inhibitor and/or DFMO of at least 75% of the peak plasma concentration for at least 10 hours. In certain embodiments, a solid dosage form provides a plasma level of a polyamine transport inhibitor and/or DFMO of at least 50% of the peak plasma concentration for at least 6 hours. In certain embodiments, a solid dosage form provides a plasma level of a polyamine transport inhibitor and/or DFMO of at least 50% of the peak plasma concentration for at least 12 hours. In certain embodiments, a solid dosage form provides a plasma level of a polyamine transport inhibitor and/or DFMO of at least 50% of the peak plasma concentration for at least 18 hours. In certain embodiments, a solid dosage form provides a plasma level of a polyamine transport inhibitor and/or DFMO of at least 25% of the peak plasma concentration for at least 18 hours. In some embodiments, the peak plasma concentration is a therapeutically effective concentration. In further embodiments, the percentage of peak plasma concentration is therapeutically effective over the given time period.

Solid dosage forms may be prepared according to any method known to the art for the manufacture of such. Such compositions may contain one or more inert components, where exemplary inert components may be selected from the group of sweetening agents, flavoring agents, coloring agents and preserving agents.

Excipients for solid dosage forms are well known in the art, and are selected to provide various benefits including, for example, ease of administration to the subject, improved dosing compliance, consistency and control of drug bioavailability, assistance with enhanced bioavailability, improved API stability including protection from degradation, and to contribute to the ease of production of a robust and reproducible physical product. Excipients are commonly subdivided into various functional classifications, depending on the role that they are intended to play in the formulation. For solid dosage forms, common excipient roles and exemplary materials that fulfill that role are diluents, e.g., lactose and microcrystalline cellulose, disintegrants, e.g., sodium starch glycolate and croscarmellose sodium, binders, e.g., PVP and HPMC, lubricants, e.g., magnesium stearate, and glidants, e.g., colloidal $SiO_2$. Tablets and capsules often contain a diluent, filler and/or bulking agent, e.g., lactose. Excipients used to formulate the combinations described herein should typically avoid those containing reducing sugar components in order to prevent formation of Schiff-base addition products as degradants.

Excipients may be, for example, inert diluents, such as calcium carbonate, sodium carbonate, and lactose; granulating and disintegrating agents, such as corn starch and alginic acid; binding agents, such as starch, gelatin or acacia; and lubricating agents, such as magnesium stearate, stearic acid and talc.

Tablets may be uncoated or they may be coated, e.g., with an enteric coating, by known techniques, in order to delay disintegration and absorption in the gastrointestinal tract and thereby provide a sustained action over a longer period. Compositions for oral use may also be formed as hard gelatin capsules wherein the combination described herein is mixed with an inert solid diluent, for example, calcium carbonate, or kaolin, or as soft gelatin capsules wherein the combination is mixed with water or an oil medium, for example, peanut oil, liquid paraffin, or olive oil.

Compositions described herein can also be in the form of aqueous suspensions, e.g., where a combination of the disclosure is in admixture with one or more excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water may also be used to provide a combination described herein in admixture with a dispersing or wetting agent, suspending agent and one or more preservatives.

Pharmaceutical compositions may be in the form of a sterile injectable aqueous or oleaginous suspension or a suppository for rectal administration. For topical use, creams, ointments, jellies, solutions or suspensions, etc., containing a combination described herein may be employed. Compositions may also be formulated for administration by inhalation or a transdermal patch by methods known in the art.

In some embodiments, a composition may further comprise one or more additional therapeutically active compounds, e.g., which are beneficially applied in the treatment of a disease, disorder or condition, such as cancer, experienced or potentially experienced by a subject receiving a combination of the disclosure.

As mentioned above, a composition may be formulated as a tablet, capsule or the like. For example, in one embodiment, a composition comprises from about 0.1% to about 50% of a combination of the disclosure; from about 0.1% to about 99.9% of a filler; from about 0% to about 10% of a disintegrant; from about 0% to about 5% of a lubricant; and from about 0% to about 5% of a glidant. For example, in one embodiment, a composition comprises from about 0.1% to about 50% of a combination of the disclosure; from about 0.1% to about 99.9% of a filler; from about 0% to about 10% of a disintegrant; from about 0% to about 5% of a lubricant; and from about 0% to about 5% of a glidant. Optionally, a composition (e.g., in unit dosage form) comprises from about 10 mg to about 300 mg of a polyamine transport inhibitor such as AMXT 1501, or a protonated form thereof, making up from about 2% to about 50% of the tablet content or capsule fill content, for example; from about 0% to about 10% of a disintegrant; from about 0% to about 5% of a lubricant; from about 0% to about 5% of a glidant; and from about 30% to about 98% of a filler. In another embodiment, a composition comprises a combination of the disclosure, from about 0.1% to about 10% of a binder, from about 0% to about 5% of a surfactant, from about 0% to about 10% of an intergranular disintegrant, and from about 0% to about 10% of an extragranular disintegrant.

Examples of binders, fillers, surfactants, disintegrants, lubricants, intergranular disintegrants, extragranular disintegrants and glidants are known in the art, and examples are disclosed herein, and include, a binder selected from copolyvidone, hydroxypropylcellulose, hydroxypropylmethylcellulose, and povidone; a filler selected from a sugar, a starch, a cellulose, and a poloxamer; a surfactant selected from polyoxyethylene sorbitan monooleate, a poloxamer, and sodium lauryl sulfate; an intergranular disintegrant selected from croscarmellose sodium, sodium starch glyconate, and crospovidone. Other examples include a disintegrant selected from povidone and crospovidone; a lubricant which is magnesium stearate; and a glidant which is silicon dioxide.

It may be advantageous to tune the drug ratio in the compositions described herein (e.g., comprising a co-crystal or salt comprising DFMO, or an ionic form thereof, and a compound of structural formula (I), such as AMXT 1501, or a protonated form thereof), e.g., by adding DFMO, or a pharmaceutically acceptable salt thereof, or AMXT 1501, or a pharmaceutically acceptable salt thereof. For example, MYC and RAS oncogenes are known to induce the polyamine metabolic pathway. The increased polyamine levels in tumors expressing MYC and RAS oncogenes are known to induce higher proliferative ability of the underlying tumor cells and provide the cells with a mechanism for immune system evasion. Thus, in some embodiments, a pharmaceutical composition described herein comprises a co-crystal or salt comprising DFMO, or an ionic form thereof, and a compound of structural formula (I), such as AMXT 1501, or a protonated form thereof, and further comprises DFMO, or a pharmaceutically acceptable salt thereof and/or a compound of structural formula (I), such as AMXT 1501, or a pharmaceutically acceptable salt thereof.

Kits can also be used to provide tuning of the drug ratio in accordance with the present disclosure. In some embodiments, a kit comprises a combination of the disclosure and a separate composition comprising DFMO, or a pharmaceutically acceptable salt thereof. In some embodiments, a kit comprises a combination of the disclosure and a separate composition comprising a polyamine transport inhibitor (e.g., the same polyamine transport inhibitor provided in the combination in the kit, such as AMXT 1501 dicaprate), or a pharmaceutically acceptable salt thereof. In some embodiments, a kit comprises a combination of the disclosure and a separate composition comprising a polyamine transport inhibitor (e.g., the same polyamine transport inhibitor provided in the combination in the kit, such as AMXT 1501 dicaprate), or a pharmaceutically acceptable salt thereof, and a further separate composition comprising DFMO, or a pharmaceutically acceptable salt thereof. Written instructions for administering the combination to a subject to treat a disease, disorder or condition described herein, such as cancer, can also be provided in a kit. In some embodiments, a kit comprises a combination of the disclosure and written instructions for administering the combination to a subject to treat a disease, disorder or condition described herein, such as cancer.

Preferably, the compositions provided herein do not have substantially dose-limiting side effects, e.g., gastrointestinal side effects such as nausea, vomiting, diarrhea, abdominal pain, oral mucositis, oral ulceration, pharyngitis, stomatitis, and gastrointestinal ulceration.

Therapeutic Uses

Provided herein is a method of treating cancer in a subject (e.g., a subject in need thereof), comprising administering to the subject a therapeutically effective amount of a combination of the disclosure (e.g., a solid form and/or salt described herein) or a composition described herein comprising a combination of the disclosure.

A variety of cancers are amenable to treatment in accordance with the present disclosure. In some embodiments, the cancer comprises a solid tumor. In some embodiments, the cancer is a solid tumor cancer. In some embodiments, the cancer is a hematological cancer, e.g., a leukemia, lymphoma or myeloma. The cancer may be, for example, breast cancer, prostate cancer, colon cancer or lung cancer. Other cancers that may be treated by appropriate selection of the polyamine transport inhibitor include neuroblastoma, pancreatic, bladder, melanoma, skin cancer, non-Hodgkin lymphoma, kidney cancer, head and neck cancers including glioblastoma, leukemia and other blood cancers, ovarian and thyroid cancers. The cancer may be treated by polyamine transport inhibitors that are specific for oncogenes, e.g., MYC- and/or RAS-derived tumors.

Other cancers amenable to treatment in accordance with the present disclosure include Acute Lymphoblastic Leukemia (ALL); Acute Myeloid Leukemia (AML); Adrenocortical Carcinoma; Adrenocortical Carcinoma, Childhood; AIDS-Related Cancer (e.g., Kaposi Sarcoma, AIDS-Related Lymphoma, Primary CNS Lymphoma); Anal Cancer; Appendix Cancer; Astrocytomas, Childhood; Atypical Teratoid/Rhabdoid Tumor, Childhood, Central Nervous System; Basal Cell Carcinoma of the Skin; Bile Duct Cancer; Bladder Cancer; Bladder Cancer, Childhood; Bone Cancer (including Ewing Sarcoma, Osteosarcoma and Malignant Fibrous Histiocytoma); Brain Tumors/Cancer; Breast Cancer; Burkitt Lymphoma; Carcinoid Tumor (Gastrointestinal); Carcinoid Tumor, Childhood; Cardiac (Heart) Tumors, Childhood; Embryonal Tumors, Childhood; Germ Cell Tumor, Childhood; Primary CNS Lymphoma; Cervical Cancer; Childhood Cervical Cancer; Cholangiocarcinoma; Chordoma, Childhood; Chronic Lymphocytic Leukemia (CLL); Chronic Myelogenous Leukemia (CML); Chronic Myeloproliferative Neoplasms; Colorectal Cancer; Childhood Colorectal Cancer; Craniopharyngioma, Childhood; Cutaneous T-Cell Lymphoma (e.g., Mycosis Fungoides and Sezary Syndrome); Ductal Carcinoma In Situ (DCIS); Embryonal Tumors, Central Nervous System, Childhood; Endometrial Cancer (Uterine Cancer); Ependymoma, Childhood; Esophageal Cancer; Childhood Esophageal Cancer; Esthesioneuroblastoma; Ewing Sarcoma; Extracranial Germ Cell Tumor, Childhood; Extragonadal Germ Cell Tumor; Eye Cancer; Childhood Intraocular Melanoma; Intraocular Melanoma; Retinoblastoma; Fallopian Tube Cancer; Fibrous Histiocytoma of Bone, Malignant, and Osteosarcoma; Gallbladder Cancer; Gastric (Stomach) Cancer; Childhood Gastric (Stomach) Cancer; Gastrointestinal Carcinoid Tumor; Gastrointestinal Stromal Tumors (GIST); Childhood Gastrointestinal Stromal Tumors; Germ Cell Tumors; Childhood Central Nervous System Germ Cell Tumors (e.g., Childhood Extracranial Germ Cell Tumors, Extragonadal Germ Cell Tumors, Ovarian Germ Cell Tumors, Testicular Cancer); Gestational Trophoblastic Disease; Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer; Intraocular Melanoma; Childhood Intraocular Melanoma; Islet Cell Tumors, Pancreatic Neuroendocrine Tumors; Kaposi Sarcoma; Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Childhood Lung Cancer; Lymphoma; Male Breast Cancer; Malignant Fibrous Histiocytoma of Bone and Osteosarcoma; Melanoma; Childhood Melanoma; Melanoma, Intraocular (Eye); Childhood Intraocular Melanoma; Merkel Cell Carcinoma; Mesothelioma, Malignant; Childhood Mesothelioma; Metastatic Cancer; Metastatic Squamous Neck Cancer with Occult Primary; Midline Tract Carcinoma With NUT Gene Changes; Mouth Cancer; Multiple Endocrine Neoplasia Syndromes; Multiple Myeloma/Plasma Cell Neoplasms; Mycosis Fungoides; Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms, Chronic; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip and Oral Cavity Cancer and Oropharyngeal Cancer; Osteosarcoma and Malignant Fibrous Histiocytoma of Bone; Ovarian Cancer; Childhood Ovarian Cancer; Pancreatic Cancer; Childhood Pancreatic Cancer; Pancreatic Neuroendocrine Tumors; Papillomatosis (Childhood Laryngeal); Paraganglioma; Childhood Paraganglioma; Paranasal Sinus and Nasal Cavity Cancer; Parathyroid Cancer; Penile Cancer; Pharyngeal Cancer; Pheochromocytoma; Childhood Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer; Renal Cell (Kidney) Cancer; Retinoblastoma; Rhabdomyosarcoma, Childhood; Salivary Gland Cancer; Sarcoma (e.g., Childhood Rhabdomyosarcoma, Childhood Vascular Tumors, Ewing Sarcoma, Kaposi Sarcoma, Osteosarcoma (Bone Cancer), Soft Tissue Sarcoma, Uterine Sarcoma); Sezary Syndrome; Skin Cancer; Childhood Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; Childhood Stomach (Gastric) Cancer; T-Cell Lymphoma, Cutaneous (e.g., Mycosis Fungoides and Sezary Syndrome); Testicular Cancer; Childhood Testicular Cancer; Throat Cancer (e.g., Nasopharyngeal Cancer, Oropharyngeal Cancer, Hypopharyngeal Cancer); Thymoma and Thymic Carcinoma; Thyroid Cancer; Transitional Cell Cancer of the Renal Pelvis and Ureter; Ureter and Renal Pelvis, Transitional Cell Cancer; Urethral Cancer; Uterine Cancer, Endometrial; Uterine Sarcoma; Vaginal Cancer; Childhood Vaginal Cancer; Vascular Tumors; Vulvar Cancer; and Wilms Tumor and Other Childhood Kidney Tumors.

Metastases of the aforementioned cancers can also be treated in accordance with the methods described herein. In some embodiments, the cancer is a metastatic cancer.

In some embodiments, the cancer is a pediatric cancer. "Pediatric cancer" typically refers to cancer that occurs between birth and fourteen years of age.

In general, there is a myriad of therapeutic uses for the combinations of the disclosure in addition to use as an anti-cancer treatment. For example, polyamine transport inhibitors have been described to have antibiotic, antiviral, anti-inflammatory, anti-sepsis, anti-pain, anti-psychotic, anti-aging, and anti-heart damage activities, among others. Accordingly, also provided herein are methods of treating a disease, disorder or condition in a subject in need thereof, comprising administering to the subject a therapeutically effective amount of a combination of the disclosure (e.g., a solid form and/or salt described herein) or a composition described herein comprising a combination of the disclosure, wherein the disease, disorder or condition would benefit from treatment with an agent having antibiotic, antiviral, anti-inflammatory, anti-sepsis, anti-pain, anti-psychotic, anti-aging and anti-heart damage activity.

As described above, it may be advantageous to tune the drug ratio in accordance with the present disclosure. This can be done, e.g., by adding DFMO, or a pharmaceutically acceptable salt thereof, and/or AMXT 1501, or a pharmaceutically acceptable salt thereof, to a composition described herein. It is also or alternatively possible to tune the drug ratio by administering additional polyamine transport inhibitor and/or DFMO, or a pharmaceutically acceptable salt of the foregoing, to a subject. When additional polyamine transport inhibitor and/or DFMO, or a pharmaceutically acceptable salt of the foregoing, is administered to the subject, the polyamine transport inhibitor and/or DFMO, or a pharmaceutically acceptable salt of the foregoing, can be administered before, after or concurrently with the combination of the disclosure or composition described herein. Further, the additional polyamine transport inhibitor and/or DFMO, or a pharmaceutically acceptable salt of the foregoing, can be administered with any frequency, by any route and in any amount described herein in connection with the combinations and compositions described herein. Further, when additional polyamine transport inhibitor, or a pharmaceutically acceptable salt thereof, and additional DFMO, or a pharmaceutically acceptable salt thereof, is administered to a subject, the polyamine transport inhibitor, or a pharmaceutically acceptable salt thereof, and DFMO, or a pharmaceutically acceptable salt thereof, can be administered before, after or concurrently with one another.

Thus, in some embodiments, a method further comprises administering DFMO, or a pharmaceutically acceptable salt thereof (e.g., a therapeutically effective amount of DFMO, or a pharmaceutically acceptable salt thereof), to the subject. In some embodiments, a method further comprises administering a polyamine transport inhibitor, or a pharmaceutically acceptable salt thereof (e.g., AMXT 1501 dicaprate; a therapeutically effective amount of a polyamine transport inhibitor, or a pharmaceutically acceptable salt thereof, such as AMXT 1501 dicaprate), to the subject.

In some embodiments, a method further comprises administering to a subject one or more additional therapies (e.g., therapeutically active compounds), e.g., which are beneficially applied in the treatment of a disease, disorder or condition, such as cancer, experienced or potentially experienced by a subject receiving a combination described herein. When a combination of the disclosure is administered with one or more additional therapies, the combination can be administered before, after or concurrently with the other therapy(ies). When co-administered concurrently, the combination and additional therapeutically active agent(s) can be in separate formulations or the same formulation. Alternatively, the combination and additional therapeutically active agent(s) can be administered sequentially, either at approximately the same time or at different times, as separate compositions. When the combination of the disclosure and the other therapy are administered as separate formulations or compositions, the combination and the other therapy can be administered by the same route of administration or by different routes of administration. A skilled clinician can determine appropriate timing for administration of each therapy being used in combination (e.g., timing sufficient to allow an overlap of the pharmaceutical effects of the therapies).

The compositions described herein may be administered by oral, parenteral (e.g., intramuscular, intraperitoneal, intravenous, intracerebroventricular, intracisternal injection or infusion, subcutaneous injection, or implant), inhalation spray, nasal, vaginal, rectal, sublingual, or topical routes of administration. In preferred embodiments, the compositions described herein are administered orally.

In the treatment of cancer, the combinations of the disclosure and compositions described herein will be administered at an appropriate dosage level, typically, from about 0.01 mg to about 1,000 mg (e.g., from about 0.01 mg to about 500 mg) per kg patient body weight per day, which can be administered in single or multiple doses. Human dose levels, especially those used for cancer chemotherapy, are alternatively expressed in units of mg/m$^2$/day. The dose may be higher or lower at the discretion of the attending health care professional, based, for example, on that person's experience and knowledge in dealing with the specific medical condition being treated and the condition of the subject. Optionally, the dosage level will be from about 0.1 to about 250 mg/kg per day; or from about 0.5 to about 100 mg/kg per day. A suitable dosage level may be from about 0.01 to about 250 mg/kg per day, from about 0.05 to about 100 mg/kg per day, from about 0.1 to about 100 mg/kg per day, or from about 0.1 to about 50 mg/kg per day. Within this range the dosage may be, for example, from about 0.05 to about 0.5, from about 0.5 to about 5, from about 1 to about 50, or from about 5 to about 50 mg/kg per day. For most large mammals, the total daily dosage will typically be from about 1 milligram to about 5,000 milligrams, or from about 1 milligram to about 2,500 milligrams, or from about 1 milligram to about 1,000 milligrams. For oral administration, the compositions are preferably provided in a solid form or any of the unit dosage forms described herein.

The combinations may be administered as a single daily dose or in divided doses two to six times per day, or in sustained release form. The combinations may be administered on a regimen of 1 to 4 times per day, preferably once or twice per day (e.g., QD or BID), e.g., at the discretion of the attending health care professional.

It will be understood, however, that the specific dose level and frequency of dosage for any particular subject may be varied and will depend upon a variety of factors including the activity of the specific combination employed, the metabolic stability and length of action of the components of the combination, the age, body weight, general health, sex, diet, mode and time of administration, rate of excretion, drug combination, the severity of the particular condition, and the subject undergoing therapy.

EXAMPLES

The Examples and preparations provided below further illustrate and exemplify the subject matter described herein. It is to be understood that the following Examples are not intended to limit the scope of the subject matter described herein in any way. In the following Examples, molecules with a single chiral center, unless otherwise noted, exist as a racemic mixture. Those molecules with two or more chiral centers, unless otherwise noted, can exist as a racemic mixture of diastereomers. Single enantiomers/diastereomers may be obtained by methods known to those skilled in the art. The starting materials and various reactants utilized or referenced in the Examples may be obtained from commercial sources, or are readily prepared from commercially available organic compounds, using methods well known to those skilled in the art.

Example 1: Oral AMXT 1501 Dicaprate in Combination with DFMO

Aminex Therapeutics is developing oral AMXT 1501 dicaprate in combination with oral DFMO for treatment of cancer patients (clinicaltrials.gov NCT03536728). The objective of this clinical trial is to determine the safety and tolerability of oral AMXT 1501 dicaprate in combination with DFMO in patients with advanced solid tumors. Interim data for the pharmacokinetic (PK) behavior of both agents in human subjects has been generated. Both AMXT 1501 dicaprate and DFMO have high water solubility. Due to low bioavailability of AMXT 1501 dicaprate, this agent appears to belong to Biopharmaceutics Classification System (BCS) Class 3.

Clinical Trial Outline. Aminex's clinical trial evaluating the combination of AMXT 1501 dicaprate and DFMO consists of two parts. All solid tumor types are eligible for the trial. Part 1 of the clinical trial evaluated the safety of escalating doses of AMXT 1501 dicaprate, given alone, for two weeks to patients with cancer, then given in combination with a fixed low dose of DFMO for an additional two weeks. This was followed by a two-week recovery period, using a standard 3+3 AMXT 1501 dicaprate dose escalation design. In Part 2 of the clinical trial, the AMXT 1501 dicaprate dose is fixed at 1,800 mg (calculated as the free base content of AMXT 1501 dicaprate), and the DFMO dose will be escalated, following a 3+3 dose escalation protocol design, to determine the maximum tolerated dose (MTD) and recommended Phase 2 dose (RP2D) for the combination. An expansion cohort will be included at the RP2D level to confirm safety and tolerability of the combination. In this clinical trial, AMXT 1501 dicaprate was delivered to fasted patients orally, once daily in enteric-coated capsules. DFMO was delivered orally twice daily in gel capsules. Additional patients will be treated by giving both agents twice daily (BID dosing schedule).

Interim plasma AMXT 1501 and DFMO concentration versus nominal time data are available from Cohorts 1 through 5 of Part 1 of the clinical trial (corresponding to dose levels of 80, 160, 400, 1,200, and 1,800 mg AMXT 1501 alone or in combination with DFMO at 250 mg BID). Twenty-one patients have been dosed in Part 1. Based on the interim pharmacokinetic data from Part 1, mean AMXT 1501 exposure following single or repeat PO dosing increased in a dose-dependent manner at dose levels of 160 mg AMXT 1501 and higher.

Figure 1B:
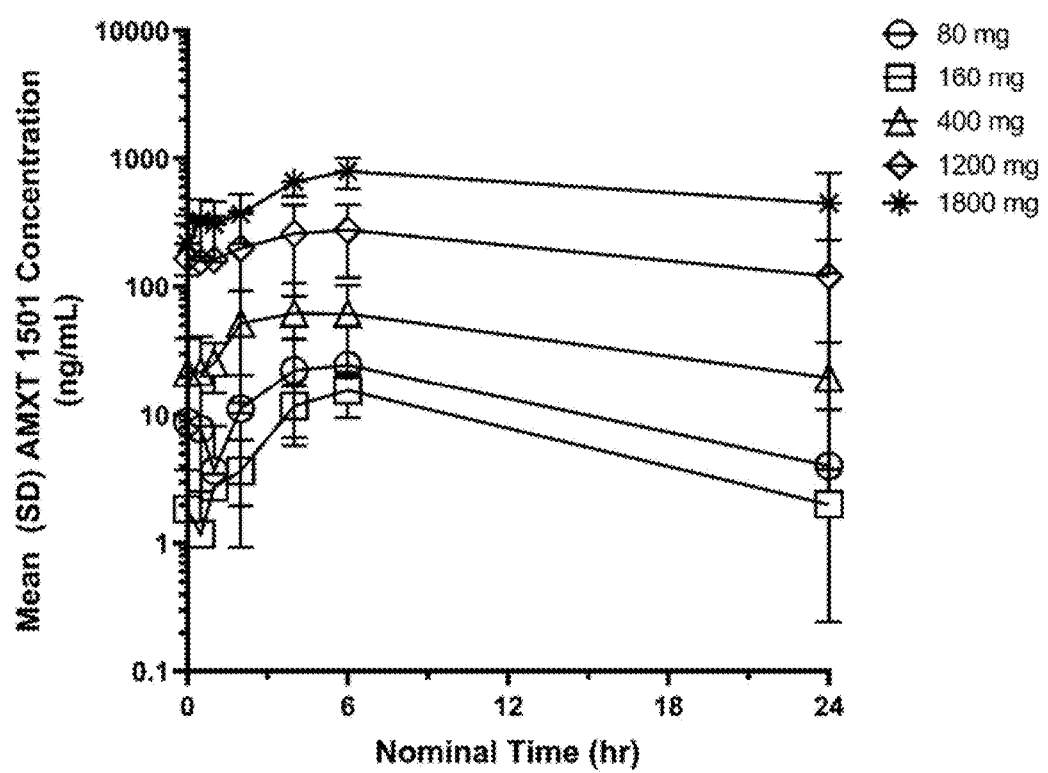
FIG. 1B is a mean plasma concentration versus time profile, and shows the mean plasma concentration of AMXT 1501 after repeat dosing (Day 14).
Figure 2:
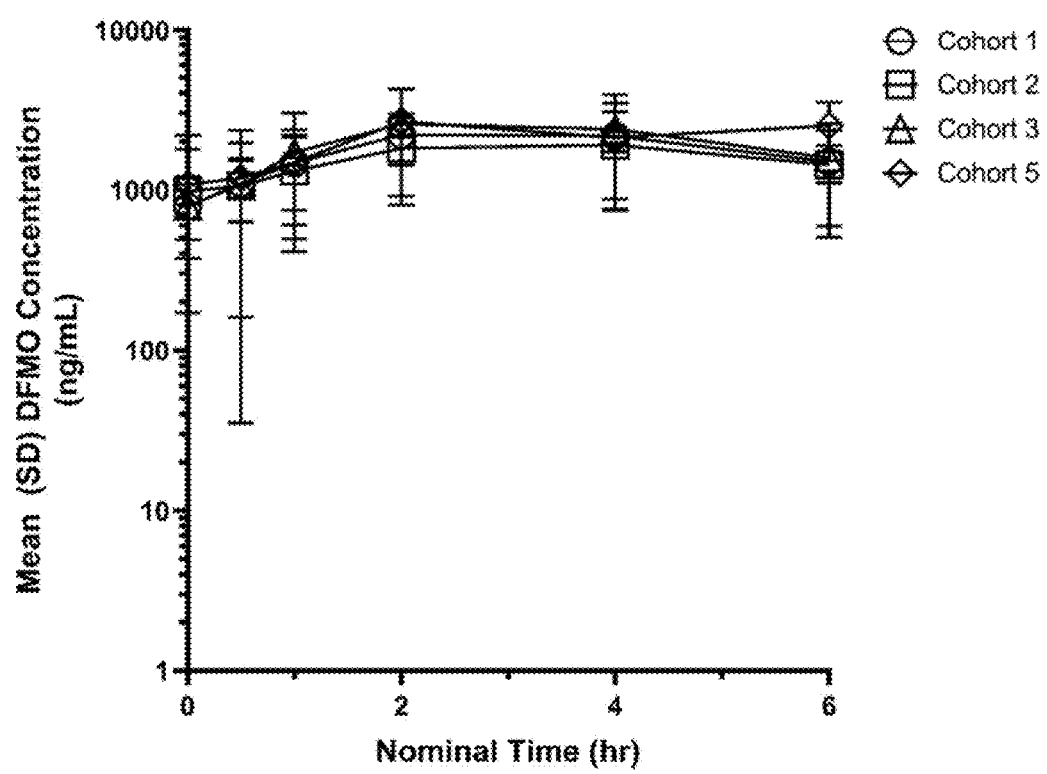
FIG. 2 is a mean plasma concentration versus time profile, and shows the mean plasma concentration of DFMO after repeat dosing (Day 28).

Interim AMXT 1501 and DFMO Clinical Pharmacokinetic (PK) Data. Plasma levels of AMXT 1501 and DFMO were determined using GLP validated LC/MS$^2$ bioanalytical methods. Blood samples from patients were collected over the first three days after a single dose of AMXT 1501 dicaprate on Day 1 of the study, and over a 24-hour period on Day 14 of the study after repeat dosing of AMXT 1501 dicaprate according to the study design. FIGS. 1A and 1B show the resulting AMXT 1501 mean plasma levels from the study. Twenty patients were treated with the 500 mg/day DFMO (split twice daily) from Day 15-28 of the study. DFMO plasma levels were measured at various times post-dosing on Day 28 of the study, and the resultant DFMO plasma concentrations were determined using a validated LC/MS$^2$ bioanalytical assay. Resulting DFMO plasma levels versus time for all 20 patients post-dosing are shown in FIG. 2. All these patients were treated with same DFMO dose and showed an AUC (n=14) average of 11,417 hr*ng/mL, SD 4,870, for a percent CV of 43%.

At the highest AMXT 1501 dose provided to patients (Part 1, Cohort 5: 1,800 mg AMXT 1501), an average $C_{max}$ of 794.25 ng/mL (SD 208.6, for a percent CV of 26%) was observed for plasma AMXT 1501 concentration after repeat dosing (Day 14; n=4 patients). Plasma levels of AMXT 1501 injections. PK assessment of this same dose in 4T1 breast cancer syngeneic tumor-bearing mice showed AMXT 1501 plasma $C_{max}$ values reached 978 ng/mL, with AUC values of 8,270 hr*ng/mL. Importantly, in this mouse study, tumor retention of AMXT 1501 was 14 times higher than plasma, with AUC values of 152,000 hr*ng/mL. Although not wishing to be bound by any particular theory, the difference between the plasma AUC value and the tumor AUC value in mice, suggests that plasma AMXT 1501 levels observed in the clinical trial are an underestimation of tumor target engagement. Patients in Cohort 5 had AUC values 1.72 times higher than plasma levels observed in multiple efficacious mouse studies.

For PK characterization, it is generally assumed that the $C_{max}$ parameter, the maximal plasma level of drug, tracks toxicological endpoints, while the parameter of AUC, measuring sustained plasma drug concentrations, tracks efficacy endpoints. PK data obtained in patients in Part 1 of the trial suggest robust AMXT 1501 plasma coverage, as reflected by the AUC values. Furthermore, sustained, 24-hour plasma levels of AMXT 1501 were observed over the dosing time increment. Given the modest Grades 1 and 2 adverse effects observed in these patients, mainly gastrointestinal in nature (nausea and diarrhea), it is presumed that plasma $C_{max}$ values below 1,000 ng/mL AMXT 1501 are well-tolerated. Importantly, in vitro $EC_{50}$ values for AMXT 1501 against cancer cells are 50 nM, which is equivalent to a 28 ng/mL plasma concentration of AMXT 1501.

Clinical Drug Ratios. Table 1 depicts the various molar ratios of AMXT 1501 to DFMO anticipated during Part 2 of the clinical trial. The optimum ratio of each agent will depend, for example, on tumor target susceptibility, drug tumor distribution and retention and genetic background of the patient and the tumor. Given its goal of demonstration of tolerability and maximally-achievable dose of the two drug agents, Aminex's initial clinical trial dosed patients with a fixed, unit dose level of each agent. It is expected drug dosing for future clinical trials will be performed on the more precise mg/m$^2$ unit basis. Dosing based on m$^2$, also known as Body Surface Area (BSA), tends to be more precise, given it adjusts dose to patient BSA, and indirectly to patient body weight.

TABLE 1

AMXT 1501 - DFMO Drug ratios in Aminex NCT03536728 First-in-Human Clinical Trial.

| Cohort | AMXT 1501 dose (mg) | DFMO dose (mg) | mmoles AMXT 1501 | mmoles DFMO | Molar Ratio DFMO/1501 |
| --- | --- | --- | --- | --- | --- |
| Part 1 - Cohort 5 | 1800 | 500 | 3.2 | 2.1 | 0.67 |
| Part 2 - Cohort 1 | 1800 | 1000 | 3.2 | 4.2 | 1.34 |
| Part 2 - Cohort 2 | 1800 | 2000 | 3.2 | 8.5 | 2.68 |
| Part 2 - Cohort 3 | 1800 | 4000 | 3.2 | 16.9 | 5.36 |
| Part 2 - Cohort 4 | 1800 | 8000 | 3.2 | 33.9 | 10.72 |
| Part 2 - Cohort 5 | 1800 | 16000 | 3.2 | 67.8 | 21.43 | were sustained over the 24-hour dosing time increment. An average AUC value of 14,225 hr*ng/mL (SD 5,017 hr*ng/mL, for a percent CV of 35%) was observed for the four patients in Part 1, Cohort 5.

Figure 3:
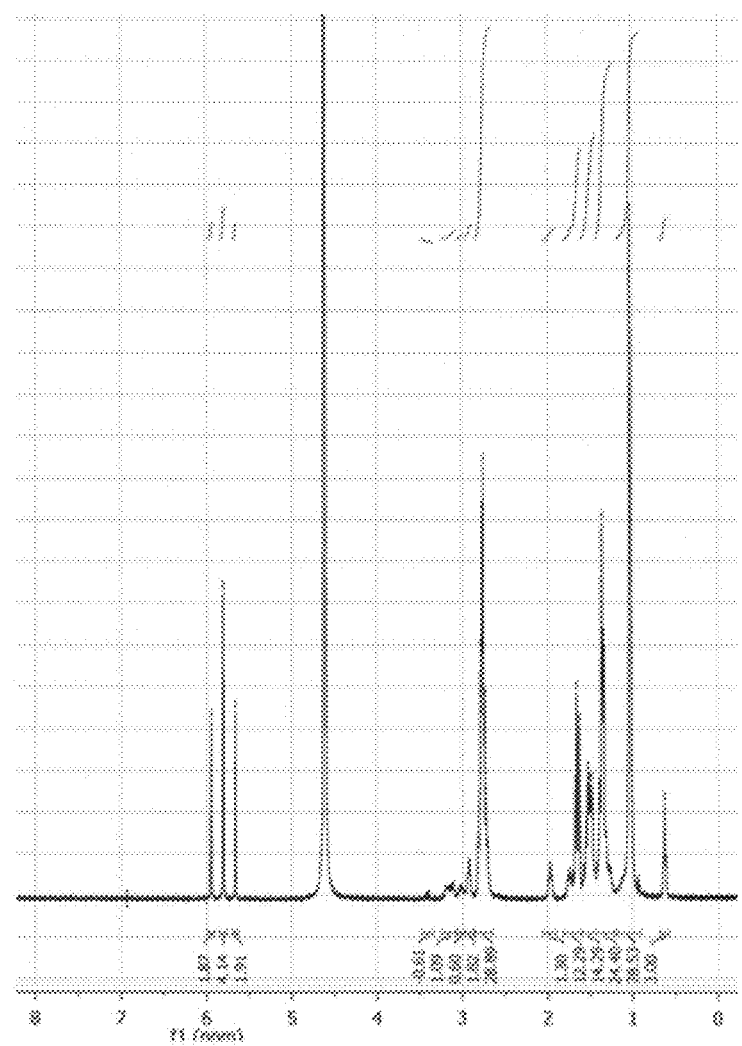
FIG. 3 is a $^1$H NMR spectrum, and shows the presence of both AMXT 1501 and DFMO in Lot 4-138. Data was obtained on a Varian instrument at 400 MHz in $D_2O$ (residual HDO shift set to 4.79 ppm).
Figure 4A:
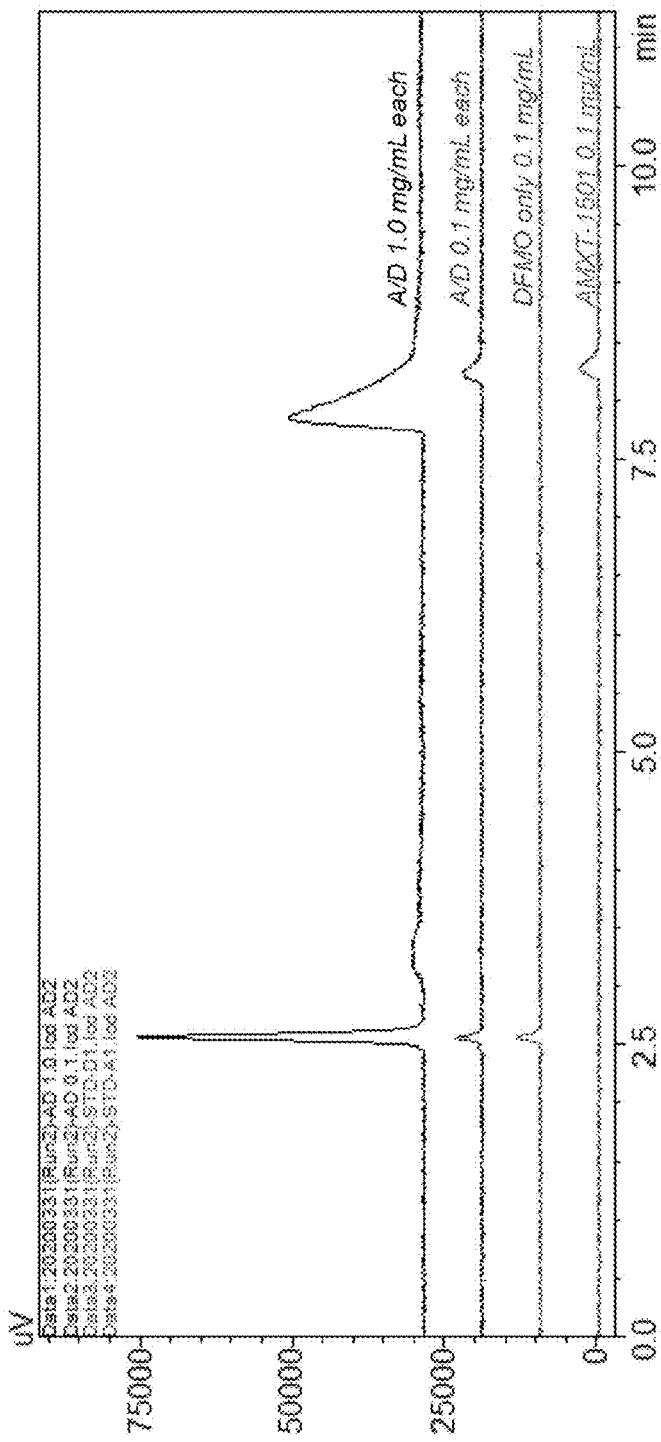
FIG. 4A is HPLC chromatograms, and shows the peaks generated by AMXT 1501 and DFMO under the HPLC conditions described in Example 1.
Figure 4B:
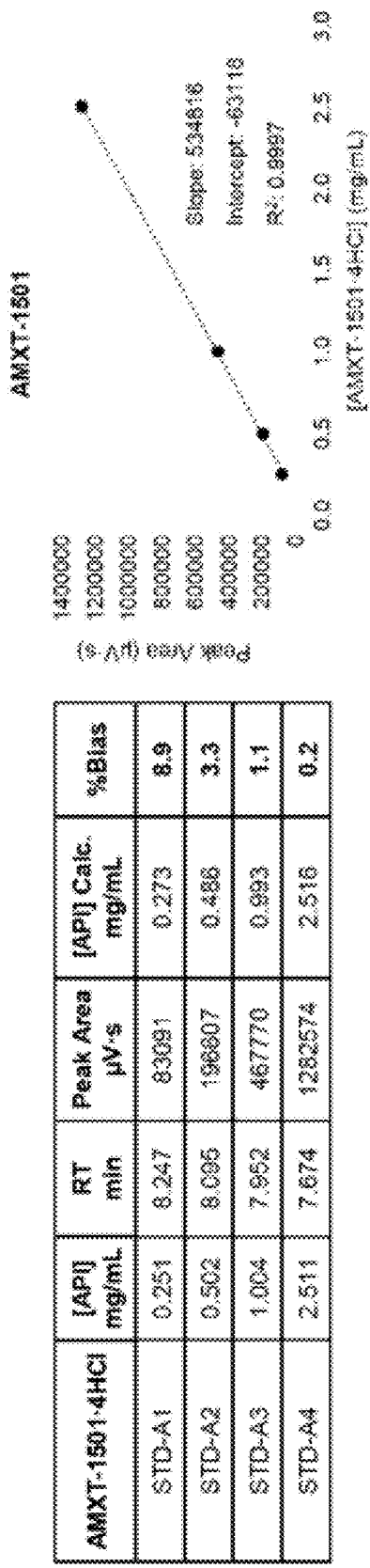
FIG. 4B is a graph, and shows the standard curve produced from HPLC analysis of standard solutions of AMXT 1501.
Figure 4C:
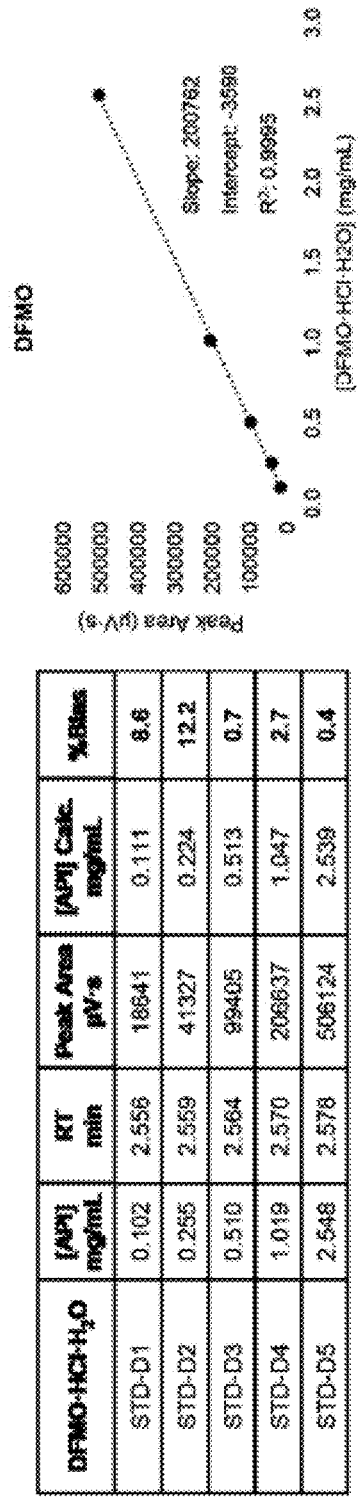
FIG. 4C is a graph, and shows the standard curve produced from HPLC analysis of standard solutions of DFMO.
Figure 4D:
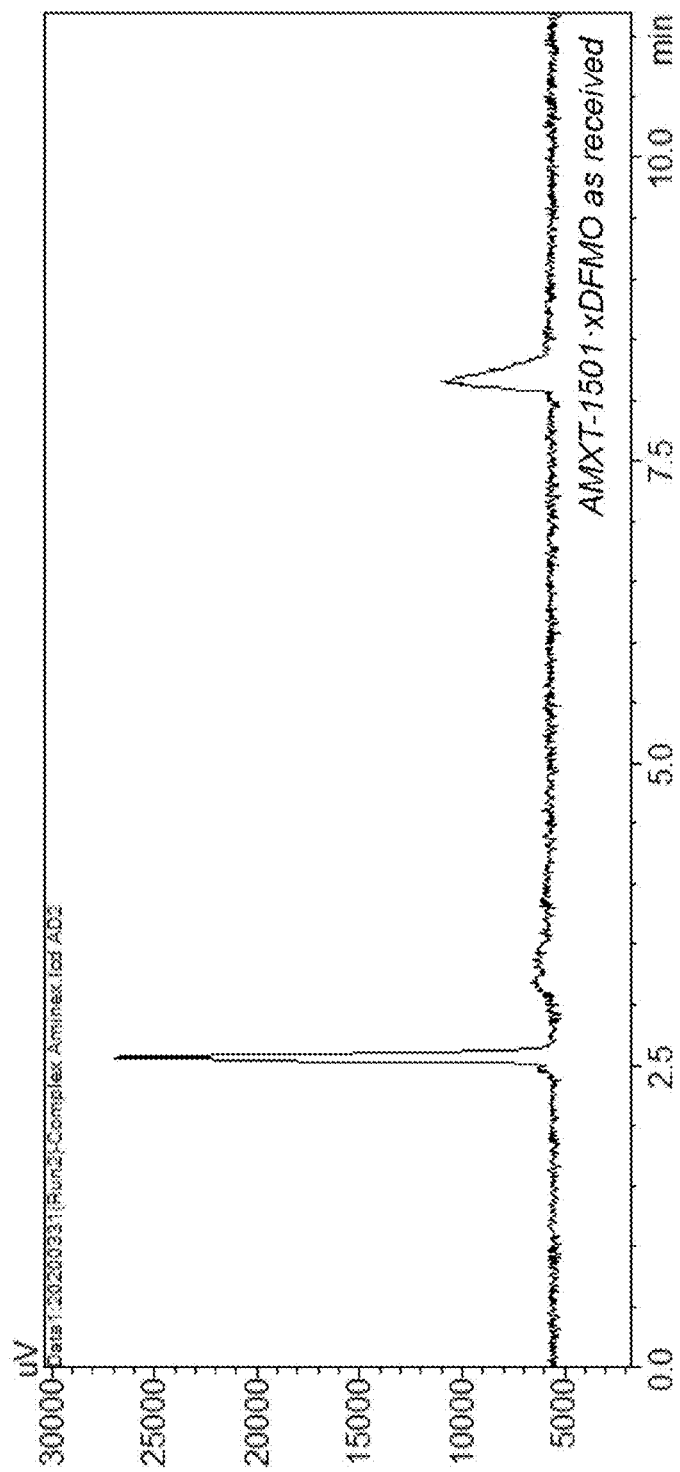
FIG. 4D is a HPLC chromatogram, and shows the peaks produced from HPLC analysis of Lot 4-138.

Multiple positive murine efficacy studies have dosed AMXT 1501 dicaprate at 2.5 mg/kg by daily subcutaneous Example 2: Production of AMXT 1501 Crystalline Salt(s) with DFMO Four molar equivalents of DFMO monohydrochloride monohydrate in 50% EtOH/H$_2$O (6 mL) formed a homogeneous solution upon heating. To this solution was added a homogeneous solution of 1 equivalent of AMXT 1501 free base in absolute EtOH (3 mL; formed with gentle heating), to produce a homogeneous solution at a slightly warm temperature. Flakes began forming after standing at 10 minutes at room temperature. After placing in a freezer, a mass of crystals formed. Filtration gave 61% yield of white solid (Lot #4-138), presuming the tetra-DFMO salt had formed. TLC in $CH_2Cl_2$/MeOH/$NH_4OH$ (60:38:2) showed this white solid contained both AMXT 1501 and DFMO. $^1$H NMR likewise showed the solid contained both AMXT 1501 and DFMO (FIG. 3).

molecular weight of each material. For standard solutions used to prepare the standard curves, calculations were made based on the DFMO and AMXT 1501 free base forms. Chromatograms for standard solution sample injections are shown in FIG. 4A. The standard curves generated from the chromatograms depicted in FIG. 4A are shown in FIGS. 4B and 4C for AMXT 1501 and DFMO, respectively. This analysis resulted in a measured 1 to 7.01 ratio of AMXT 1501 to DFMO in the Lot #4-138 crystalline material used to produce the chromatograph shown in FIG. 4D. The data and calculation used to arrive at the measured ratio are shown below.

TABLE 2

HPLC conditions for AMXT 1501 and DFMO ratio determination.

| Column Information | Name | Agilent Zorbax SB-C3, 50 mm × 4.6 mm, 5 μm |
| --- | --- | --- |
| | Serial #/Lot # | USIF002262 |
| | Catalog # | 883975-909 |
| Mobile Phase A | | 0.1% HFBA (v/v) in water ($H_2O$) |
| Mobile Phase B | | 0.1% HFBA (v/v) in acetonitrile (ACN) |
| Pump Gradient Program | | Time (min)   % Mobile Phase B |
| | | 0   2 |
| | | 4   50 |
| | | 7   50 |
| | | 10   98 |
| | | 20   98 |
| | | 20.1   20 |
| | | 22   2 |
| | | 27   2 |
| Diluent | | $H_2O$/ACN (80/20, v/v) with 0.1% HFBA |
| Flow Rate (mL/min) | | 1.0 |
| Injection Volume | | 20 μL |
| Column Temperature | | 25° C. |
| ELSD Temperature | | 80° C. |
| ELSD Gain | | 1 |

| Sample | Area (A) μV · s | Area (D) μV · s | [A] mg/mL | [D] mg/mL | | |
| --- | --- | --- | --- | --- | --- | --- |
| AD 1.0 mg/mL | 445741 | 201643 | 0.931 | 1.020 | AMXT-1501•4HCl (714.9 g/mol) | AMXT-1501: DFMO = 1:7.01 |
| AMXT-1501•xDFMO as received | 58305 | 88084 | 0.197 | 0.458 | DFMO•HCl•$H_2O$ (236.7 g/mol) | |

$^1$H Nuclear Magnetic Resonance. Using the $^1$H NMR data from the AMXT 1501-DFMO crystal (Lot #4-138) shown in FIG. 3, the ratio of AMXT 1501 to DFMO was estimated. The $CHF_2$ integration intensity at 6.2 ppm is not expected to be highly accurate due to the long T1 time for $CHF_2$. Nevertheless, since this signal is sufficiently isolated, an estimation can be made. Integration of the signal for the terminal lipid chain methyl group of AMXT 1501 (at 0.65 ppm) as 3 protons sets the molar equivalent of AMXT 1501 associated with the crystals to 1. Summation of the integration of the triplet signal due to the —$CHF_2$ for DFMO provides an estimated 7.92 molar ratio of DFMO to AMXT 1501 in these crystals.

High Performance Liquid Chromatography. HPLC analysis with ELSD detection using a gradient method was used to determine the amount of AMXT 1501 and DFMO in samples of Lot #4-138. Table 2 describes HPLC conditions used for the analysis. A standard curve was generated using injections of known amounts of AMXT 1501 4 HCl and DFMO $H_2O$ HCl. Comparisons of peak areas of each drug generated from injection of a sample of the AMXT 1501-DFMO complex to the standard curve was based on the Elemental Analysis. Elemental Analysis results from Lot #4-138 showed C, 44.31 and 44.43; H, 7.83 and 7.69; N, 14.10 and 13.99. These data support the molecular formula shown below, containing 8 moles of DFMO for each mole of AMXT 1501, and 4 equivalents of HCl:

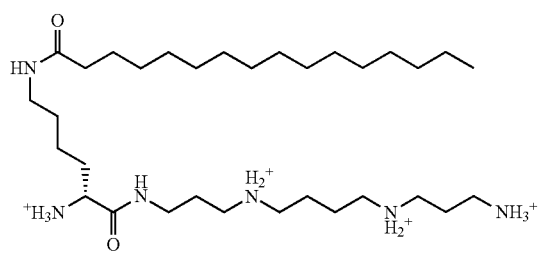

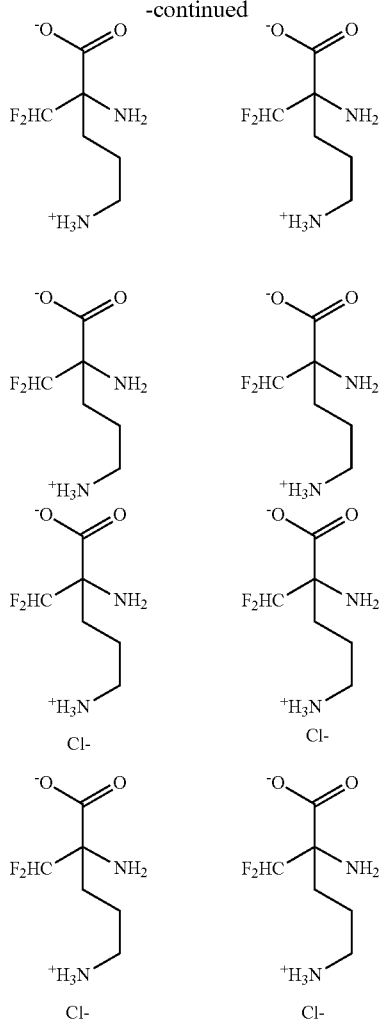

Chemical Formula : $C_{80}H_{168}Cl_4F_{16}N_{22}O_{18}$
Molecular Weight: 2172.13
Elemental Anaylsis: C, 44.24; H, 7.80; Cl, 6.53; F, 13.99; N, 14.19; O, 13.26.

X-Ray Powder Diffraction. The x-ray diffractometer used was a Rigaku Miniflex 6G, where 1 to 3 mg of each solid sample was placed on a sample holder and analyzed using the following parameters: Start Angle, 3.00 degree; Stop Angle, 40.00 degree; Step Width, 0.05 degree; Run Time, 5 minutes, collecting data at 45 kV and 15 mA.

The AMXT 1501-DFMO crystalline complex (Lot #4-138), and the two individual drug agents present as crystalline forms had distinct XRPD diffraction patterns. The diffraction pattern of DFMO alone showed signals at 10 degrees 2Θ that are absent in the diffraction pattern of the AMXT 1501-DFMO crystalline complex. The diffraction pattern from 14-19 degrees 2Θ in the diffraction pattern of the AMXT 1501-DFMO crystalline complex is absent in the diffraction pattern from DFMO alone.

Polarized Light Microscopy. Lot #4-138 material was analyzed by PLM, which revealed the crystalline nature of the complex. FIGS. 6A and 6B show the bright-field and polarized light images, respectively, obtained from PLM analysis of the AMXT 1501-DFMO combination.

Differential Scanning Calorimetry and Thermogravimetric Analysis. The DSC data was collected on a TA Instrument DSC25, where an exact amount (1.0-2.0 mg) of solid sample was weighed on a hermetic aluminum pan, using an analytical balance. The pan was then sealed using a hermetic aluminum lid with pin hole. Each sample was analyzed using the following parameters: Equilibration temperature: 35° C.; Ramping Step: 10.0° C.; Maximum temperature: 400° C.; $N_2$ Purge Flow, 50 mL/min.

The TGA data was collected on a TA Instrument TGA Q500, where approximately 1-3 mg of each solid sample was placed on the thermogravimetric balance and analyzed using the following parameters: Equilibration Temperature: 25° C.; Ramping Step: 10.0° C.; Maximum Temperature: 400° C.; $N_2$ Purge Flow, 60 mL/min.

Figure 7:
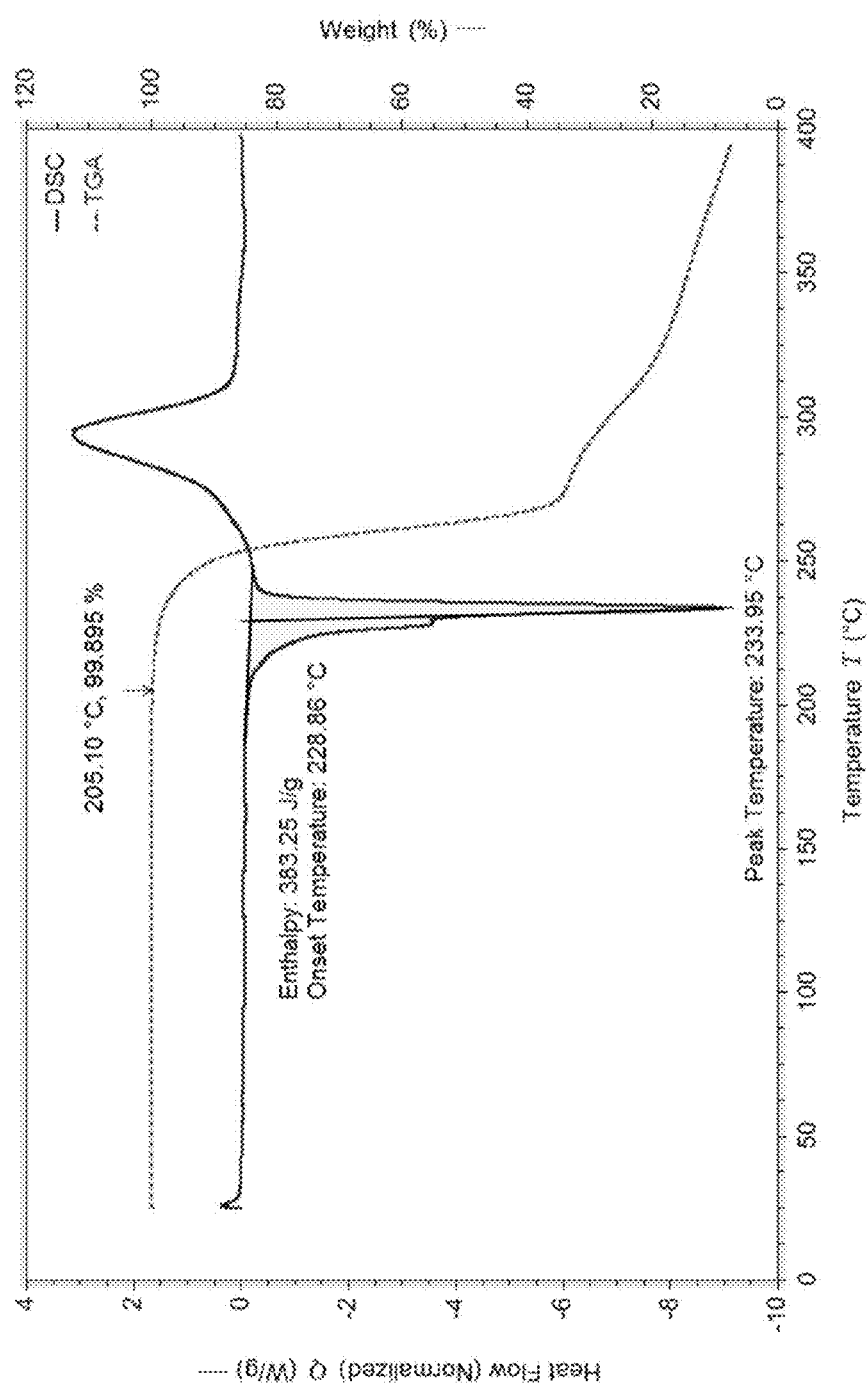
FIG. 7 is a thermogram, and shows the results of differential scanning calorimetry (DSC) and thermogravimetric analysis (TGA) of Lot 4-138.

The AMXT-1501 DFMO complex (Lot #4-138) has a high melting point at 234.0° C., with minimal weight loss prior to 200° C. (FIG. 7). AMXT-1501 free base may contain solvent (MeOH up to 17.2%) which, when removed, improved crystallinity and provided a melting point of 94.0° C. DFMO.HCl.$H_2O$ melted at 157.6° C. with weight loss equivalent to one water loss. DFMO HCl $H_2O$ was previously reported to have a melting point of 183° C. These data show that the AMXT 1501-8DFMO complex has a higher melting point in comparison to each of its individual components. Higher melting solids have a distinct advantage in pharmaceutical products due to improved stability properties.

Example 3: pH Control During AMXT 1501-4DFMO Salt Formation

More consistent control of the AMXT 1501 to DFMO ratio in the salt production was obtained with strict pH control of the starting aqueous solution containing the two drug molecules. Although not wishing to be bound by any particular theory, it is thought that, without strict pH control, DFMO HCl $H_2O$ itself crystallizes from EtOH and $H_2O$ solvent mixtures, and carries variable amounts of AMXT 1501 in the precipitation process. It is hypothesized that addition of AMXT 1501 free base deprotonates DFMO HCl, which precipitates, carrying various amounts of AMXT 1501 free base with it.

Figure 8A:
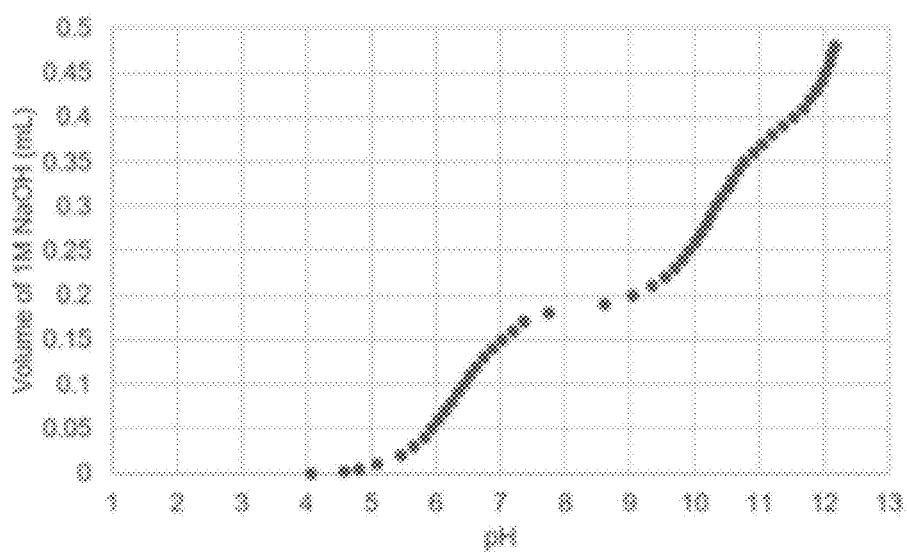
FIG. 8A is a pH titration curve, and shows the results of the pH titration of DFMO.HCl.$H_2O$ (0.1M 2 mL) with 1M NaOH.
Figure 8B:
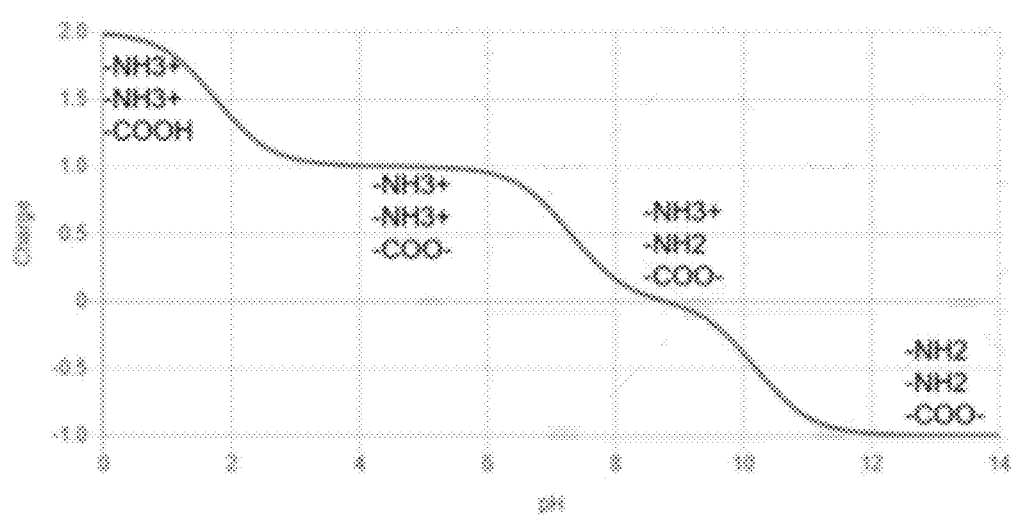
FIG. 8B is a charge state diagram, and shows the charge state of DFMO.HCl.$H_2O$ as a function of pH.

To gain knowledge about the various charge states of the individual drugs in aqueous solution, each were titrated with 1N NaOH while monitoring the pH change of the solution. As shown in FIG. 8A, several inflection points were observed with the DFMO HCl $H_2O$ solution titration. Although not wishing to be bound by any particular theory, it is theorized that the most acidic functional group of DFMO HCl $H_2O$ is the alpha carboxylate group of the amino acid portion of molecule, with a pKa of 6.6. This is a higher than expected pKa compared to acetic acid (4.75) or glycine (2.34), possibly due to the electron-withdrawing effects of the beta difluoro atoms of DFMO's alpha methyl substituent. An alternative explanation of the titration curve shown in FIG. 8A is the inflection at pH 6.6 is due to deprotonation of one of the ammonium groups of DFMO. In either case, as shown by the predicted charge state of DFMO in the diagram of FIG. 8B, ensuring DFMO's carboxylic acid is in its deprotonated carboxylate form requires pH control of its solutions to near, or above, pH 7. Alternatively, as shown in FIG. 8B, in order for sufficient charge association between DFMO and AMXT 1501, one of DFMO's two ammonium ions must be deprotonated to its amino form. This is further supported by the expectation that the alpha amino group of DFMO is less basic than its distal, delta amino group. Additional evidence for protonation of either amino group is the observation of substantial chloride in the elemental analysis results, implying several amino groups in the complex are in their ammonium forms. In either instance, the carboxylate is fully deprotonated at pH 7.

Figure 8C:
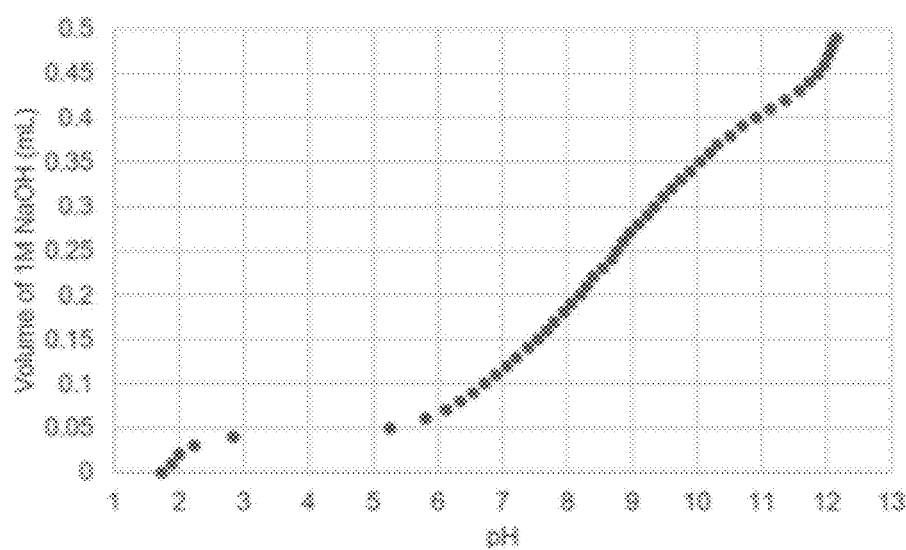
FIG. 8C is a pH titration curve, and shows the results of the pH titration of AMXT 1501•4HCl (0.05 M 2 mL) with 1M NaOH.
Figure 8D:
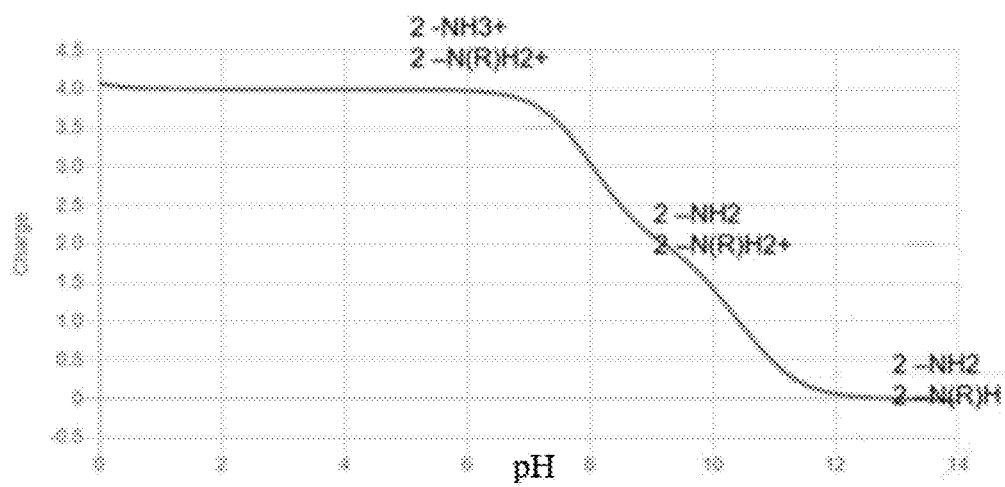
FIG. 8D is a charge state diagram, and shows the charge state of AMXT 1501•4HCl as a function of pH.

AMXT 1501 4HCl in aqueous solution was also titrated with 1M NaOH, and the resulting pH monitored. As shown in FIG. 8C, at pH values near, or less than 7, AMXT 1501 is in its nearly completely protonated tetra-ammonium charge state form. For these reasons, in order to form a solution of DFMO in its carboxylate charged form, while retaining AMXT 1501 in its fully ammonium charged form, requires dissolution at a pH value of near 7. Thus, a pH range of from about 6 to about 8 represents the optimum pH for ionic interactions of AMXT 1501 and DFMO in solution.

For Example 3, AMXT 1501 in its 4HCl salt form was used. A homogeneous, foamy solution of 3.078 g (4.31 mmole) of AMXT 1501 4HCl (MW 714.78 g/mole) was prepared in 20 mL of $H_2O$ with slight warming. To this solution (pH 2) was added 4.3 mL of 1N NaOH (1 equiv), resulting in a pH 10 solution by Whatman pH strips. A separate solution of 4.07 g (MW 236.64, 4 equiv) of DFMO HCl $H_2O$ was prepared in 20 mL of $H_2O$. The pH of the resulting DFMO solution was 5. These two solutions were mixed at room temperature and the resulting homogeneous solution was pH adjusted to pH 7 with portionwise additions of 1M NaOH. A total of 5 mL 1M NaOH were introduced, bringing the pH to 7.

Previous smaller scale experiments showed the unique formation of two separate, homogeneous clear layers when the above solution was treated with the anti-solvent acetonitrile. This was unexpected because acetonitrile is generally completely miscible with aqueous solutions. This observation was exploited in the current example by adding 50 mL of the co-solvent isopropanol to the above AMXT 1501: DFMO pH 7 solution. Again, the resulting solution was completely clear. Addition of 100 mL of the anti-solvent acetonitrile caused the formation of much white precipitation. Shaking caused everything to go back into solution at room temperature. Storage overnight in a −10° C. freezer caused the formation of a white precipitate. Filtration yielded 1.524 g (24%) of a white solid after drying (Lot 5-9).

The clear mother liquor was treated with an additional portion of 150 mL of acetonitrile, heated and decanted from a slight precipitate to give a warm clear solution. This was placed in a −10° C. freezer for two days, when the resulting white precipitate that formed was filtered and dried to give 2.822 g (45%) white solid (Lot 5-11). The pH of the mother liquor was measured to be 7.

TLC analysis of these two lots of crystals showed they both contained the two drug agents. TLC analysis of the mother liquor showed it contained predominately DFMO.

Elemental analysis of these two samples was used to assess composition of these two solids. Results are shown in Tables 3A and 3B. Corresponding structural formulas consistent with the elemental analyses of Lot 5-9 and Lot 5-11 solids, respectively, appear below. Differences in elemental composition results are accounted for by differing amounts of HCl and $H_2O$ associated with the two crops of crystals.

TABLE 3A

Elemental analysis results for Lot 5-9 solid.

Lot 5-9 Theory for AMXT 1501 +
4DFMO + 7HCl + 7 $H_2O$
Formula $C_{56}H_{137}Cl_7F_8N_{14}O_{17}$
MW 1678.93

| Element | Percentage | Found | |
|---------|------------|-------|-------|
| C | 40.06 | 40.03 | 39.94 |
| H | 8.23 | 7.83 | 7.87 |
| N | 11.68 | 11.83 | 11.73 |
| Cl | 14.78 | 15.30 | |
| F | 9.05 | 9.34 | |

TABLE 3B

Elemental analysis results for Lot 5-11 solid.

Lot 5-11 Theory for AMXT 1501 +
4DFMO + 6HCl + $H_2O$
Formula $C_{56}H_{124}Cl_6F_8N_{14}O_{11}$
MW 1534.38

| Element | Percentage | Found | |
|---------|------------|-------|-------|
| C | 43.84 | 43.72 | 43.62 |
| H | 8.15 | 8.19 | 8.23 |
| N | 12.78 | 12.61 | 12.52 |
| Cl | 13.86 | 13.36 | |
| F | 9.91 | 9.88 | |

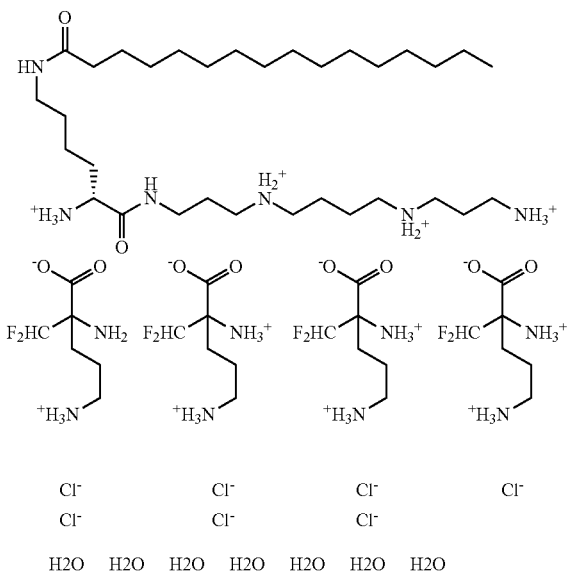

Chemical Formula: $C_{56}H_{137}Cl_7F_8N_{14}O_{17}$
Molecular Weight: 1678.93
Elemental Analysis: C, 40.06; H, 8.23; Cl, 14.78;
F, 9.05; N, 11.68; O, 16.20

-continued

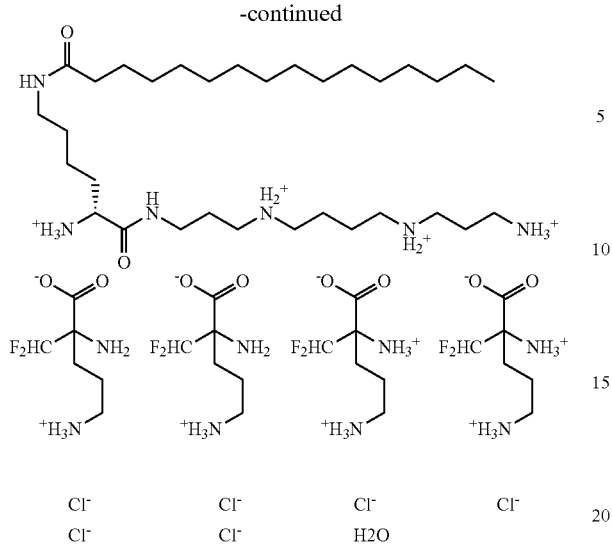

Chemical Formula: $C_{56}H_{124}Cl_6F_8N_{14}O_{11}$
Molecular Weight: 1534.38
Elemental Analysis: C, 43.84; H, 8.15; Cl, 13.68;
F, 9.91; N, 12.78; O, 11.47

HPLC Analysis of Lot 5-9 and Lot 5-11. Using the same HPLC method described in Example 2, the ratio of AMXT 1501 to DFMO for both the Lot 5-9 and Lot 5-11 materials were shown to be near 1 to 4, as expected for a stoichiometric association of DFMO's carboxylate with AMXT 1501's ammonium functional groups at a pH of 7. HPLC calibration curves and results for AMXT 1501-xDFMO ratio analysis are shown in Table 4. In Table 4, Test Solid 1 is Lot 5-9 material and Test Solid 2 is Lot 5-11 material.

TABLE 4

HPLC Calibration curves and results for AMXT 1501-DFMO ratio analysis.

| Sample | Gravimetric Nominal Concentration (mg/mL) | HPLC Analysis | | | | | | |
|---|---|---|---|---|---|---|---|---|
| | | AMXT-1501 RT (min) | AMXT-1501 Area (µV · s) | [AMXT-1501]* (mg/mL) | DFMO RT (min) | DFMO Area (µV · s) | [DFMO]* (mg/mL) | AMXT-1501: DFMO |
| Test Solid 1 | 2.12 | 7.978 | 436999 | 0.86 | 2.557 | 259342 | 1.01 | 3.7 |
| Test Solid 2 | 2.01 | 7.993 | 425344 | 0.84 | 2.558 | 249551 | 0.98 | 3.6 |

*The API concentrations were calculated as free base forms (HCl or $H_2O$ excluded).

Figure 9:
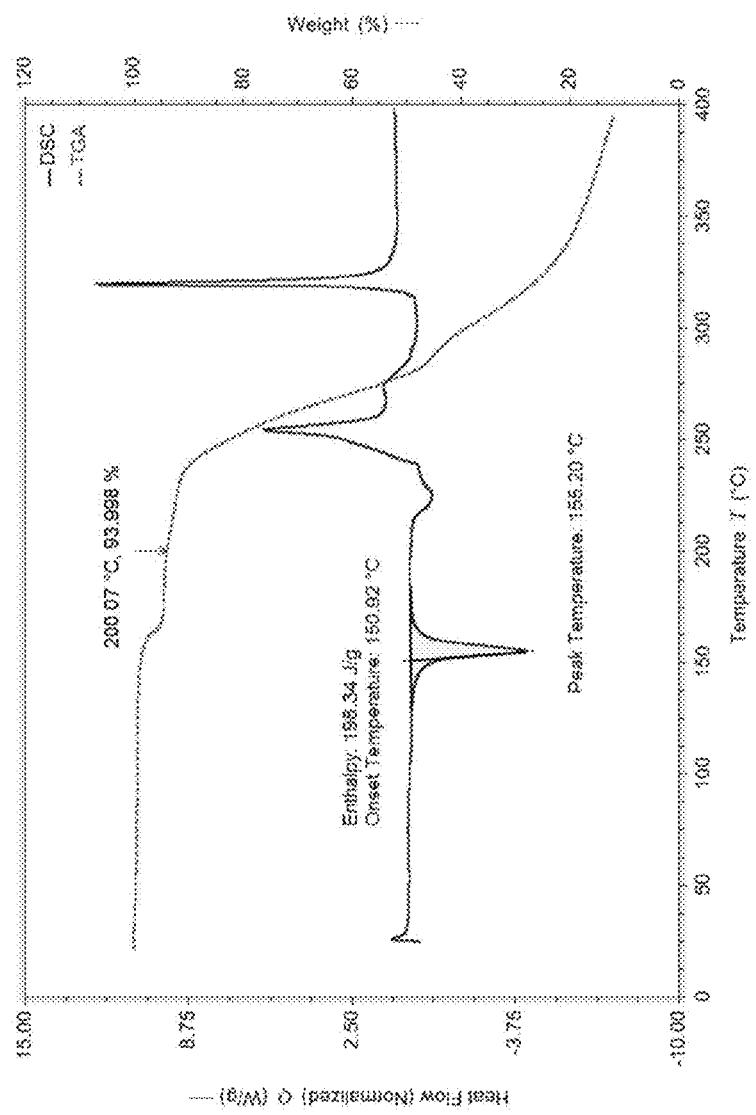
FIG. 9 is a thermogram, and shows the results of DSC and TGA of Test Solid 1 (Lot 5-9).
Figure 10:
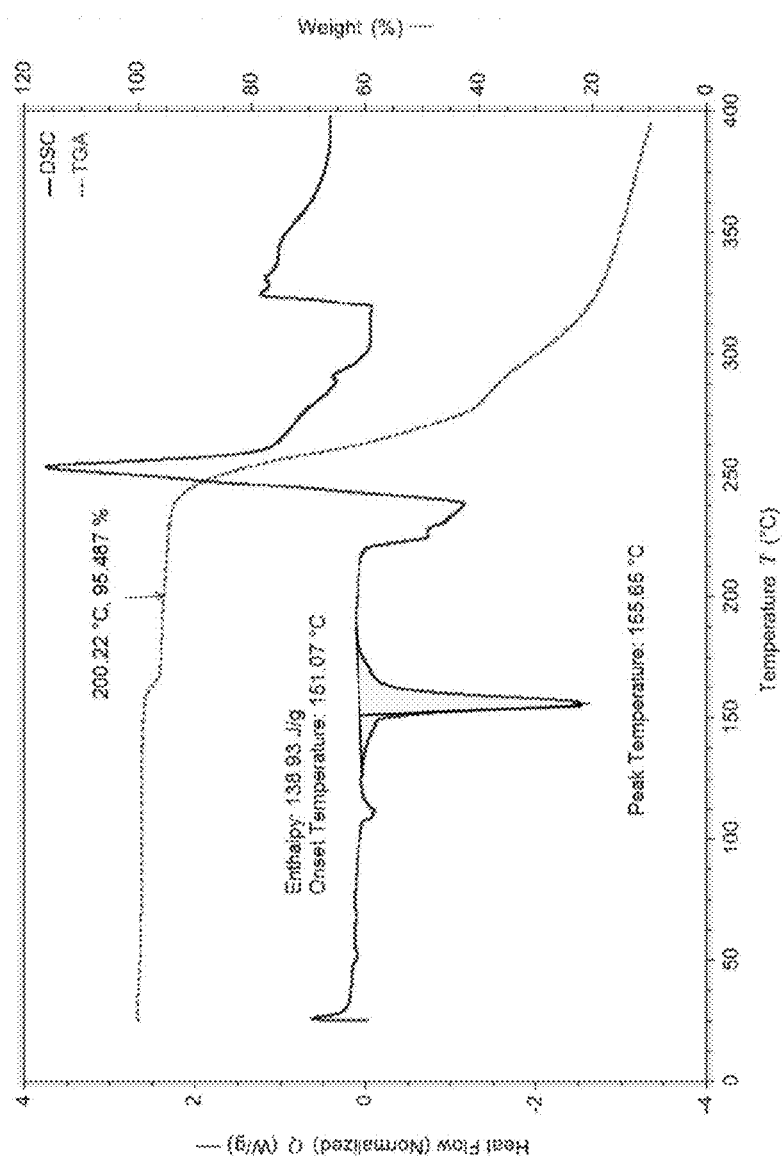
FIG. 10 is a thermogram, and shows the results of DSC and TGA of Test Solid 2 (Lot 5-11).

XRPD, DSC and TGA of Lot 5-9 and Lot 5-11. Using the same XRPD, DSC and TGA conditions described in Example 2, AMXT 1501-DFMO solids from Lots 5-9 and 5-11 were analyzed. The results from DSC and TGA of Lots 5-9 and 5-11 are shown in FIGS. 9 and 10, respectively. Lot 5-9 material (Test Solid 1) had a melting point of 155.20° C. and a weight loss of 6.00 at 200° C., and was composed of 75% water. Lot 5-11 material (Test Solid 2) had a melting point of 155.65° C. and a weight loss of 4.5% at 200° C., and was composed of 1.2% water. DFMO.HCl.$H_2O$ has a melting point of 157.6° C., and is composed of 7.6% water. The results from XRPD analysis of Lots 5-9 and 5-11 are shown in Table 5 and FIG. 11.

TABLE 5

XRPD Peak Summary

| Form | 9.75 (°) | 12.75 | 14.25 | 15.15 | 16.35 | 18.90 | 19.00 | 19.20 | 19.60 | 21.15 |
|---|---|---|---|---|---|---|---|---|---|---|
| Test Solid 1 | X | X | X | X | X |  |  | X | X | X |
| Test Solid 2 | X | X | X |  | X | X | X |  |  | X |
| DFMO•HCl•H$_2$O | X | X |  | X |  |  |  | X | X | X |
| DFMO FB |  |  |  |  |  | X | X | X |  |  |
| AMXT-1501•4HCl |  |  |  |  |  |  |  |  |  |  |
| AMXT-1501 FB |  |  | X |  |  |  |  |  |  |  |

| Form | 22.90 (°) | 23.45 | 24.95 | 25.60 | 25.90 | 27.25 | 28.05 | 28.50 | 29.75 | 30.15 |
|---|---|---|---|---|---|---|---|---|---|---|
| Test Solid 1 | X | X | X | X | X | X | X | X | X | X |
| Test Solid 2 | X | X | X | X | X | X |  | X | X | X |
| DFMO•HCl•H$_2$O | X |  |  | X | X | X | X | X | X | X |
| DFMO FB |  |  | X |  |  |  |  |  |  |  |
| AMXT-1501•4HCl |  |  | X |  |  |  |  |  |  |  |
| AMXT-1501 FB |  | X |  |  |  |  |  |  |  |  |

| Form | 30.90 (°) | 31.95 | 33.10 | 33.30 | 34.10 | 34.85 | 35.20 | 35.40 | 35.90 | 36.4 |
|---|---|---|---|---|---|---|---|---|---|---|
| Test Solid 1 | X | X |  | X | X | X | X | X | X | X |
| Test Solid 2 | X | X | X | X | X |  | X | X | X |  |
| DFMO•HCl•H$_2$O | X | X |  | X | X |  | X |  | X | X |
| DFMO FB |  |  | X |  |  |  | X |  |  |  |
| AMXT-1501•4HCl |  |  |  |  |  |  |  |  |  |  |
| AMXT-1501 FB |  |  |  |  |  |  |  |  |  |  |

Repeat crystallization studies at pH 7.5 and pH 7.8 resulted in solids shown to contain a ratio of 1:3 AMXT 1501/DFMO by the HPLC methods described above. Table 6 summarizes these HPLC assay results.

TABLE 6

HPLC assay of obtained solids after crystallization at pH 7.5 and pH 7.8.

| Sample* | AMXT-1501 RT (min) | AMXT-1501 Area (µV · s) | [AMXT-1501]** (mg/mL) | DFMO RT (min) | DFMO Area (µV · s) | [DFMO]** (mg/mL) | A:D | A:D (avg) |
|---|---|---|---|---|---|---|---|---|
| Solid pH 7.5 (1) | 7.913 | 687707 | 1.049 | 2.558 | 278724 | 0.995 | 2.96 | 3.0 |
| Solid pH 7.5 (2) | 7.913 | 630368 | 0.969 | 2.557 | 263607 | 0.943 | 3.04 |  |
| Solid pH 7.8 (1) | 7.942 | 604901 | 0.934 | 2.557 | 269857 | 0.964 | 3.23 | 3.1 |

TABLE 6-continued

HPLC assay of obtained solids after crystallization at pH 7.5 and pH 7.8.

| Sample* | AMXT-1501 RT (min) | AMXT-1501 Area (μV · s) | [AMXT-1501]** (mg/mL) | DFMO RT (min) | DFMO Area (μV · s) | [DFMO]** (mg/mL) | A:D | A:D (avg) |
|---|---|---|---|---|---|---|---|---|
| Solid PH 7.8 (2) | 7.931 | 619500 | 0.954 | 2.556 | 258713 | 0.926 | 3.03 | |

*Solids were analyzed with HPLC-ELSD assay in replicates.
**The API concentrations were calculated as free base forms (HCl or $H_2O$ excluded).

The ratio of polyamine transport inhibitor to DFMO is expected to vary according to the polyamine transport inhibitor:DFMO stoichiometry, together with the exact crystallization conditions utilized. Processes disclosed herein, such as precise pH control, together with optimized choice of solvent and anti-solvent pairs are very useful to form such materials. Furthermore, combination of any of the examples described herein would be expected to improve drug handling and stability properties and provide more convenient patient dosing formats and hence patient compliance. Various chemical analogs of the examples given herein would also be envisioned to form salts with DFMO.

Example 4: Complexes of DFMO with Other Polyamine Transport Inhibitors

DFMO is complexed with other polyamine transport inhibitors, such as those in Table 7.

TABLE 7

Structures of example polyamine transport inhibitors.

| Polyamine Transport Inhibitor | Structure |
|---|---|
| AMXT 1501 | 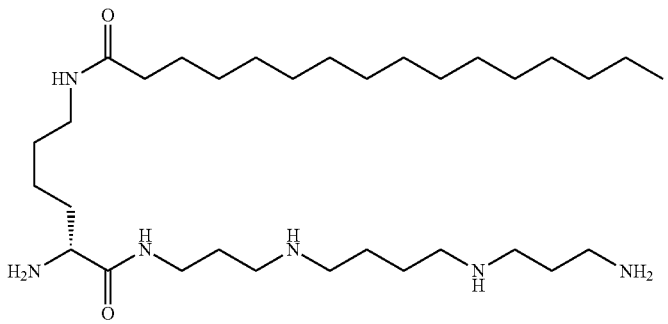 [SMILES: CCCCCCCCCCCCCCCC(=O)NCCCC[C@@H](N)C(=O)NCCCNCCCCNCCCN] |
| AMXT 1569 | 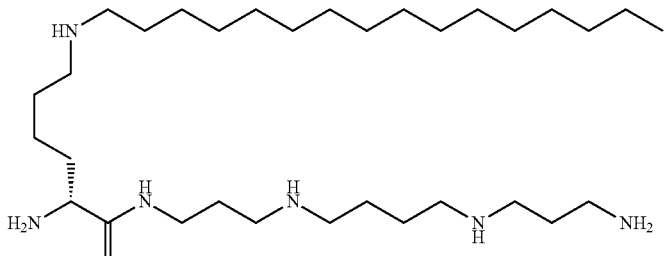 |

TABLE 7-continued

Structures of example polyamine transport inhibitors.

| Polyamine Transport Inhibitor | Structure |
|---|---|
| AMXT 1505 | (structure) |
| AMXT 1426 | (structure) |
| AMXT 2030 | (structure) |

REFERENCES

1. Casero, R. A., Jr., Murray Stewart, T. & Pegg, A. E. Polyamine metabolism and cancer: treatments, challenges and opportunities. *Nat Rev Cancer* 18, 681-695 (2018).
2. Amidon, G. L., Lennernas, H., Shah, V. P. & Crison, J. R. A theoretical basis for a biopharmaceutic drug classification: the correlation of in vitro drug product dissolution and in vivo bioavailability. *Pharm Res* 12, 413-420 (1995).
3. Burns, M. R., Graminski, G. F., Weeks, R. S., Chen, Y. & O'Brien, T. G. Lipophilic lysine-spermine conjugates are potent polyamine transport inhibitors for use in combination with a polyamine biosynthesis inhibitor. *J Med Chem* 52, 1983-1993 (2009).
4. Gamble, L. D., et al. Inhibition of polyamine synthesis and uptake reduces tumor progression and prolongs survival in mouse models of neuroblastoma. *Sci Transl Med* 11(2019).
5. Hayes, C. S., et al. Polyamine-blocking therapy reverses immunosuppression in the tumor microenvironment. *Cancer Immunol Res* 2, 274-285 (2014).
6. Hayes, C. S., Burns, M. R. & Gilmour, S. K. Polyamine blockade promotes antitumor immunity. *Oncoimmunology* 3, e27360 (2014).
7. Saulnier Sholler, G. L., et al. A Phase I Trial of DFMO Targeting Polyamine Addiction in Patients with Relapsed/Refractory Neuroblastoma. *PLoS One* 10, e0127246 (2015).
8. Carbone, P. P., et al. Bioavailability study of oral liquid and tablet forms of alpha-difluoromethylornithine. *Clin Cancer Res* 6, 3850-3854 (2000).
9. Na-Bangchang, K., et al. The pharmacokinetics of eflornithine (alpha-difluoromethylornithine) in patients with late-stage T.b. gambiense sleeping sickness. *Eur J Clin Pharmacol* 60, 269-278 (2004).
10. Schultheiss, N. & Newman, A. Pharmaceutical Cocrystals and Their Physicochemical Properties. *Cryst Growth Des* 9, 2950-2967 (2009).
11. Neubert, R. Ion pair transport across membranes. *Pharm Res* 6, 743-747 (1989).
12. Neubert, R. & Dittrich, T. Ion pair approach of ampicillin using in vitro methods. *Pharm Acta Helv* 65, 186-188 (1990).
13. Hatanaka, T., Kamon, T., Morigaki, S., Katayama, K. & Koizumi, T. Ion pair skin transport of a zwitterionic drug, cephalexin. *J Control Release* 66, 63-71 (2000).
14. Ivaturi, V. D. & Kim, S. K. Enhanced permeation of methotrexate in vitro by ion pair formation with L-arginine. *J Pharm Sci* 98, 3633-3639 (2009).

15. Benaouda, F., et al. Ion-Pairing with Spermine Targets Theophylline To the Lungs via the Polyamine Transport System. *Mol Pharm* 15, 861-870 (2018).
16. Bello-Fernandez, C., Packham, G. & Cleveland, J. L. The ornithine decarboxylase gene is a transcriptional target of c-Myc. *Proc Natl Acad Sci USA* 90, 7804-7808 (1993).
17. Origanti, S. & Shantz, L. M. Ras transformation of RIE-1 cells activates cap-independent translation of ornithine decarboxylase: regulation by the Raf/MEK/ERK and phosphatidylinositol 3-kinase pathways. *Cancer Res* 67, 4834-4842 (2007).
18. Chang, B. K., Libby, P. R., Bergeron, R. J. & Porter, C. W. Modulation of polyamine biosynthesis and transport by oncogene transfection. *Biochem Biophys Res Commun* 157, 264-270 (1988).
19. Soda, K. The mechanisms by which polyamines accelerate tumor spread. *J Exp Clin Cancer Res* 30, 95 (2011).
20. Metcalf, B. W., et al. Catalytic irreversible inhibition of mammalian ornithine decarboxylase (E.C.4.1.1.17) by substrate and product analogs. *Journal of the American Chemical Society* 100, 2551-2553 (1978).
21. Williams-Ashman, H. G. & Schenone, A. Methyl glyoxal bis(guanylhydrazone) as a potent inhibitor of mammalian and yeast S-adenosylmethionine decarboxylases. *Biochem Biophys Res Commun* 46, 288-295 (1972).
22. Seppanen, P. Some properties of the polyamine deprivation-inducible uptake system for methylglyoxal bis (guanylhydrazone) in tumor cells. *Acta Chem Scand B* 35, 731-736 (1981).
23. Warrell, R. P., Jr., Coonley, C. J. & Burchenal, J. H. Sequential inhibition of polyamine synthesis. A phase I trial of DFMO (alpha-difluoromethylornithine) and methyl-GAG [methylglyoxal-bis(guanylhydrazone)]. *Cancer Chemother Pharmacol* 11, 134-136 (1983).
24. Stanek, J., et al. 4-Amidinoindan-1-one 2'-amidinohydrazone: a new potent and selective inhibitor of S-Adenosylmethionine decarboxylase. *J Med Chem* 36, 2168-2171 (1993).
25. Libby, P. R., Henderson, M., Bergeron, R. J. & Porter, C. W. Major increases in spermidine/spermine-N1-acetyltransferase activity by spermine analogues and their relationship to polyamine depletion and growth inhibition in L1210 cells. *Cancer Res* 49, 6226-6231 (1989).
26. Muth, A., et al. Polyamine transport inhibitors: design, synthesis, and combination therapies with difluoromethylornithine. *J Med Chem* 57, 348-363 (2014).
27. Gilmour, S. K., Alexander, E. T., Mariner, K., Donnelly, J. & Phanstiel, O. Polyamine Blocking Therapy Decreases Survival of Tumor-Infiltrating Immunosuppressive Myeloid Cells and Enhances the Anti-Tumor Efficacy of PD-1 Blockade. *Mol Cancer Ther* (2020).

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A salt of a deprotonated form of difluoromethylornithine (DFMO) and a protonated form of a compound of the following structural formula:

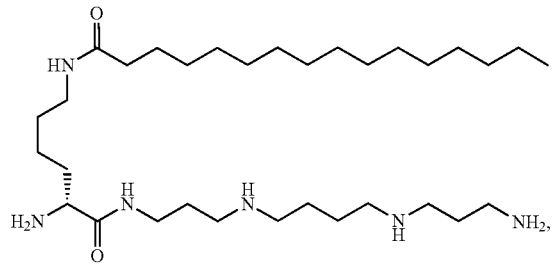

(AMXT 1501)

and optionally an anion of a pharmaceutically acceptable acid or base, a cation of a pharmaceutically acceptable acid or base, or both.

2. A crystalline solid form of a deprotonated form of DFMO and a protonated form of a compound of the following structural formula:

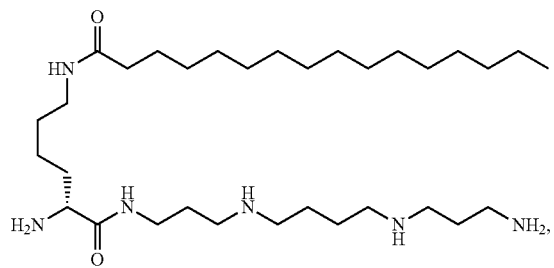

(AMXT 1501)

and optionally a coformer, one or more additional ionic species, or a coformer and one or more additional ionic species.

3. The crystalline solid form of claim 2, characterized by an x-ray diffraction pattern in accordance with that depicted in FIG. 5 or one of those depicted in FIG. 11.

4. The crystalline solid form of claim 2, wherein a coformer is present.

5. The crystalline solid form of claim 2, wherein the molar ratio of the deprotonated form of DFMO and the protonated form of AMXT 1501 is from about one to one (1:1) to about 10 to one (10:1).

6. A pharmaceutical composition comprising a crystalline solid form of claim 2, and a pharmaceutically acceptable excipient.

7. The pharmaceutical composition of claim 6, formulated for oral administration.

8. A method of treating cancer in a subject in need thereof, comprising administering to the subject a therapeutically effective amount of a crystalline solid form of claim 3.

9. The crystalline solid form of claim 4, wherein the coformer is water.

10. The crystalline solid form of claim 2, wherein one or more additional ionic species are present.

11. The crystalline solid form of claim 10, wherein the one or more additional ionic species are anionic.

12. The salt of claim 1, wherein an anion and a cation of a pharmaceutically acceptable acid are present.

13. The salt of claim 12, wherein the pharmaceutically acceptable acid is an inorganic acid.

14. The salt of claim 12, wherein the pharmaceutically acceptable acid has a $pK_a$ difference of greater than or equal to 2 compared to DFMO or AMXT 1501.

15. A hydrate of the salt of claim 1.

16. A method of making a crystalline solid form of claim 2, comprising:
   combining the AMXT 1501, or a salt thereof, and DFMO, or a salt thereof, in a solvent to provide a solution having a pH of about 6 to about 8, wherein the solvent is a polar protic solvent or mixture of solvents comprising a polar protic solvent; and
   inducing precipitation of the crystalline solid form from the solution.

17. The method of claim 16, wherein the solution has a pH of near 7.

18. The method of claim 16, wherein the polar protic solvent is water.

19. The method of claim 16, further comprising adding a non-solvent to the solution, thereby inducing precipitation of the crystalline solid form from the solution.

20. The method of claim 19, wherein the non-solvent is acetonitrile.

21. A solvate of the salt of claim 1.

22. The crystalline solid form of claim 2, wherein a coformer and one or more additional ionic species are present.

* * * * *